(12) United States Patent
Dumas et al.

(10) Patent No.: US 11,635,934 B2
(45) Date of Patent: Apr. 25, 2023

(54) SYSTEMS AND METHODS FOR IDENTIFYING SEGMENTS OF MUSIC HAVING CHARACTERISTICS SUITABLE FOR INDUCING AUTONOMIC PHYSIOLOGICAL RESPONSES

(71) Applicant: MIIR Audio Technologies, Inc., Minnetonka, MN (US)

(72) Inventors: Roger Dumas, Wayzata, MN (US); Jon Beck, Minneapolis, MN (US); Aaron Prust, Crystal, MN (US); Gary Katz, Yonkers, NY (US); Paul J. Moe, Minnetonka, MN (US); Daniel J. Levitin, Los Angeles, CA (US)

(73) Assignee: MIIR Audio Technologies, Inc., Minnetonka, MN (US)

( * ) Notice: Subject to any disclaimer, the term of this patent is extended or adjusted under 35 U.S.C. 154(b) by 0 days.

(21) Appl. No.: 17/841,119

(22) Filed: Jun. 15, 2022

(65) Prior Publication Data
US 2022/0398063 A1    Dec. 15, 2022

Related U.S. Application Data

(60) Provisional application No. 63/210,863, filed on Jun. 15, 2021, provisional application No. 63/227,559, filed on Jul. 30, 2021.

(51) Int. Cl.
*G10H 1/00* (2006.01)
*G06F 3/16* (2006.01)
*A61B 5/00* (2006.01)

(52) U.S. Cl.
CPC .............. *G06F 3/16* (2013.01); *G10H 1/0008* (2013.01); *A61B 5/4035* (2013.01); *G10H 2210/061* (2013.01); *G10H 2250/055* (2013.01)

(58) Field of Classification Search
CPC ....... G10H 2210/066; G10H 2210/076; G10H 1/00; G10H 2240/131; G10H 2210/086;
(Continued)

(56) References Cited

U.S. PATENT DOCUMENTS

2016/0210951 A1\* 7/2016 Rutledge ................ G10H 1/38
2017/0148468 A1\* 5/2017 Kim ....................... G10H 1/40
(Continued)

FOREIGN PATENT DOCUMENTS

CN           107802938 B       4/2021
EP             3644306 A1 \*   4/2020 ........... G10H 1/0008
(Continued)

OTHER PUBLICATIONS

Roberts, et al. Autonomous sensory meridian response: Scale development and personality correlates. Psychology of Consciousness: Theory Research, and Practice, 6(1), 22-39. 2019.
(Continued)

*Primary Examiner* — Marlon T Fletcher
(74) *Attorney, Agent, or Firm* — Barnes & Thornburg LLP

(57) ABSTRACT

Systems and methods for identifying the most impactful moments or segments of music, which are those most likely to elicit a chills effect in a human listener. A digital music signal is processed using two or more objective processing metrics that measure acoustic features known to be able to elicit the chills effect. Individual detection events are identified in the output of each metric based on the output being above or below thresholds relative to the overall output. A combination algorithm aggregates concurrent detection events to generate a continuous concurrence data set of the number of concurrent detection events during the music signal, which can be calculated per beat. A phrase detection algorithm can identify impactful segments of the music
(Continued)

based on at least one of peaks, peak-proximity, and a moving average of the continuous concurrence data.

30 Claims, 33 Drawing Sheets

(58) Field of Classification Search
CPC ............... G10H 2240/145; G10H 1/46; G10H 2210/061; G10H 2210/091; G10H 2210/125; G10H 3/125; G10H 2210/056; G10H 2210/051; G10H 2240/075; G10H 2210/031; G10H 2240/141; G10H 1/0091; G10H 2220/371; G10H 2240/325; G10H 2220/081; G10H 2210/265; G10H 2220/376; G10H 2240/121; G10H 2220/086
See application file for complete search history.

(56) References Cited

U.S. PATENT DOCUMENTS

| | | | | |
|---|---|---|---|---|
| 2019/0022351 | A1* | 1/2019 | McCarthy | A61M 21/02 |
| 2020/0365125 | A1* | 11/2020 | Senn | G06F 3/017 |
| 2021/0338973 | A1* | 11/2021 | Poltorak | A61B 5/165 |

FOREIGN PATENT DOCUMENTS

| | | | | |
|---|---|---|---|---|
| WO | WO-0169575 | A1 * | 9/2001 | G09B 15/023 |
| WO | WO-2019097236 | A1 * | 5/2019 | G06F 16/60 |
| WO | WO-2021168563 | A1 * | 9/2021 | |

OTHER PUBLICATIONS

Rogenmoser, et al. Independent component processes underlying emotions during natural music listening. Social Cognitive and Affective Neuroscience. 2016.
Sachs, et al. Brain connectivity reflects human aesthetic responses to music. Social Cognitive and Affective Neuroscience, 11(6), 884-891. 2016.
Sachs, et al. Dynamic intersubject neural synchronization reflects affective responses to sad music. NeuroImage, 218 (Jun. 2019), 116512. 2020.
Salimpoor, et al. Anatomically distinct dopamine release during anticipation and experience of peak emotion to music. Nature Neuroscience, 14(2), 257-262. 2011.
Salimpoor, et al. Interactions between the nucleus accumbens and auditory cortices predict music reward value. Science, 340(6129), 216-219. 2013.
Sallavanti, et al. The role of complexity in music uses. Psychology of Music, 44(4). 2016.
Schaefer. Music-evoked emotions-Current studies. In Frontiers in Neuroscience (vol. 11) Nov. 2017.
Schäfer, et al. Can personality traits predict musical style preferences? A meta-analysis. Personality and Individual Differences, 116, 265-273. 2017.
Schäfer, et al. How music changes our lives: A qualitative study of the long-term effects of intense musical experiences. Psychology of Music, 42(4), 525-544. 2014.
Schuller. Speech emotion recognition: Two decades in a nutshell, benchmarks, and ongoing trends. Communications of the ACM, 61(5), 90-99. 2018.
Sears, et al. Expectations for tonal cadences: Sensory and cognitive priming effects. Quarterly Journal of Experimental Psychology, 72(6). 2019.
Serrà, et al. Measuring the Evolution of Contemporary Western Popular Music. 2012.
Shifriss, et al. When you're down and troubled: Views on the regulatory power of music. Psychology of Music, 43(6). 2015.
Silva, et al. Domain-Specific Expectations in Music Segmentation. Brain Sciences, 9(7), 169. 2019.
Silvia, et al. On personality and piloerection: Individual differences in aesthetic chills and other unusual aesthetic experiences. Psychology of Aesthetics, Creativity, and the Arts, 5(3), 208-214. 2011.
Singer, et al. Common modulation of limbic network activation underlies musical emotions as they unfold. NeuroImage, 141. 2016.
Sloboda, et al. Music Structure and Emotional Response: Some Empirical Findings. In Psychology of Music (vol. 19, Issue 2, pp. 110-120). 1991.
Smolen, et al. The Effect of Self-Selected Music during Colonoscopy on Anxiety, Heart Rate, and Blood Pressure. Applied Nursing Research, 15(3), 126-136. 2002.
Son, et al. The effects of self-selected music on anxiety and pain during burn dressing changes. Taehan Kanho Hakhoe Chi, 36(1), 159-168. 2006.
Sridharan, et al. A critical role for the right fronto-insular cortex in switching between central-executive and default-mode networks. Proceedings of the National Academy of Sciences of the United States of America, 105(34), 12569-12574. 2008.
Sridharan, et al. Neural Dynamics of Event Segmentation in Music: Converging Evidence for Dissociable Ventral and Dorsal Networks. Neuron, 55(3), 521-532. 2007.
Srinivasa Murthy, et al. Content-based music information retrieval (CB-MIR) and its applications toward the music industry: A review ACM Computing Surveys, 51(3). 2018.
Starr. Music therapy in hospice care. In American Journal of Hospice and Palliative Medicine (vol. 16, Issue 6, pp. 739-742). 1999.
Štillová, et al. Mozart effect in epilepsy: Why is Mozart better than Haydn? Acoustic qualities-based analysis of stereoelectroencephalography. European Journal of Neurology, 28(5), 1463-1469. 2021.
Strehlow. The use of music therapy in treating sexually abused children? Nordic Journal of Music Therapy, 18(2), 167-183. 2009.
Sun, et al. Tension Experience Induced by Nested Structures In Music. Frontiers in Human Neuroscience, 14. 2020.
Supplemental Material for Universals and Variations in Musical Preferences: A Study of Preferential Reactions to Western Music in 53 Countries. Journal of Personality and Social Psychology. 2022.
Tai, et al. Neural entrainment to the beat: The "missing-pulse" phenomenon. Journal of Neuroscience, 37(26), 6331-6341. 2017.
Tang, et al. Effects of music therapy on depression: A meta-analysis of randomized controlled trials. PLoS ONE, 15 (11) Nov. 2020.
Teixeira Borges, et al. Scaling behaviour in music and cortical dynamics interplay to mediate music listening pleasure. Scientific Reports, 9(1). 2019.
The Effects of Music Therapy by Self-Selected Music Listening on Terminal Cancer Patients' Affect and Stress by Pain Level—The Korean Journal of Hospice and Palliative Care | Korea Science, (n.d.). Retrieved Oct. 14, 2020. url: <https://www.koreascience.or.kr/article/JAKO2012174498884>.
The relationship between valence and chills in music: A corpus analysis | Rémi de Fleurian. (n.d.). Retrieved Nov. 24, 2020. url: <https://remidefleurian.com/publication/2020-psyarxiv-val/>.
Thoma, et al. Emotion regulation through listening to music in everyday situations. Cognition and Emotion, 26(3), 550-560. 2012.
Thoma, et al. Listening to music and physiological and psychological functioning: the mediating role of emotion regulation and stress reactivity. Psychology & Health, 27(2), 227-241. 2012.
Tirovolas, et al. Music Perception and Cognition Research from 1983 to 2010: A Categorical and Bibliometric Analysis of Empirical Articles in Music Perception. Music Perception, 29(1), 23-36. 2011.
Trainor, et al. Explaining the high voice superiority effect in polyphonic music: Evidence from cortical evoked potentials and peripheral auditory models. Hearing Research, 308, 60-70. 2014.
Trappe, et al. The Cardiovascular Effect of Musical Genres. Deutsches Arzteblatt International, 113(20), 347-352. 2016.
Trost, et al. Temporal dynamics of musical emotions examined through intersubject synchrony of brain activity. Social Cognitive and Affective Neuroscience, 10(12). 2014.

(56) References Cited

OTHER PUBLICATIONS

Tseng. Electrophysiological correlation underlying the effects of music preference on the prefrontal cortex using a brain-computer interface. Sensors, 21(6), 1-13. 2021.
Turnbull, et al. Semantic Annotation and Retrieval of Music and Sound Effects. IEEE Transactions on Audio, Speech, and Language Processing, 16(2), 467. 2008.
Tzanetakis, G., & Cook, P. (n.d.). Multifeature Audio Segmentation for Browsing and Annotation. Retrieved Feb. 4, 2021. url: <http://www.cs.princeton.edu/>.
Vempala, et al. Music of the 7Ts: Predicting and Decoding Multivoxel fMRI Responses with Acoustic, Schematic, and Categorical Music Features. Front. Psychol, 8, 1179. 2017.
Vines, et al. Analyzing Temporal Dynamics in Music: Differential Calculus, Physics, and Functional Data Analysis Techniques. Music Perception, 137-152. 2005.
Vogt, et al. Automatic Recognition of Emotions from Speech: A Review of the Literature and Recommendations for Practical Realisation. Lecture Notes in Computer Science (Including Subseries Lecture Notes in Artificial Intelligence and Lecture Notes in Bioinformatics), 4868 LNCS, 75-91. 2008.
Vuoskoski, et al. The pleasure evoked by sad music is mediated by feelings of being moved. Frontiers in Psychology, Mar. 8, 2017.
Wallmark, et al. Neurophysiological Effects of Trait Empathy in Music Listening. Frontiers in Behavioral Neuroscience, 12, 66. 2018.
Wassiliwizky, et al. Art-elicited chills indicate states of being moved. Psychology of Aesthetics, Creativity, and the Arts, 9(4), 405-416. 2015.
Wassiliwizky, et al. Tears falling on goosebumps: Co-occurrence of emotional lacrimation and emotional piloerection indicates a psychophysiological climax in emotional arousal. Frontiers in Psychology, Feb. 8, 2017.
Wesseldijk, et al. Does listening to music increase your ability to discriminate musical sounds? Personality and Individual Differences, 161. 2020.
Weth, et al. Ambivalent Emotions in Music☐: We Like Sad Music When It Makes Us Happy. Proceedings of the 3rd International Conference on Music & Emotion (ICME3). 2013.
White, et al. Emotion response and regulation to "happy" and "sad" music stimuli: Partial synchronization of subjective and physiological responses. Musicae Scientiae, 20(1). 2016.
Xing, et al. Exposure to Mozart music reduces cognitive impairment in pilocarpine-induced status epilepticus rats. Cognitive Neurodynamics, 10(1), 23-30. 2016.
Xu, et al. Long-term music adjuvant therapy enhances the efficacy of sub-dose antiepileptic drugs in temporal lobe epilepsy. CNS Neuroscience & Therapeutics, cns.13623. 2021.
Zacharakis, et al. Conceptual blending in music cadences: A formal model and subjective evaluation. Proceedings of the 16th International Society for Music Information Retrieval Conference, ISMIR 2015.
Zatorre. Music, the food of neuroscience? In Nature (vol. 434, Issue 7031, pp. 312-315). 2005.
Zhou, et al. Music-induced emotions influence intertemporal decision making. 1995331, 1-19. 2021.
Gingras, et al. The Eye is Listening: Music-Induced Arousal and Individual Differences Predict Pupillary Responses. Frontiers in Human Neuroscience, 9. 2015.
Gold, et al. Predictability and uncertainty in the pleasure of music☐: a reward for learning☐? J Neurosci, Oct. 2019.
Goldstein. Thrills in response to music and other stimuli. Physiological Psychology, 8(1), 126-129. 1980.
Gosling, et al. A very brief measure of the Big-Five personality domains. Journal of Research in Personality, 37(6), 504-528. 2003.
Greenberg, et al. Universals and variations in musical preferences: A study of preferential reactions to Western music in 53 countries. Journal of Personality and Social Psychology, 122(2), 286. 2022.
Grekow. From Content-based Music Emotion Recognition to Emotion Maps of Musical Pieces. http://www.springer.com/series/7092. 2018.
Grewe, et al. Chills in different sensory domains: Frisson elicited by acoustical, visual, tactile and gustatory stimuli. Psychology of Music, 39(2), 220-239. 2011.
Grewe, et al. How Does Music Arouse "Chills"? Investigating strong emotions, combining psychological, physiological, and psychoacoustical methods Annals of the New York Academy of Sciences, 1060, 446-449. 2005.
Grewe, et al. Listening to Music as a Re-Creative Process: Physiological, Psychological, and Psychoacoustical Correlates of Chills and Strong Emotions. Music Perception: An Interdisciplinary Journal, 24(3), 297-314. 2007.
Grewe, et al. Listening to Music as a Re-Creative Process: Physiological, Psychological, and Psychoacoustical Correlates of Chills and Strong Emotions. DMRN+13: Digital Music Research Network. 2018.
Groarke, et al. Listening to self-chosen music regulates induced negative affect for both younger and older adults. PLoS ONE, 14(6). 2019.
Guhn, et al. Physiological and Musico-Acoustic Correlates of the Chill Response. Music Perception, 24(5), 473-483. 2007.
Hanke, et al. A high-resolution 7-Tesla fMRI dataset from complex natural stimulation with an audio movie. Scientific Data, 1, 1-18. 2014.
Harrison, et al. Thrills, chills, frissons, and skin orgasms: Toward an integrative model of transcendent osychophysiological experiences in music. Frontiers in Psychology, Jul. 5, 2014.
Harvey. Politics and Power in the Record Industry: The Beatles, the Beach Boys, and the Album as Art Form. Musicology Australia, 38(2), 153-171. 2016.
Hausmann, et al. Music-induced changes in functional cerebral asymmetries. Brain and Cognition, 104, 58-71. 2016.
Hoefle, et al. Identifying musical pieces from fMRI data using encoding and decoding models. Scientific Reports, 8(1), 1-13. 2018.
Höller, et al. Individual brain-frequency responses to self-selected music. International Journal of Psychophysiology, 86 (3), 206-213. 2012.
Huron, et al. On the Enjoyment of Sad Music: Pleasurable Compassion Theory and the Role of Trait Empathy. Frontiers in Psychology, 11, 1060. 2020.
Huron. Musical Aesthetics: Uncertainty and Surprise Enhance Our Enjoyment of Music. In Current Biology (vol. 29, Issue 23, pp. R1238-R1240). Cell Press. 2019.
Huron. Sweet Anticipation: Music and the Psychology of Expectation. MIT Press. 2006.
Jacoby, et al. Universal and Non-universal Features of Musical Pitch Perception Revealed by Singing. Current Biology, 29(19), 3229-3243.e12. 2019.
James. The physical basis of emotion. Psychological Review, 10(2), 205-210. 1893.
Janata, et al. Psychological and musical factors underiying engagement with unfamiliar music. Music Perception, 36 (2), 175-200. 2018.
John, et al. The Big-Five Trait Taxonomy: History, Measurement, and Theoretical Perspectives. In L. A. Pervin & O. P. John (Eds.), Handbook of personality: Theory and research (vol. 8, Issue 2, pp. 102-138). Guilford Press. 1999.
Johnston, et al. 'Playlist for Life' at the end of life: a mixed-methods feasibility study of a personalised music listening intervention in the hospice setting. Pilot and Feasibility Studies, 8(1), 1-14. 2022.
Juslin, et al. Expression, Perception, and Induction of Musical Emotions: A Review and a Questionnaire Study of Everyday Listening. Journal of New Music Research, 33(3), 217-238. 2004.
Kaneshiro, et al. Natural music evokes correlated EEG responses reflecting temporal structure and beat. NeuroImage, 116559. 2020.
Karageorghis, et al. Music in the exercise domain: a review and synthesis (Part I). In International Review of Sport and Exercise Psychology (vol. 5, Issue 1, pp. 44-66). 2012.
Katahira, et al. Volitional Control of Piloerection: Objective Evidence and Its Potential Utility in Neuroscience Research. Frontiers in Neuroscience, 14. 2020.

(56) References Cited

OTHER PUBLICATIONS

Klepzig, et al. Brain imaging of chill reactions to pleasant and unpleasant sounds. Behavioural Brain Research, 380. 2020.
Koelsch, et al. Neocortical substrates of feelings evoked with music in the ACC, insula, and somatosensory cortex. Scientific Reports, 11(1), 1-12. 2021.
Koelsch. A coordinate-based meta-analysis of music-evoked emotions. NeuroImage, 223. 2020.
Koelsch. Investigating the Neural Encoding of Emotion with Music. Neuron, 98(6), 1075-1079. 2018.
Konečni, et al. Emotional and aesthetic antecedents and consequences of music-induced thrills. American Journal of Psychology, 120(4), 619-643. 2007.
Koulis, et al. From zero to sixty: Calibrating real-time responses. Psychometrika, 73(2), 321-339. 2008.
Kühn, et al. The neural correlates of subjective pleasantness. NeuroImage, 61(1), 289-294. 2012.
Lange, et al. Challenges and opportunities of predicting musical emotions with perceptual and automatized features. Music Perception, 36(2), 217-242. 2018.
Lartillot, et al. Data Analysis, Machine Learning and Applications. Jan. 2008.
Leeuwis, et al. A Sound Prediction: EEG-Based Neural Synchrony Predicts Online Music Streams. Frontiers in Psychology, Jul. 2021.
Lehne, et al. Tension-related activity in the orbitofrontal cortex and amygdala: An fMRI study with music. Social Cognitive and Affective Neuroscience, 9(10). 2013.
Levinson. Musical Chills. In Contemplating Art: Essays in Aesthetics. Oxford Scholarship Online. 2007.
Levitin, et al. Current Advances in the Cognitive Neuroscience of Music. Annals of the New York Academy of Sciences, 1156(1), 211-231. 2009.
Levitin, et al. Introduction to functional data analysis. Canadian Psychology, 48(3), 135-155. 2007.
Levitin, et al. Musical rhythm spectra from Bach to Joplin obey a 1/f power law. Proceedings of the National Academy of Sciences of the United States of America, 109(10), 3716-3720. 2012.
Lewin. Special Cases of the Interval Function between Pitch-Class Sets X and Y. Journal of Music Theory, 45(1), 1. 2001.
Li, et al. Listening to music in a risk-reward context: The roles of the temporoparietal junction and the orbitofrontal/insular cortices in reward-anticipation, reward-gain, and reward-loss. Brain Research, 1629. 2015.
Lin, et al. Early evaluation of the therapeutic effectiveness in children with epilepsy by quantitative EEG: A model of Mozart K.448 listening—a preliminary study. Epilepsy Research, 108(8), 1417-1426. 2014.
Lin, et al. Increasing fMRI Sampling Rate Improves Granger Causality Estimates. PLoS ONE, 9(6), e100319. 2014.
Lin, et al. Mozart K.448 acts as a potential add-on therapy in children with refractory epilepsy. Epilepsy and Behavior, 20(3), 490-493. 2011.
Liu, et al. Spatial Connectivity and Temporal Dynamic Functional Network Connectivity of Musical Emotions Evoked by Dynamically Changing Tempo. Frontiers in Neuroscience, 0, 940. 2021.
Lloyd. The Musical Structure of Time in the Brain: Repetition, Rhythm, and Harmony in fMRI During Rest and Passive Movie Viewing Frontiers in Computational Neuroscience, 13, 98. 2020.
Lochte, et al. An fMRI investigation of the neural correlates underlying the autonomous sensory meridian response (ASMR). BioImpacts, 8(4), 295-304. 2018.
Locsin. The effect of music on the pain of selected post-operative patients. Journal of Advanced Nursing, 6(1), 19-25. 1981.
Lumaca, et al. Weighting of neural prediction error by rhythmic complexity: A predictive coding account using mismatch negativity. European Journal of Neuroscience, 49(12), 1597-1609. 2019.
Madison, et al. Repeated listening increases the liking for music regardless of its complexity: Implications for the appreciation and aesthetics of music. Frontiers in Neuroscience, Mar. 2017.
Mallik, et al. Anhedonia to music and mu-opioids: Evidence from the administration of naltrexone. Scientific Reports, 7, 41952. 2017.
Martinez-Molina, et al. Resting-State Network. 2021.
Maruskin, et al. The chills as a psychological construct: Content universe, factor structure, affective composition, elicitors, trait antecedents, and consequences. Journal of Personality and Social Psychology, 103(1), 135-157. 2012.
Mas-Herrero, et al. Common and distinct neural correlates of music and food-induced pleasure: A coordinate-based meta-analysis of neuroimaging studies. In Neuroscience and Biobehavioral Reviews (vol. 123, pp. 61-71). Elsevier Ltd. 2021.
Matthews, et al. The sensation of groove engages motor and reward networks. NeuroImage, 214, 116768. 2020.
McDermott, et al. Individual differences reveal the basis of consonance. Current Biology□: CB, 20(11), 1035-1041. 2010.
Mcmullen, et al. Music and Language: A Developmental Comparison. Music Perception, 21(3), 289-311. 2004.
Menninghaus, et al. Towards a psychological construct of being moved. PLoS ONE, 10(6). 2015.
Menon, et al. The rewards of music listening: Response and physiological connectivity of the mesolimbic system. NeuroImage, 28(1), 175-184. 2005.
Merrill, et al. Locus of emotion influences psychophysiological reactions to music. Plos One, 15(8), e0237641. 2020.
Miles, et al. A statistical analysis of the relationship between harmonic surprise and preference in popular music. Frontiers in Human Neuroscience, 11 (May), 1-13. 2017.
Miles, et al. What to Expect When the Unexpected Becomes Expected: Harmonic Surprise and Preference Over Time in Popular Music. Frontiers in Human Neuroscience, Apr. 15, 2021.
Morgan, et al. Statistical learning and Gestalt-like principles predict melodic expectations. Cognition, 189, 23-34. 2019.
Mori, et al. Two types of peak emotional responses to music: The psychophysiology of chills and tears. Scientific Reports, 7. 2017.
MRC Data's 2021 U.S. Year-End Report—MRC Data Reports. Retrieved Feb. 9, 2022. url: <https://mrcdatareports.com/mrc-data-2021-u-s-year-end-report/>.
Müller, et al. Signal Processing for Music Analysis. IEEE Journal of Selected Topics in Signal Processing, 0(0), 1. 2011.
Musical "Chills" among Topics of Music Therapy Symposium | Berklee College of Music, (n.d.). Retrieved Oct. 14, 2020. url: <https://www.berklee.edu/berklee-today/berklee-today-spring-2002/musical-"chills"-among-topics-music-therapy-symposium>.
Nagel, et al. Psychoacoustical correlates of musically induced chills. Musicae Scientiae, 12(1), 101-113. 2008.
Nemati, et al. Lost in music: Neural signature of pleasure and its role in modulating attentional resources. Brain Research, 1711, 7-15. 2019.
Noll-Hussong, et al. Tears Falling on Goosebumps: Co-occurrence of Emotional Lacrimation and Emotional Piloerection Indicates a Psychophysiological Climax in Emotional Arousal. Frontiers in Psychology. 8. 2017.
Núñez, et al. What happened to cognitive science? Nature Human Behaviour, 3(8), 782-791. 2019.
Nusbaum, et al. Shivers and timbres: Personality and the experience of chills from music. Social Psychological and Personality Science. 2011.
Obleser, et al. Neural Entrainment and Attentional Selection in the Listening Brain. Trends in Cognitive Sciences, 23 (11), 913-926. 2019.
Ooishi, et al. Increase in salivary oxytocin and decrease in salivary cortisol after listening to relaxing slow-tempo and exciting fast-tempo music. PLoS ONE, 12(12). 2017.
Pando-Naude, et al. Functional connectivity of music-induced analgesia in fibromyalgia. Scientific Reports, 9(1), 1-17. 2019.
Panksepp, et al. Emotional sounds and the brain: The neuro-affective foundations of musical appreciation. Behavioural Processes, 60(2), 133-155. 2002.
Panksepp. The Emotional Sources of "Chills" Induced by Music. Music Perception: An Interdisciplinary Journal, 13(2), 171-207. 1995.

(56) References Cited

OTHER PUBLICATIONS

Park, et al. Differences between musicians and non-musicians in neuro-affective processing of sadness and fear expressed in music. Neuroscience Letters, 566C, 120-124. 2014.
Parker, et al. Positive and Negative Hedonic Contrast With Musical Stimuli. Psychology of Aesthetics, Creativity, and the Arts, 2(3), 171-174. 2008.
Parncutt. The Tonic as Triad: Key Profiles as Pitch Salience Profiles of Tonic Triads. Music Perception: An Interdisciplinary Journal, 28(4), 333-366. 2011.
Paul. Using verbal reports to investigate children's aesthetic experiences with music. Journal of Music Therapy, 45(4). 2008.
Pearce. Statistical learning and probabilistic prediction in music cognition: Mechanisms of stylistic enculturation. Annals of the New York Academy of Sciences, 1423(1), 378-395. 2018.
Pereira, et al. Music and Emotions in the Brain: Familiarity Matters. PLoS ONE, 6(11), e27241. 2011.
Peretz, et al. Brain organization for music processing. Annual Review of Psychology, 56, 89-114. 2005.
Popescu, et al. Western listeners detect boundary hierarchy in Indian music: a segmentation study. Music Perception: An Interdisciplinary Journal, 17(1), 43-64. 1999.
PsyArXiv Preprints | Chills in music: An integrative review, (n.d.). Retrieved Nov. 24, 2020. url: <https://psyarxiv.com/yc6d8/>.
Quinn. A Unified Theory of Chord Quality in Equal Temperaments. 122. 2004.
Quiroga-Martinez, et al. Decomposing neural responses to melodic surprise in musicians and non-musicians: Evidence for a hierarchy of predictions in the auditory system. NeuroImage, 215. 2020.
Ramos, et al. Sleep and neurocognitive decline in the Hispanic Community Health Study/Study of Latinos. Alzheimer's and Dementia, 16(2), 305-315. 2020.
Randall, et al. Similarity measures for tonal models. In R. C. Mario Baroni, Anna Rita Addessi & Marco Costa (Eds.), 9th International Conference on Music Perception and Cognition: Perception II (p. 255). 2006.
Rentfrow, et al. The structure of musical preferences: A five-factor model. Journal of Personality and Social Psychology, 100(6), 1139-1157. 2011.
Researchers Just Compiled the Ultimate Playlist of Songs That Will Give You Chills | Inc.com. (n.d.). Retrieved Nov. 2, 2021. url: <https://www.inc.com/jessica-stillman/music-mood-happiness-focus.html>.
Roberts, et al. A mixed-methods examination of autonomous sensory meridian response: Comparison to frisson. Consciousness and Cognition, 86, 103046. 2020.
A mixed-methods examination of autonomous sensory meridian response: Comparison to frisson—ScienceDirect. (n.d.). Retrieved Mar. 22, 2021. url: <https://www.sciencedirect.com/science/article/abs/pii/S1053810020305134?via%3Dihub>.
A Spotify playlist with 715 songs known to give people chills—Quartz, (n.d.). Retrieved Nov. 2, 2021. url: <https://qz.com/2071652/a-spotify-playlist-with-715-songs-known-to-give-people-chills/>.
Albouy, et al. Distinct sensitivity to spectrotemporal modulation supports brain asymmetry for speech and melody. Science, 367(6481), 1043-1047. 2020.
Alluri, V., et al. Large-scale brain networks emerge from dynamic processing of musical timbre, key and rhythm. NeuroImage, 59(4), 3677-3689. 2012.
Anderson, et al. "Just the Way You Are": Linking Music Listening on Spotify and Personality. Social Psychological and Personality Science, 12(4), 561-572. 2021.
Atasoy, et al. Human brain networks function in connectome-specific harmonic waves. Nature Communications, 7. 2016.
Bannister, et al. Suppressing the chills: Effects of musical manipulation on the chills response. Frontiers in Psychology, 9(OCT). 2018.
Bannister. Distinct varieties of aesthetic chills in response to multimedia. Plos One, 14(11), e0224974. 2019.
Bannister. A survey into the experience of musically induced chills: Emotions, situations and music. Psychology of Music, 48(2), 297-314. 2020.
Bannister. A Vigilance Explanation of Musical Chills? Effects of Loudness and Brightness Manipulations. Music & Science, 3, 205920432091565. 2020.
Bartlett. Effect of repeated listenings on structural discrimination and affective response. Journal of Research in Music Education, 21(4), 302-317. 1973.
Batt-Rawden. The benefits of self-selected music on health and well-being. Arts in Psychotherapy, 37(4), 301-310. 2010.
Beier, et al. Do You Chill When I Chill? A Cross-Cultural Study of Strong Emotional Responses to Music. Psychology of Aesthetics, Creativity, and the Arts. 2020.
Benedek, et al. Objective and continuous measurement of piloerection. Psychophysiology, 47(5), 989-993. 2010.
Benedek, et al. Physiological correlates and emotional specificity of human piloerection. Biological Psychology, 86(3), 320-329. 2011.
Bezdek, et al. The effect of visual and musical suspense on brain activation and memory during naturalistic viewing. Biological Psychology, 129. 2017.
Big Five Inventory (BFI). 51(4), 65-66. 1998.
Bigliassi, et al. Cerebral effects of music during isometric exercise: An fMRI study. International Journal of Psychophysiology, 133(Jul.), 131-139. 2018.
Blood, et al. Emotional responses to pleasant and unpleasant music correlate with activity in paralimbic brain regions. Nature Neuroscience, 2(4), 382-387. 1999.
Blood, et al. Intensely pleasurable responses to music correlate with activity in brain regions implicated in reward and emotion. Proceedings of the National Academy of Sciences of the United States of America, 98(20), 11818-11823. 2001.
Burgoyne, et al. An expert ground-truth set for audio chord recognition and music analysis. Proceedings of the 12th International Society for Music Information Retrieval Conference, ISMIR 2011, Ismir, 633-638. 2011.
Chabin, et al. Cortical Patterns of Pleasurable Musical Chills Revealed by High-Density EEG. Frontiers in Neuroscience, 14, 1114. 2020.
Cheung, et al. Uncertainty and Surprise Jointly Predict Musical Pleasure and Amygdala , Hippocampus , and Auditory Cortex Activity. Current. 2019.
Clynes, et al. Music, Mind, and Brain: The Neuropsychology of Music (book review). Acoustical Society of America Journal, 75, 1308-1309. 1984.
Colver, et al. Getting aesthetic chills from music: The connection between openness to experience and frisson. Psychology of Music. 2015.
Corrêa, et al. A survey on symbolic data-based music genre classification. In Expert Systems with Applications (vol. 30, pp. 190-210). Elsevier Ltd. 2016.
Cowen, et al. What music makes us feel: At least 13 dimensions organize subjective experiences associated with music across different cultures. Proceedings of the National Academy of Sciences of the United States of America, 117 (4), 1924-193. 2020.
Craig. An Exploratory Study of Physiological Changes during "Chills" Induced by Music. Musicae Scientiae, 9(2), 273-287. 2005.
Daly, et al. Neural and physiological data from participants listening to affective music. Scientific Data, 7(1), 1-7. 2020.
De Fleurian, et al. Chills in music: An integrative review. 2020.
De Fleurian, et al. Effects of stimulus properties, stylistic preference and familiarity on musical chills. Conference poster—Queen Mary University of London. 2019.
De Fleurian, et al. The Relationship Between Valence and Chills in Music: A Corpus Analysis. 12(4), 1-11. 2021.
De Rosis, et al. From Greta's mind to her face: Modelling the dynamics of affective states in a conversational embodied agent. International Journal of Human Computer Studies, 59(1-2), 81-118. 2003.
De Witte, et al. Effects of music interventions on stress-related outcomes: a systematic review and two meta-analyses. Health Psychology Review, 14(2), 294-324. 2020.

(56) References Cited

OTHER PUBLICATIONS

Dunbar, et al. Cochlear SGN neurons elevate pain thresholds in response to music. Scientific Reports, 1-8. 2021.

Ebishima, et al. Relationship of the Acoustic Startle Response and Its Modulation to Adaptive and Maladaptive Behaviors in Typically Developing Children and Those With Autism Spectrum Disorders: A Pilot Study. 2019.

Eerola, et al. An integrative review of the enjoyment of sadness associated with music. Physics of Life Reviews, 25, 100-121. 2018.

Eerola. Are the Emotions Expressed in Music Genre-specific? An Audio-based Evaluation of Datasets Spanning Classical, Film, Pop and Mixed Genres Journal of New Music Research, 40(4), 349-366. 2011.

Færøvik, et al. Suppression, Maintenance, and Surprise: Neuronal Correlates of Predictive Processing Specialization for Musical Rhythm. Frontiers in Neuroscience, 0, 862. 2021.

Farris, et al. Musical Prosody-Driven Emotion Classification: Interpreting Vocalists Portrayal of Emotions Through Machine Learning. Proceedings of the 18th Sound and Music Computing Conference, Jun. 29-Jul. 1, 2021.

Fauvel, et al. Neural implementation of musical expertise and cognitive transfers: could they be promising in the framework of normal cognitive aging? Frontiers in Human Neuroscience, 7(Oct.), 693. 2013.

Forsthofer, et al. Frequency modulation of rattlesnake acoustic display affects acoustic distance perception in humans. 2021.

Forth, et al. Entraining IDyOT: Timing in the information dynamics of thinking. Frontiers in Psychology, 7(Oct). 2016.

Fredborg, et al. Mindfulness and autonomous sensory meridian response (ASMR). PeerJ, 6, e5414. 2018.

Freitas, et al. Neural correlates of familiarity in music listening: A systematic review and a neuroimaging meta-analysis. In Frontiers in Neuroscience (vol. 12, Issue Oct.). 2018.

Fricke, et al. Computer-based music feature analysis mirrors human perception and can be used to measure individual music preference. Journal of Research in Personality, 75, 94-102. 2018.

Fricke, et al. Measuring musical preferences from listening behavior: Data from one million people and 200,000 songs. Psychology of Music, 030573561986828. 2019.

Garrido, et al. Moody melodies: Do they cheer us up? A study of the effect of sad music on mood. Psychology of Music, 43(2). 2015.

Garrido, et al. Musical prescriptions for mood improvement: An experimental study. Arts in Psychotherapy, 51. 2016.

Garvija. On Musical Rewards: "Defrosting" musical chills with Naltrexone. 2019.

International Search Report and Written Opinion for PCT/US2022/033597, dated Sep. 23, 2022 (12 pages).

\* cited by examiner

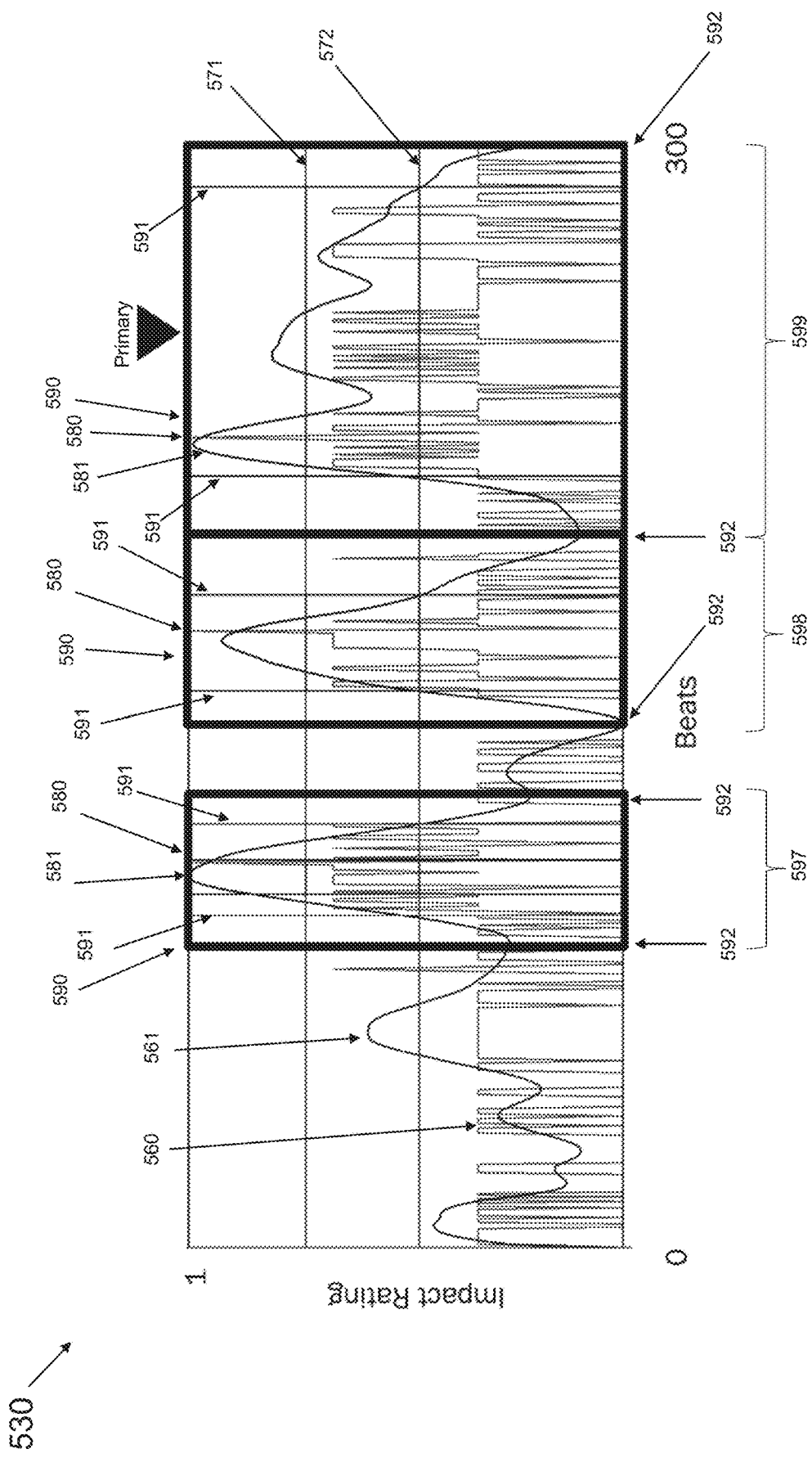

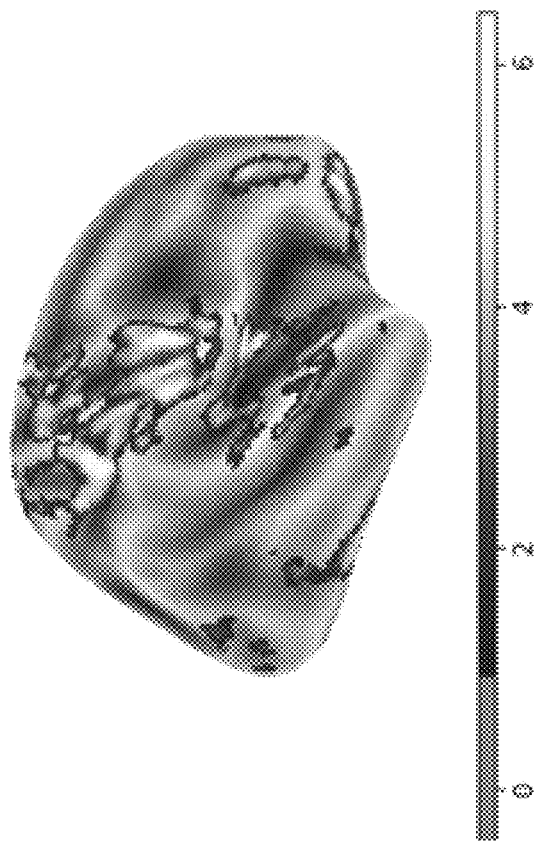
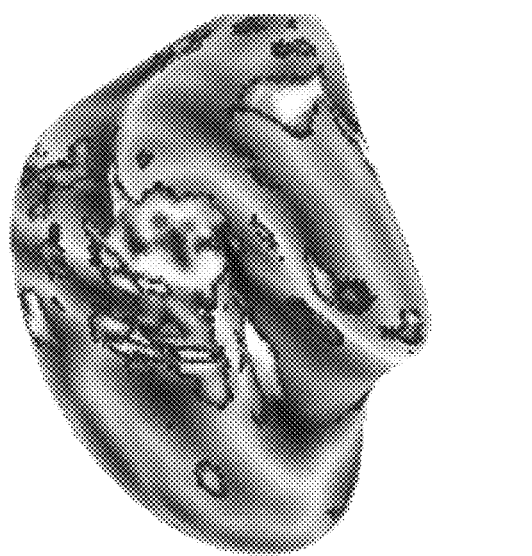
FIG. 10B

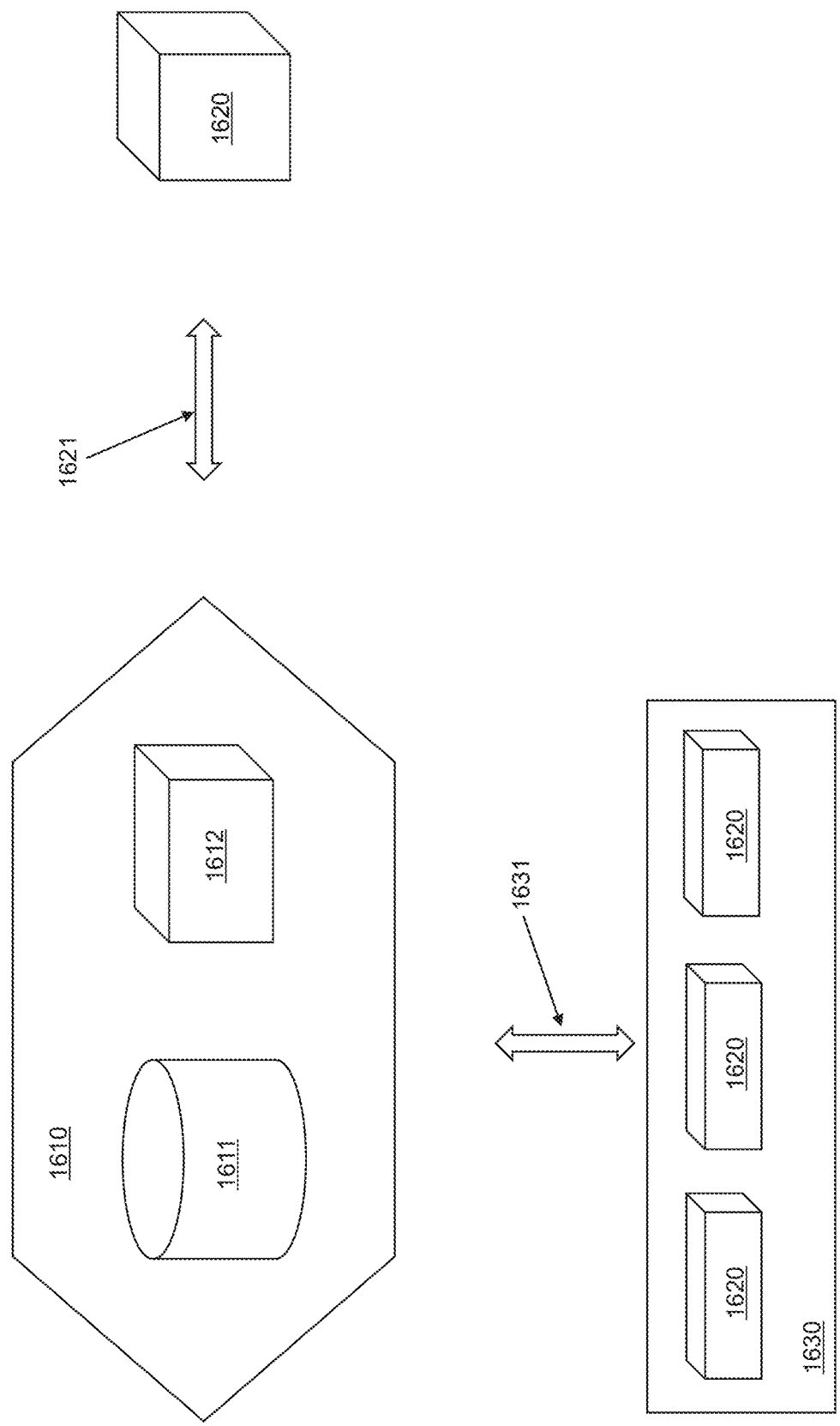

SYSTEMS AND METHODS FOR IDENTIFYING SEGMENTS OF MUSIC HAVING CHARACTERISTICS SUITABLE FOR INDUCING AUTONOMIC PHYSIOLOGICAL RESPONSES

CROSS-REFERENCE TO RELATED APPLICATIONS

This application claims priority to and the benefit of U.S. Provisional Application Ser. No. 63/210,863, entitled "SYSTEMS AND METHODS FOR IDENTIFYING SEGMENTS OF MUSIC HAVING CHARACTERISTICS SUITABLE FOR INDUCING AUTONOMIC PHYSIOLOGICAL RESPONSES," and filed Jun. 15, 2021, and also claims priority to and the benefit of U.S. Provisional Application Ser. No. 63/227,559, entitled "SYSTEMS AND METHODS FOR IDENTIFYING SEGMENTS OF MUSIC HAVING CHARACTERISTICS SUITABLE FOR INDUCING AUTONOMIC PHYSIOLOGICAL RESPONSES," and filed Jul. 30, 2021, the contents of each of which is incorporated by reference herein in their entirety.

FIELD

The present disclosure relates to systems and methods for processing complex audio data, such as music, and more particularly to systems and methods for processing music audio data to determine temporal regions of the audio data having the strongest characteristics suitable for inducing an autonomic physiological response in a human listener.

BACKGROUND

Recent scientific research has attempted to better understand the connection between auditory stimuli and autonomic physiological responses, such as the chills or goose bumps, which are well-known involuntary responses to certain sounds or music. In one of the first investigations into autonomic physiological responses to music, researchers collected data on cerebral blood flow, heart rate, respiration and electrical activity produced by skeletal muscles (e.g., electromyogram), as well as participants' subjective reports of 'chills.' This study determined that fluctuations in cerebral blood flow in brain regions associated with reward, emotion and arousal (e.g., ventral striatum, midbrain, amygdala, orbito-frontal cortex, and ventral medial prefrontal cortex) corresponded with the participants' self-reports of chills. These regions are also active in response to euphoria-inducing stimuli, such as food, sex and recreational drugs.

Accordingly, it has been established that there is a connection between music and autonomic physiological responses. However, there is a wide variety of genres, musical styles, and types of acoustic and musical stimuli that can produce a chills response. There is a need for digital audio processing routines that are capable of detecting the various individual root acoustic/musical structures within digital recordings tied to chills elicitation and evaluating the detected chills elicitors in a way that successfully accommodates the large variety of musical genres/styles in order to accurately identify specific segment or segments in a song or musical score that have the best chance of causing such an autonomic response.

SUMMARY

In the processes of creating software applications for use in selecting music segments for use in social media and advertising, selecting and curating sections of music by hand is a cost and time prohibitive task and efforts were undertaken to automate this process. One problem in curating large catalogs and identifying music segments involves various levels of aesthetic judgement, which are considered subjective. A new approach to this problem was to use methods from the field of Content-Based Music Information Retrieval (herein referred to as 'CB-MIR') combined with academic research from the field of neurological studies involving the idea of so-called 'chill responses' in humans (e.g., autonomic physiological responses), which are also strongly associated with the appreciation of music, even though chill moments are considered to be physiological in nature and are not necessarily subjective when considering the commonality of human sensory organs and human experience.

Existing techniques for finding these moments require subjective assessments by musical experts or people very familiar with any given piece of music. Even so, any individual will have a set of biases and variables that will inform their assessment as to the presence or likelihood of chills responses in the listening public at large. Examples of the present disclosure enable detection of music segments associated with eliciting the chills as an objective and quantitative process.

One aspect utilized by the present disclosure is the idea that musicians and composers use common tools to influence the emotional state of listeners. Volume contrasts, key changes, chord changes, melodic and harmonic pitches can all be used in this 'musician's toolbox' and are found in curriculum everywhere music performance and composition is taught. However, these high-level structures do not have explicit 'sonic signatures', or definitions in terms of signal processing of musical recordings. To find these structures, teachings from the field of CB-MIR, which focuses specifically on extracting low-level musical information from digitally recorded or streaming audio (e.g., feature extraction), are leveraged in a novel audio processing routine. Using the low-level information provided by traditional CB-MIR methods as a source, examples of the present disclosure include systems and methods for processing and analyzing complex audio data (e.g., music) to identify high-level acoustic and musical structures that have been found through neurological studies of music to produce chill responses.

Examples of this process begin by extracting a variety of CB-MIR data streams (also referring to herein as objective audio processing metrics) from a musical recording. Examples of these are loudness, pitch, spectrum, spectral flux, spectrum centroid, mel frequency cepstral coefficient and others, which are discussed in more details herein. The specific implementation of feature extraction for any given type of feature can have parameterization options that affect the preparing and optimizing of the data for subsequent processing steps. For example, the general feature of loudness can be extracted according to several varieties of filters and methodologies.

A subsequent phrase in the example process involves searching for the high-level chill-eliciting acoustic and musical structures. These structures have been described, to varying levels of specificity, in academic literature on chills phenomena. The detection of any one of these high-level structures from an individual CB-MIR data stream is referred to herein as a 'GLIPh,' as an acronym of Geometric Limbic Impact Phenomenon. More specifically, examples of the present disclosure include studying a chill elicitor as described in academic literature and then designing a GLIPh that represents the eliciting phenomenon as a statistical data pattern. GLIPhs can represent the moments of interest within each musical feature, such as pitch, loudness, and spectral flux. As various GLIPhs are identified that can be contained in an extracted feature dataset, boundaries can be drawn around the regions of interest (ROIs) within graphical plots, indicating where the GLIPhs are located within the timeline of the digital recording.

Next, as instances of the timestamps of the GLIPhs accumulate across various extracted feature datasets, a new dataset can be formed that calculates the amount of concurrence and proximity of GLIPhs within the digital recording. This data processing is referred to herein as a combination algorithm and the output data is referred to herein as a 'chill moments' plot, which can include a moving average of the output in order to present a continuous and smoother presentation of the output of the combination algorithm, which can have significant variations in value on a per beat level (or whichever smallest time intervals are used for one of the input metrics), which can result in 'busy' data when analyzed visually—a moving average of this output can be more useful for visual analysis of the data, especially when trends in a song over more than one beat or tactus are more useful to be assessed. In some examples, the GLIPhs are weighted equally, but the combination algorithm can also be configured to generate chill moments data by attributing a weighted value to each GLIPh instance. Examples of the generation of the moving average include using a convolution of the chill moments plot with a Gaussian filter that can be, for example, across as few as 2 or 3 beats, or as many as 100 or more, and is thus variable in time, based on the lengths of beats in the song, which can be a dynamic value. Representative example lengths can range from 10 to 50 beats, including 30 beats, which is the length used for the data presented herein. Basing this smoothing on beats advantageously adapts the moving average to the content of the music.

The observed tendency within artists' construction of songs is that chill elicitors (e.g., musical features that increase the likelihood of inducing autonomic physiological responses) can be used both simultaneously (to some logical limit) and in sequence—this aligns with the chill moments plot reflecting the concurrence and proximity of GLIPhs. That is to say, the more often a section of a song (or the overall song itself) exhibits patterns of concurrence and proximity in music features known to be associated with autonomic physiological responses, the more likely the elicitation of chills in a listener will be. Overall, when two or more of these features align in time, the higher the level of arousal the musical moment will induce. Accordingly, certain examples of the present disclosure provide for methods of processing audio data to identify individual chill elicitors and construct a new data set of one or more peak moments in the audio data that maximize the likelihood of inducing autonomic physiological responses that is, at least partially, based on the rate and proximity of concurrences in the identified chill elicitors. Examples include further processing this new data set to identify musical segments and phrases that contain these peak moments and providing them as, for example, a new type of metadata that can be used along with the original audio data as timestamps indicating the peak moments or phrases used to create truncated segments from the original audio data that contain the peak moments or phrases.

Examples of the present disclosure can be used to process digital audio recordings which encode audio waveforms as a series of "sample" values; typically 44,100 samples per second are used with pulse-code modulation, where each sample captures the complex audio waveform every 22.676 microseconds. Those skilled in the art will appreciate that higher sampling rates are possible and would not meaningfully affect the data extraction techniques disclosed herein. Example digital audio file formats are MP3, WAV, and AIFF. Processing can begin with a digitally-recorded audio file and a plurality of subsequent processing algorithms are used to extract musical features and identify musical segments having the strongest chill moments. A music segment can be any subsection of a musical recording, usually between 10 and 60 seconds long. Example algorithms can be designed to find segments that begin and end coinciding with the beginning and end of phrases such as a chorus or verse.

The primary categories of digital musical recording analysis are:

(i) Time-domain: The analysis of frequencies contained in a digital recording with respect to time, (ii) Rhythm: Repeating periodic signal within the time-domain that humans perceive as separate beats, (iii) Frequency: Repeating periodic signal within the time-domain that humans perceive as single tones/notes, (iv) Amplitude: The strength of the sound energy at a given moment, and (v) Spectral Energy: The total amount of amplitude present across all frequencies in a song (or some other unit of time), perceived as timbre.

Autonomic physiological responses (e.g., chills) can be elicited by acoustic, musical, and emotional stimulus-driven properties. These properties include sudden changes in acoustic properties, high-level structural prediction, and emotional intensity. Recent investigations have attempted to determine what audio characteristics induce the chills. In this approach, researchers suggest that a chills experience involves mechanisms based on expectation, peak emotion, and being moved. However, significant shortcomings are identified in the reviewed literature, regarding research design, adequacy of experimental variables, measures of chills, terminology, and remaining gaps in knowledge. Also, the ability to experience chills is influenced by personality differences, especially 'openness to experience'. This means that chill-inducing moments for a given listener can be rare and difficult to predict, possibly in part due to differences in individual predispositions. While literature provides a number of useful connections between an acoustic medium (music) and a physical phenomenon (chills), the ability to identify specific musical segments having one or more of these characters is challenging, as the numerous musical and acoustic characteristics of chills-eliciting musical events lack strict definitions. Moreover, many of the musical and acoustic characteristics identified are best understood as a complex arrangement of musical and acoustic events that, taken as whole, may have only a subjectively identifiable characteristic. Accordingly, the existing literature considers the identification of peak chill-inducing moments in complex audio data (e.g., music) to be an unsolved problem.

Existing research presents chill elicitors in aesthetic-descriptive terms rather than numerical terms. Complex concepts such as "surprise harmonies" do not currently have any known mathematical descriptions. While typical CB-MIR feature extraction methods are low-level and objective, they can nevertheless be used as building blocks in examples of the present disclosure to begin to construct (and subsequently discover and identify) patterns that can accurately represent the high-level complex concepts, as demonstrated by examples of the present disclosure.

Examples of the present disclosure go beyond subjective identification and enable objective identification of exemplary patterns in audio signals corresponding to these events (e.g., GLIPhs). A number of different objective audio processing metrics can be calculated for use in this identification. These include loudness, loudness band ratio, critical band loudness, predominant pitch melodia, spectral flux, and spectrum centroid. However, no known individual objective metric is able to robustly identify chill moments across a wide variety of music, but examples of the present disclosure enable such a robust detection by combining multiple metrics in a manner to identify segments suitable for eliciting a chill response regardless of the overall characteristic of the music (e.g., genre, mood, or arrangement of instruments).

For example, during an analysis of a given digital recording, as instances of the timestamps of the GLIPhs accumulate across various extracted feature datasets, a new dataset can be formed using a combination algorithm based on the amount of concurrence and proximity of GLIPhs identified within the digital recording. This dataset is referred to herein as a chill moments plot and the combination algorithm generates a chill moments plot by attributing a weighted value to each GLIPh instance and determining their concurrent rate, for example, or per a unit of time (e.g., per beat or per second). One reason for combining a set of metrics (e.g., the metrics identifying individual GLIPhs) is that there are many types of chill elicitors. There is no single metric, in terms of standard CB-MIR-style feature extraction that can possibly encode all of the various acoustic and musical patterns that are known to be determinative of music segments having the characteristics suite to elicit chill moments (e.g., the chill-eliciting characteristics identified by research, such as by de Fleurian & Pearce). Moreover, recording artists employ many types of tools when constructing and recording music, and there is no single tool used within a given song generally and the wide variety of musical styles and genres have many different aesthetic approaches. The extreme diversity of popular music is strong evidence of this. Any single feature often has many points in a song. Melodic pitch, for example, will have potentially hundreds of points of interest in a song, each of which can correspond to an individual GLIPh in the song. It is only when looking at the co-occurrences of multiple GLIPh features aligning across multiple objective metrics that a coherent pattern emerges.

Music segments can be identified by examples of the present disclosure as primary and secondary chill segments based on, for example, their GLIPh concurrences. These concurrences will, when auditioned by an experimental trial participant, produce predictable changes in measures of behavior and physiology as detailed in the chills literature. Primary chill segments can be segments within an audio recording with the highest concurrence of GLIPhs and can indicate the segments most likely to produce the chills, and secondary chill segments are segments identified to be chill inducing to a lesser degree based on a lower concurrence of GLIPhs than the primary chill segment. Experiments were conducted that validated this prediction ability and those results are presented herein. These identified segments can be referred to as 'chill phrases' or 'chill moments', although because actual experiences of musical chills (e.g., inducements of an autonomic physiological response in a given listener) are infrequent, these segments can also be regarded as 'impactful musical phrases' or, generally, music segments having characteristics suitable for inducing autonomic physiological responses.

As discussed and illustrated in more detail herein, examples of the present disclosure can include a) analyzing synchronous data from five domains (time, pitch, rhythm, loudness, and spectrum) and b) identifying specific acoustical signatures with only a very general musical map as a starting position. Examples can output a series of vectors containing the feature data selected for inclusion into the chills-moment plot—along with a GLIPh meta-analysis for each feature. For example, the Loudness-per-beat data output can be saved as a vector of data, after which a threshold (or other detection algorithm) can be applied to determine GLIPh instances in the individual metric data (e.g., the upper quartile of the Loudness-per-beat data), which are saved with the start and stop times for each GLIPh segment of the data that falls within the upper quartile in two vectors—one to save the start times, another to save the end times. Afterwards, each feature can be analyzed and for each beat it can be determined if the feature's start and stop times of interest fall within this moment of time and, if it does, it is added to the value of the chill moment vector according to that feature's particular weighting.

The output is thus a collection of numerical values, strings, vectors of real numbers, and matrices of real numbers representing the various features under investigation. The chill moments output can be a sum of the features (e.g., individual objective audio metrics) denoting an impactful moment for each elicitor (e.g., an identified GLIPh or concurrence of GLIPhs) at each time step.

Examples of the present disclosure provide for the ability to find the most impactful moments from musical recordings, and the concurrence of chill eliciting acoustic and musical features is a predictor of listener arousal.

One example of the present disclosure is computer-implemented method of identifying segments in music, the method including receiving, via an input operated by a processor, digital music data, processing, using a processor, the digital music data using a first objective audio processing metric to generate a first output, processing, using a processor, the digital music data using a second objective audio processing metric to generate a second output, generating, using a processor, a first plurality of detection segments using a first detection routine based on regions in the first output where a first detection criteria is satisfied, generating, using a processor, a second plurality of detection segments using a second detection routine based on regions in the second output where a second detection criteria is satisfied, and combining, using a processor, the first plurality of detection segments and the second plurality of detection segments into a single plot representing concurrences of detection segments in the first and second pluralities of detection segments, where the first and second objective audio processing metrics are different. The method can include identifying a region in the single plot containing the highest number of concurrences during a predetermined minimum length of time requirement and outputting an indication of the identified region. The combining can include calculating a moving average of the single plot. The method can include identifying a region in the single plot where the moving average is above an upper bound and outputting an indication of the identified region. One or both of the first and second objective audio processing metrics can be first-order algorithms and/or are configured to output first-order data. Examples include the first and second objective audio processing metrics selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

Examples of the method can include applying a low-pass envelope to either output of the first or second objective audio processing metrics. The first or second detection criteria can include an upper or lower boundary threshold. The method can include applying a length requirement filter to eliminate detection segments outside of a desired length range. The combining can include applying a respective weight to first and second plurality of detection.

Another example of the present disclosure is a computer system, that includes an input module configured to receive a digital music data, an audio processing module configured to receive the digital music data and execute a first objective audio processing metric on the digital music data and a second objective audio processing metric on the digital music data, the first and second metrics generating respective first and second outputs, a detection module configured to receive, as inputs, the first and second outputs and, generate, for each of the first and second outputs, a set of one or more segments where a detection criteria is satisfied, and a combination module configured to receive, as inputs, the one or more segments detected by the detection module and aggregate each segment into a single dataset containing concurrences of the detections. The system can include a phrase identification module configured to receive, as input, the single dataset of concurrences from the combination module and identify one or more regions where the highest average value of the single dataset occur during a predetermined minimum length of time. The phrase identification module can be configured to identify the one or more regions based on where a moving average of the single dataset is above an upper bound. The phrase identification module can be configured to apply a length requirement filter to eliminate regions outside of a desired length range. The combination module can be configured to calculate a moving average of the single plot. One or both of the first and second objective audio processing metrics can be first-order algorithms and/or are configured to output first-order data.

The system can include the first and second objective audio processing metrics being selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes. The detection module can be configured to apply a low-pass envelope to either output of the first or second objective audio processing metrics. The detection criteria can include an upper or lower boundary threshold. The detection module can be configured to apply a length requirement filter to eliminate detection segments outside of a desired length range. The combination module can be configured to apply respective weights to the first and second plurality of detections before aggregating each detected segment based on the respective weight.

Yet another example of the present disclosure is a computer program product, including a tangible, non-transient computer usable medium having computer readable program code thereon, the computer readable program code including code configured to instruct a processor to: receive digital music data, process the digital music data using a first objective audio processing metric to generate a first output, process the digital music data using a second objective audio processing metric to generate a second output, generate a first plurality of detection segments using a first detection routine based on regions in the first output where a first detection criteria is satisfied, generate a second plurality of detection segments using a second detection routine based on regions in the second output where a second detection criteria is satisfied, and combine the first plurality of detection segments and the second plurality of detection segments into a single plot based on concurrences of detection segments in the first and second pluralities of detection segments, where the first and second objective audio processing metrics are different. The first and second objective audio processing metrics can be selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes. The computer program product can include instruction to identify a region in the single plot containing the highest number of concurrences during a predetermined minimum length of time requirement and output an indication of the identified region. The product can include instruction to identify one or more regions where the highest average value of the single dataset occurs during a predetermined minimum length of time. The product can include instruction to calculate a moving average of the single plot. The first or second detection criteria can include an upper or lower boundary threshold. The product can include instruction to apply a length requirement to filter to eliminate detection segments outside of a desired length range.

Still another example of the present disclosure is computer-implemented method of identifying segments in music having characteristics suitable for inducing autonomic psychological responses in human listeners that includes receiving, via an input operated by a processor, digital music data, processing, using a processor, the digital music data using two or more objective audio processing metrics to generate a respective two or more outputs, detecting, via a processor, a plurality of detection segments in each of the two or more outputs based on regions where a respective detection criteria is satisfied, and combining, using a processor, the plurality of detection segments in each of the two or more outputs into a single chill moments plot based on concurrences in the plurality of detection segments, where the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes. The method can include identifying, using a processor, one or more regions in the single chill moments plot containing the highest number of concurrences during a minimum length requirement, and outputting, using a processor, an indication of the identified one or more regions. Examples include displaying, via a display device, a visual indication of values of the single chill moments plot with respect to a length of the digital music data. Examples can include displaying, via a display device, a visual indication of the digital music data with respect to a length of the digital music data overlaid with a visual indication of values of the single chill moments plot with respect to the length of the digital music data. The visual indication of values of the single chill moments plot can include a curve of a moving average of the values of the single chill moments plot. Examples of the method include identifying a region in the single chill moments plot containing the highest number of concurrences during a predetermined minimum length of time requirement, and outputting an indication of the identified region. The outputting can include displaying, via a display device, a visual indication of the identified region.

The outputting can include displaying, via a display device, a visual indication of the digital music data with respect to a length of the digital music data overlaid with a visual indication of the identified region in the digital music data.

Still another example of the present disclosure is a computer-implemented method of providing information identifying impactful moments in music, the method including: receiving, via an input operated by a processor, a request for information relating to the impactful moments in a digital audio recording, the request containing an indication of the digital audio recording, accessing, using a processor, a database storing a plurality of identifications of different digital audio recordings and a corresponding set of information identifying impactful moments in each of the different digital audio recordings, the corresponding set including at least one of: a start and stop time of a chill phrase or values of a chill moments plot, matching, using a processor, the received identification of the digital audio recording to an identification of the plurality of identifications in the database, the matching including finding an exact match or a closest match, and outputting, using a processor, the set of information identifying impactful moments of the matched identification of the plurality of identifications in the database. The corresponding set of information identifying impactful moments in each of the different digital audio recordings can include information created using a single plot of detection concurrences for each of the different digital audio recordings generated using the method of example 1 for each of the different digital audio recordings. The corresponding set of information identifying impactful moments in each of the different digital audio recordings can include information created using a single chill moments plot for each of the different digital audio recordings generated using the method of example 29 for each of the different digital audio recordings.

Another example of the present disclosure is a computer-implemented method of displaying information identifying impactful moments in music, the method including: receiving, via an input operated by a processor, an indication of a digital audio recording, receiving, via a communication interface operated by a processor, information identifying impactful moments in the digital audio recording, the information include at least one of: a start and stop time of a chill phrase, or values of a chill moments plot, displaying, using a processor, the received identification of the digital audio recording to an identification of the plurality of identifications in the database, the matching including finding an exact match or a closest match, outputting, using a display device, a visual indication of the digital audio recording with respect to a length of time of the digital audio recording overlaid with a visual indication of the chill phrase and/or the values of the chill moment plot with respect to the length of time of the digital audio recording.

BRIEF DESCRIPTION OF DRAWINGS

This disclosure will be more fully understood from the following detailed description taken in conjunction with the accompanying drawings, in which:

FIG. 5E is an illustration of an example output of a combination algorithm based on the objective audio processing metrics of FIGS. 5B, 5C, and 5D overlaid with an output of a phrase detection algorithm applied to the output of the combination algorithm;

FIG. 10B is fMRI data showing a broad network of neural activations associated with increases during algorithm-identified peak moments in music, compared to non-peak moments;

FIG. 16 is a block diagram of one exemplary embodiment of a cloud-based computer network for use in conjunction with the present disclosures.

DETAILED DESCRIPTION

Figure 1A:
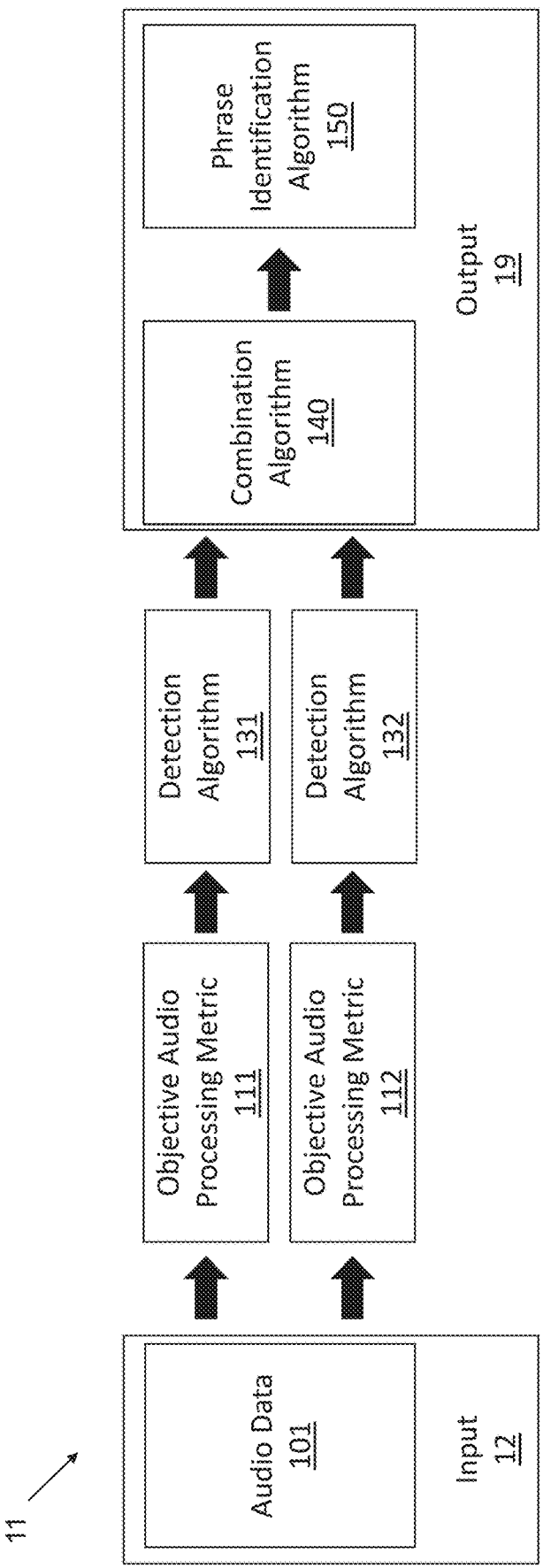
FIG. 1A is a flowchart of an example routine for processing digital music data according to the present disclosure.

Certain exemplary embodiments will now be described to provide an overall understanding of the principles of the structure, function, and use of the devices, systems, and methods disclosed herein. One or more examples of these embodiments are illustrated in the accompanying drawings. Those skilled in the art will understand that the devices, systems, and components related to, or otherwise part of, such devices, systems, and methods specifically described herein and illustrated in the accompanying drawings are non-limiting embodiments and that the scope of the present disclosure is defined solely by the claims. The features illustrated or described in connection with one embodiment may be combined with the features of other embodiments. Such modifications and variations are intended to be included within the scope of the present disclosure. Some of the embodiments provided for herein may be schematic drawings, including possibly some that are not labeled as such but will be understood by a person skilled in the art to be schematic in nature. They may not be to scale or may be somewhat crude renderings of the disclosed components. A person skilled in the art will understand how to implement these teachings and incorporate them into work systems, methods, and components related to each of the same, provided for herein.

To the extent the present disclosure includes various terms for components and/or processes of the disclosed devices, systems, methods, and the like, one skilled in the art, in view of the claims, present disclosure, and knowledge of the skilled person, will understand such terms are merely examples of such components and/or processes, and other components, designs, processes, and/or actions are possible. By way of non-limiting example, while the present application describes processing digital audio data, alternatively, or additionally, processing can occur through analogous analogue systems and methods or include both analogue and digital processing steps. In the present disclosure, like-numbered and like-lettered components of various embodiments generally have similar features when those components are of a similar nature and/or serve a similar purpose.

The present disclosure is related to processing complex audio data, such as music, to identify one or more moments in the complex audio data having the strongest characteristics suitable for inducing an autonomic physiological response in a human listener. However, alternative configurations are disclosed as well, such as the inverse (e.g., moments in complex audio data having the weakest characteristics suitable for inducing an autonomic physiological response in a human listener). Accordingly, one skilled in the art will appreciate that the audio processing routines disclosed herein are not limited to configuration based on characteristics suitable for inducing an autonomic physiological response in a human listener, but are broadly capable of identifying a wide range of complex audio characteristics depending on a number of configuration factors, such as: the individual metrics chosen, the thresholds used in each metric to determine positive GLIPh instances, and the weights applied to each metric when combining their concurrent GLIPh instances to generate an output (referred to here as a chill moments dataset, but this is reflective of the choice of individual metrics having known associations with the identification of various chill-elicitors in neuroscience research and thus, in examples where a set of metrics is chosen for identification of a different acoustic phenomena, a context-reflective name for the output would be chosen as well). Indeed, there may be, for example, correlations between music and biological responses that are not yet known in research, but examples of the present disclosure could be used to identify moments in any complex audio data most likely to induce the biological activity by combining individual objective acoustic characteristics that are associated with an increased likelihood of the biological activity.

Audio Processing

FIG. 1A is a flowchart of an example routine 11 for processing audio data 101 according to the present disclosure. In FIG. 1A, the routine 11 can begin with audio data 101, which can be digital audio data, such as music, and this audio data 101 can be received via an input 12. In a subsequent step, two or more objective audio processing algorithms 111, 112 (e.g., also referred to herein as metrics, audio metrics, or audio processing metrics) are executed on the audio data 101 to generate outputs representing the audio characteristics associated with the metrics 111, 112 (e.g., loudness, spectral energy). For each metric's output, a detection algorithm 131, 132 identifies one or more moments in the data where the metric's output is relatively elevated (e.g., above a quartile of the data) and outputs these detections as binary masks indicating positive and null detection regions in the time-domain of the originally input audio data 101 (e.g., if an input audio data 101 is 200 seconds long, then each binary mask can cover the same 200 seconds).

A combination algorithm 140 receives the input binary masks and aggregates them into a chill moments plot, which contains values in the time-domain of the concurrences of the aggregation. For example, if a moment in the audio data 101 returns positive detections in both metrics, then that moment is aggregated with a value of "2" for that time in the output of the combination algorithm 140. Likewise, if only one metric returns a positive detection for a moment, then the value is "1." The combination algorithm can normalize the output as well as provide a moving average, or any other data typical processing known to those of ordinary skill in the art. The combination algorithm 140 can be part of, or in connection with, an output 19 that can provide the output of the combination algorithm 140 to, for example, a storage device, or another processor. Additionally, the routine 11 can include a phrase identification algorithm 150 that takes, as an input, output data from the combination algorithm 140 and detects one or more segments of the audio data containing one or more peaks of the chill moments plot based on, for example, their relative strength and proximity to each other. The phrase identification algorithm 150 can be part of, or in connection with, an output 19 that can provide the output of the combination algorithm 140 to, for example, a storage device, or another processor. The phrase identification algorithm 150 can output any data associated with the identified segments, including timestamps, as well as a detection of a primary segment based on a comparison of all identified segments. The phrase identification algorithm 150 can create and output segments of the original audio data 101 that represent the identified segments.

Figure 1B:
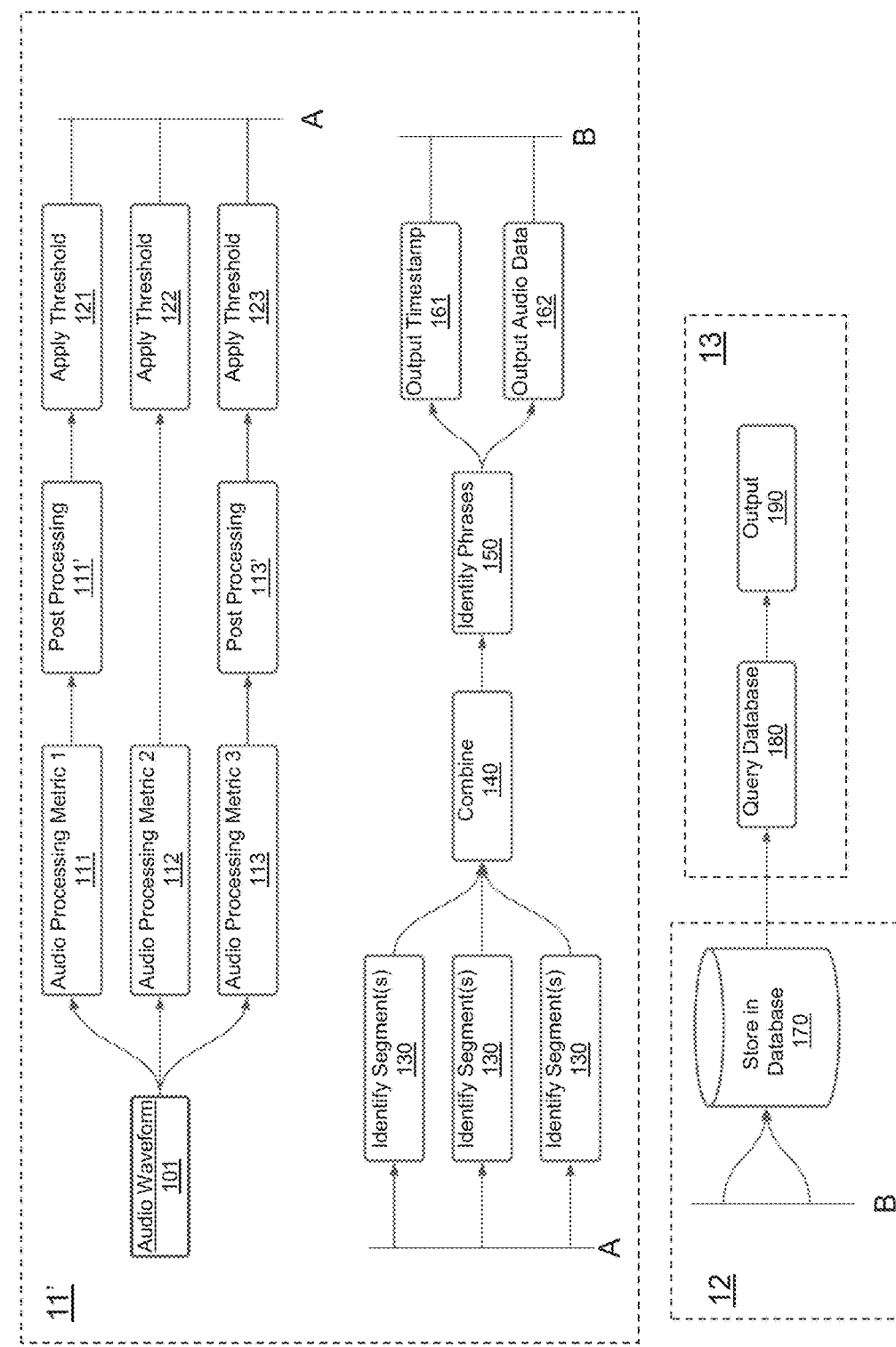
FIG. 1B is a detailed flowchart of the example routine for processing digital music data of FIG. 1A.

FIG. 1B is a detailed flowchart of an example embodiment for processing digital music data using one or more computer processors and shows additional intermediate processing steps not illustrated in FIG. 1A. In FIG. 1B A process 10 can include the routine 11 of FIG. 1A, a well as a storage routine 12 and a search routine 13. The routine 11' presented in FIG. 1B can include the routine 11 of FIG. 1A, but is presented here with additional steps that may or may not be included in the routine 11 of FIG. 1A.

The routine 11' of FIG. 1B can begin with audio data 101 of an audio waveform, which can be encoded using a number of known lossless and lossy techniques, such as an MP3, M4A, DSD, or WAV file. The audio data 101 can be received using an input of a computer system or retrieved from a database, which can be, for example, local to the computer system or retrieved through the internet. Once the audio data 101 is obtained, a plurality of different objective audio metrics 111, 112, 113 are separately executed by a processor of the computer system to extract first order data from the audio data 101, such as loudness per beat, loudness band ratio, and pitch melodia. In the next, optional step, post processing routines 111', 113' can be conducted using a processor to prepare the data for subsequent detection processing using a threshold. The post-processing routines 111', 113' can include, for example, converting the loudness per beat data using a low-pass envelope. In the next step, for each metric, an upper or lower boundary threshold 121, 122, 123 can be applied, using a processor, to the output data based on the distribution of the data, such as an upper or lower quartile function. In the next step, based on the application of the threshold 121, 122, 123 in the previous step, a detection algorithm 130 identifies segments of the data, using a processor, that meet the threshold requirement. The detection algorithm 130 can, in some examples, enforce requirements, such as a requirement that dictates the need for a selected segment to span a defined number of contiguous beats. For example, at least 2 seconds, or 2-10 seconds, or 1-30 seconds, or similar. The detection algorithm 130 can output the detections as binary masks.

A common need for detecting the chill-eliciting features within a signal involves highlighting the regions which represent a change in the signal, specifically sudden or concentrated changes. For example, artists and composers will increase the loudness to draw attention to a passage and generally the more dramatic the change in loudness, the more the listener will respond. Detecting the relevant segments within the signal normally involves identifying the highest or lowest relative regions within the recording. By employing thresholds such as an upper or lower quartile, aspects of the present disclosure detect regions with the most change relative to a range of dynamics established within a particular song. There can be wide diversity of dynamic ranges within different genres, and even between individual songs within a genre, and using absolute thresholds can undesirably over-select or under-select for most music, therefore the use of relativity of quantile-based thresholds (e.g., upper 25%) is advantageous. Furthermore, if the signal for a particular recording has a low amount of variation (e.g., the loudness is constant), the upper quartile of loudness will tend to select small and dispersed regions throughout the song which are not likely to align significantly with other features in the subsequent combination routine. However, if the signal peaks are concentrated within specific regions, the quartile-based threshold will select a coherent region that will tend to align concurrently with other features of interest in the subsequent combination routine. While the majority of feature detections illustrated in the present disclosure employ a quantile-based thresholding method, there are some features (e.g., key changes) that are not detected by the quantile-based thresholding method, but employ different techniques, which are discussed elsewhere in this document.

After individual segments are identified, those detections are provided to a combination routine 140 that, using a processor, aggregates the segments to determine where selected segments overlap (e.g., concurrences) and a higher numerical "score" is applied. The result is that, where there is no overlap between selections in data plots, the score is lowest, and where there is complete overlap between the selections in data plots the score is highest. The resulting scoring data, which is referred to herein as a chill moments plot, can itself be output and/or displayed visually as a new data plot at this stage. The routine 11' can include a subsequent step of executing a phrase identification routine 150. In this step 150, the output of the combination routine is analyzed, using a processor, for sections that contain high scores and segments. The segment with the highest overall score value can be considered the "primary chill phrase", while identified segments with lower scores (but still meeting the criteria for being selected) can be considered the "secondary chill phrases". In subsequent steps, the chill phrases can be output 161 as data in the form of timestamps indicating start and end points of each identified phrase and/or output 161 as audio files created to comprise only the "chill phrase" segments of the original audio data 101.

The process 10 can include a storage routine 12 that stores any of the data generated during execution of the routine 11, 11'. For example, chill moments plot data and chill phrases can be stored in a database 170 as either timestamps and/or digital audio files. The database 170 can also store and/or be the source of the original audio data 101.

Any part of the processes can include the operation of a graphical user interface to enable a user to execute any steps of the process 10, observe output and input data of the process 10, and/or set or change any parameters associated with the execution of the process 10. The process 10 can also include a search routine 13 that includes an interface (e.g., a graphical user interface and/or an interface with another computer system to receive data) to allow a user to query the accumulated database 170. A user can, for example, search 180 the database for songs that rank the highest in chills scoring as well as on several metadata criteria such as song name, artist name, song published year, genre, or song length. The user interface can enable the user to view the details of any selected song which includes the chill phrase timestamps as well as other standard metadata. The user interface can also interface with an output 190 that enables, for example, playback of the chill phrase audio as well as allowing the playback of the entire song with markings (e.g., an overlay on a waveform graphic of the selected song) indicating where the chill phrases are present in the audio. The output 190 can also enable a user to transfer, download, or view any of the data generated or associated with the operation of the process 10.

Figure 2A:
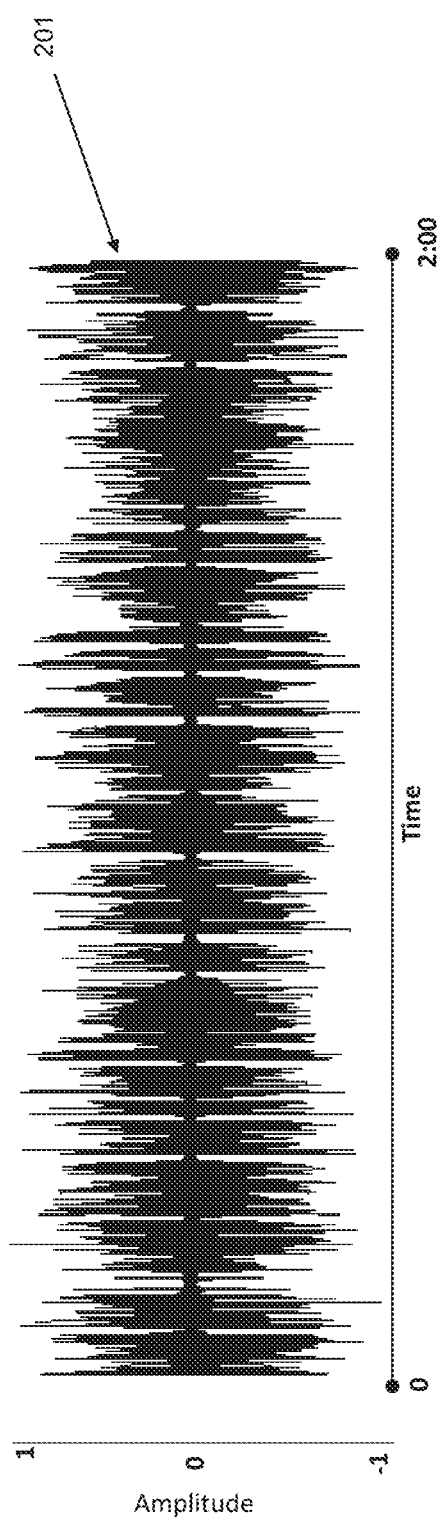
FIG. 2A is a graph of amplitude over time for an example waveform of a digital music file.

FIG. 2A is a graph 200 of amplitude (y-axis) over time (x-axis) for an example waveform 201 of a digital music file. The waveform example of FIG. 2A is completely made up and for illustration purposes only, as are the outputs of the audio metrics presented in FIGS. 2B and 2C. In operation, examples of the present disclosure include running two or more objective audio processing metrics (111, 112, 113 of FIG. 1B) on the waveform 201 to generate output data, an example of which is shown in FIG. 2B.

Figure 2B:
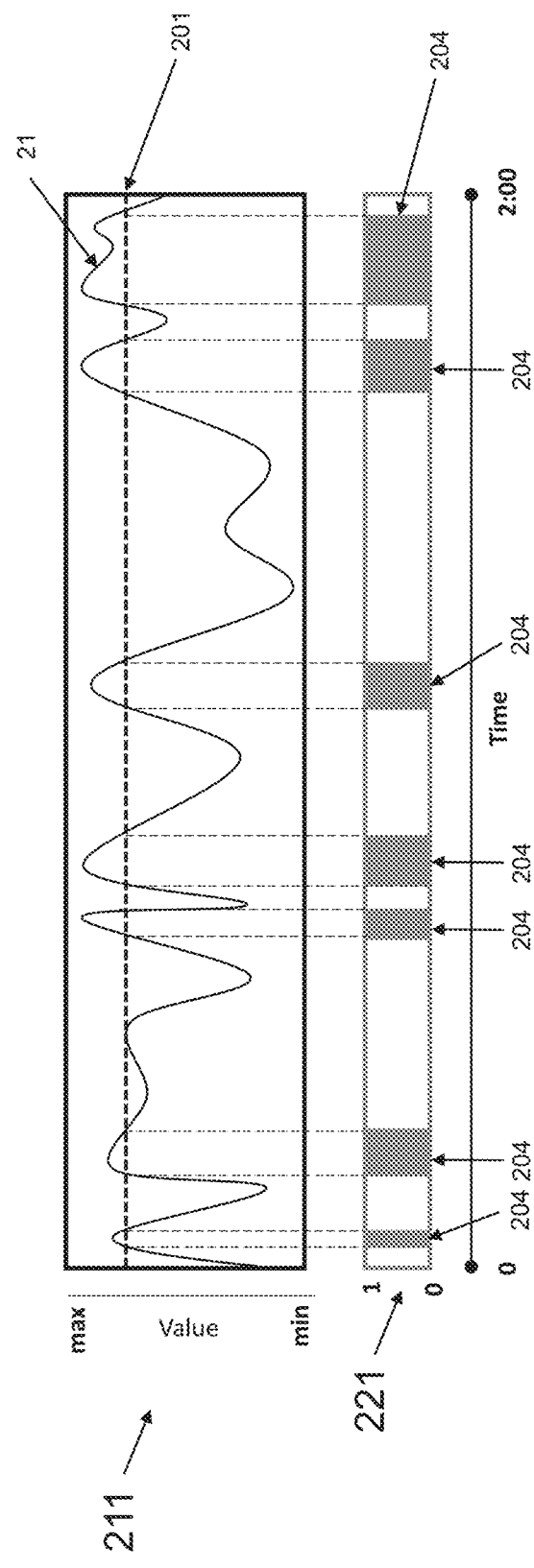
FIG. 2B is a visual representation of an example output of a first representative objective audio processing metric with a corresponding plot of identified GLIPhs.

FIG. 2B includes a plot 211 of an example output 21 of a first representative objective audio processing metric (e.g., 1/1 in FIG. 1B) with a corresponding output mask 221 of identified GLIPhs 204. In FIG. 2B, the output 21 ranges from a minimum to a maximum value and a threshold 201 can be applied in order to enable a detection algorithm (e.g., 130 in FIG. 1B) to extract individual acoustic events from the output 21 where the output satisfies a detection criteria (e.g., threshold 201). While the detection criteria illustrated in FIG. 2B is a simple upper quintile of the values of the output 21, other, more complex detection criteria are possible as well, and may require a post-processing 111' step before application (e.g., taking a derivative or Fourier transform to detect harmonies between concurrent notes). Additionally, post-processing 111' can be used to change the time-domain from a processing interval (e.g., 0.1 ms) to a per-beat. Additionally post-processing 111' can be used to transform a frequency domain processing to a time domain output. Use of a per-beat time frame can enable metrics to be adaptive relative to the base 'atoms' of the song so that tempo is not a confounding factor. The level of granularity can be deeper for some features such as pitch, or higher level features that encapsulate many other features such as spectral flux or spectrum centroid however the level does not have to be much smaller than beat level to gain effective results.

In FIG. 2B, once a detection criteria (e.g., threshold 201) is applied, a detection algorithm 130 converts the output 21 into a binary mask 221 of individual detection events 204 (also referred to herein as GLIPhs), which are positive (e.g., value of 1) in time regions where the detections occur and null (e.g., value of 0) in the time regions between detections. The output mask 221 in provided as one input to the combination algorithm (e.g., 140 in FIG. 1B), with another input mask coming from a second metric processing the same audio waveform (201 of FIG. 2A), as shown in FIG. 2C.

Figure 2C:
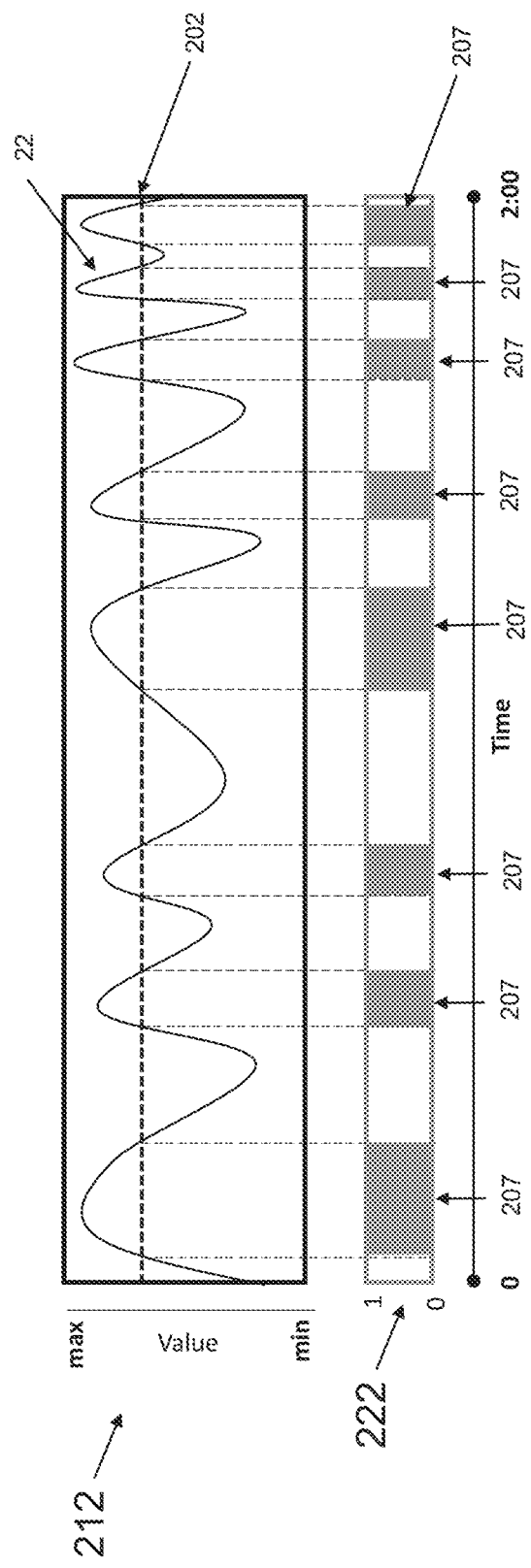
FIG. 2C is a visual representation of an example output of a second representative objective audio processing metric with a corresponding plot of identified GLIPhs.

FIG. 2C includes a plot 212 of an example output 22 of a second representative objective audio processing metric (e.g., 112 in FIG. 1B) with a corresponding output mask 222 of identified GLIPhs 207. In FIG. 2C, the output 22 ranges from a minimum to a maximum value and a threshold 202 can be applied in order to enable a detection algorithm (e.g., 130 in FIG. 1B) to extract individual acoustic events from the output 22 where the output satisfies a detection criteria (e.g., threshold 202). While the detection criteria illustrated in FIG. 2C is a simple upper quartile of the values of the output 22, other, more complex detection criteria are possible as well and can depend on the nature of the GLIPh being detected in the output 22 of the metric.

In FIG. 2C, once a detection criteria (e.g., threshold 202) is applied, a detection algorithm 130 converts the output 22 into a binary mask 222 of individual detection events 207 (also referred to herein as GLIPhs), which are positive (e.g., value of 1) in time regions where the detections occur and null (e.g., value of 0) in the time regions between detections. The output mask 222 in provided as an input to a combination algorithm 140, with the input mask 221 of FIG. 2B, as shown in FIG. 2D.

Figure 2D:
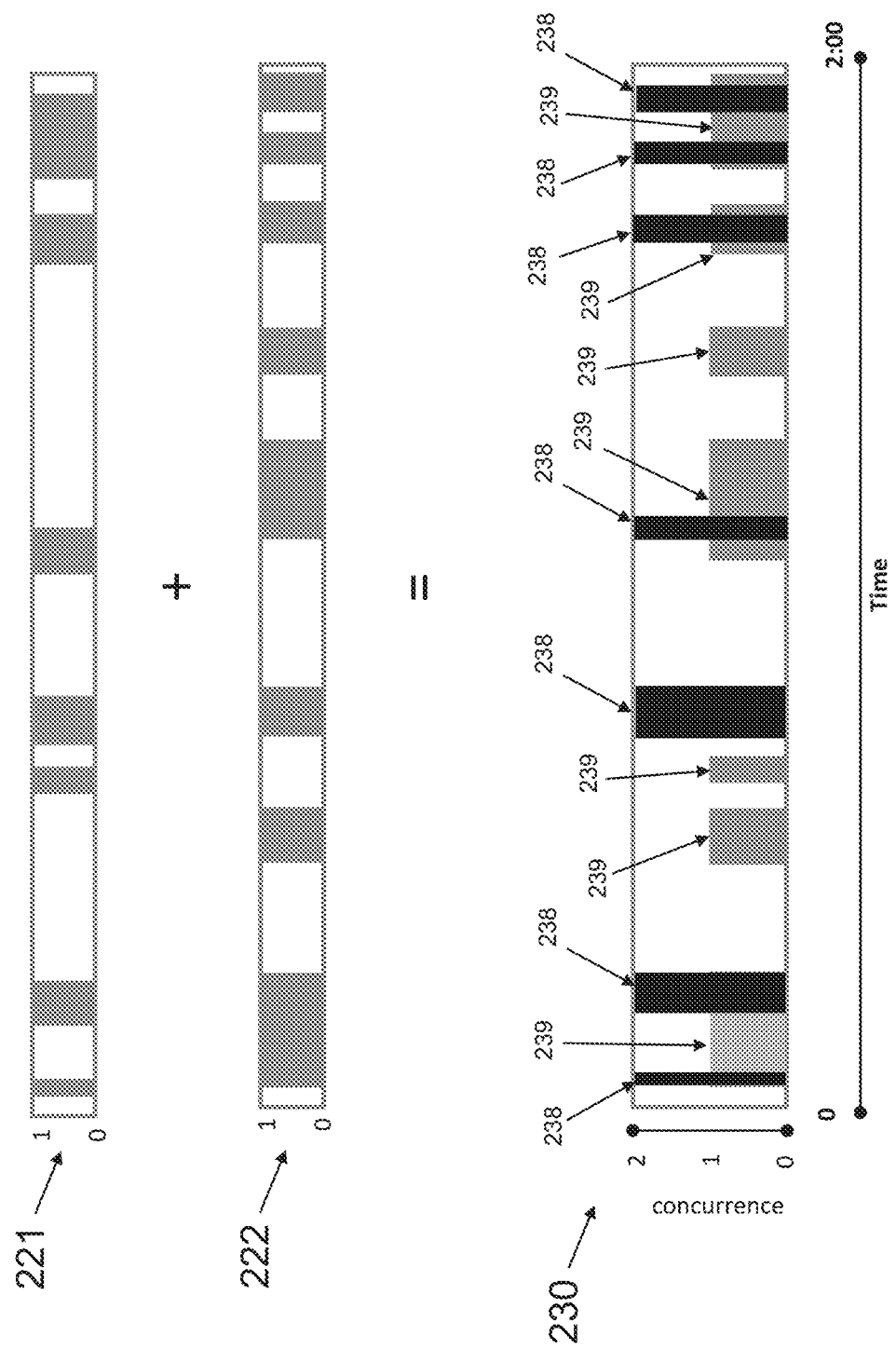
FIG. 2D is a visual representation of an example output of a combination algorithm based on identified GLIPhs of the first and second representative objective audio processing metrics.
Figure 2E:
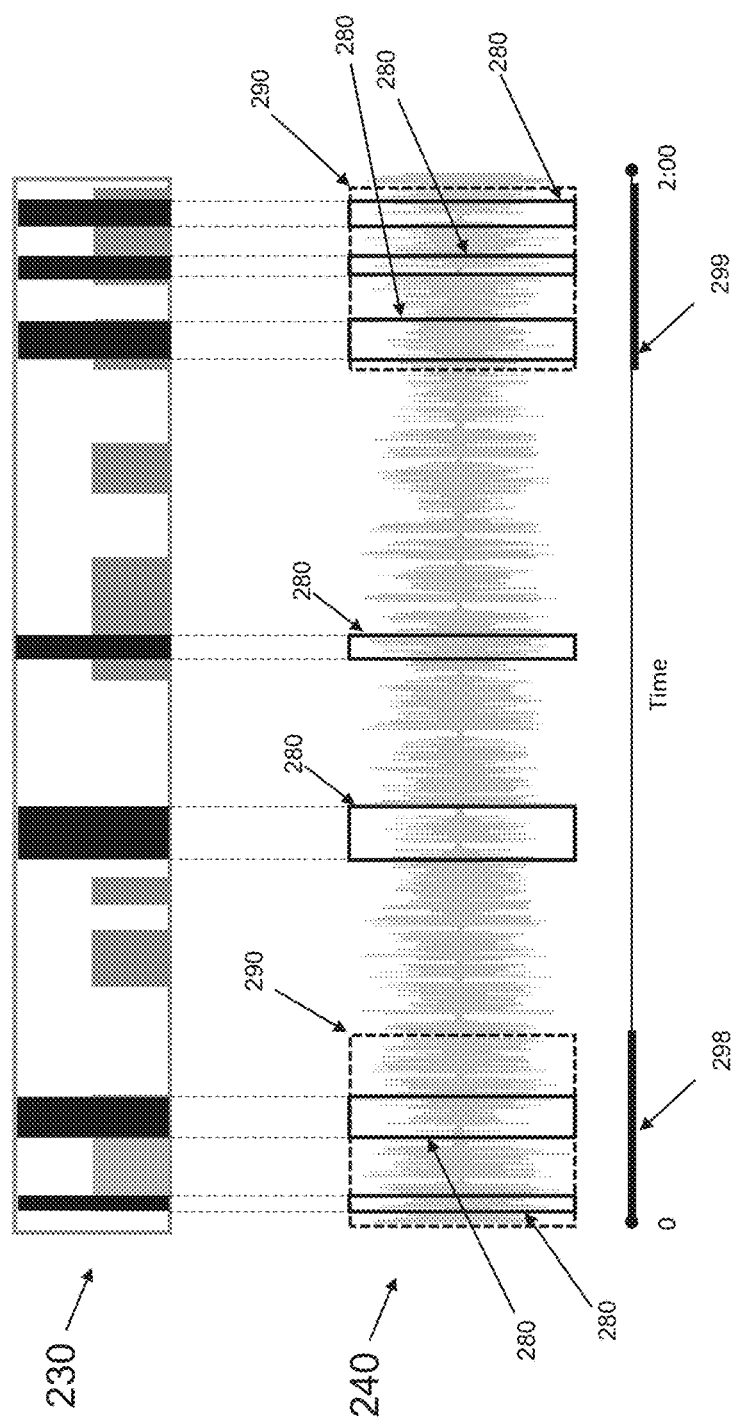
FIG. 2E is a visual representation of an example output of a phrase detection algorithm based on the output of the combination algorithm of FIG. 2D.

FIG. 2D includes plots of the masks 221, 222 of the detections from the two metrics of FIGS. 2B and 2C, and an impact plot 230 of an example output (e.g., chill moments plot) of a combination algorithm 140 using based on identified GLIPhs of the first and second representative objective audio processing metrics. In the impact plot 230 of FIG. 2D, the masks 221, 222 are aggregated, with concurrent detections adding to create first regions 238 where both masks are positive (e.g., a concurrence value of 2), second regions 239 where only one mask is positive (e.g., a concurrence value of 1), and null regions in between. In some instances, the input masks 221, 222 have the time-domain spacing (e.g., per beat), but this is not required, and the impact plot 230 can be created using any time-domain spacing (e.g., minimum x-axis intervals) to construct the first and second regions 238, 239. In some instances, and as shown in more detail herein, a moving average of first and second regions 238, 239 can be created and included in the impact plot 230. Using the second regions 238, which represent peaks in the chill moments plot, individual timestamps can be mapped back to the audio waveform of FIG. 2A, as shown in FIG. 2E as peak moments 280 in the audio data. Using these peak moments 280, a phrase detection algorithm (e.g., 150 in FIG. 2B) can identify impact regions 290 in the time-domain where peaks 280 are present and, in some instances, clustered together to create an output data of timestamps 298, 299 corresponding to the locations of the identified phrases 290.

Audio Processing Examples

Figure 3A:
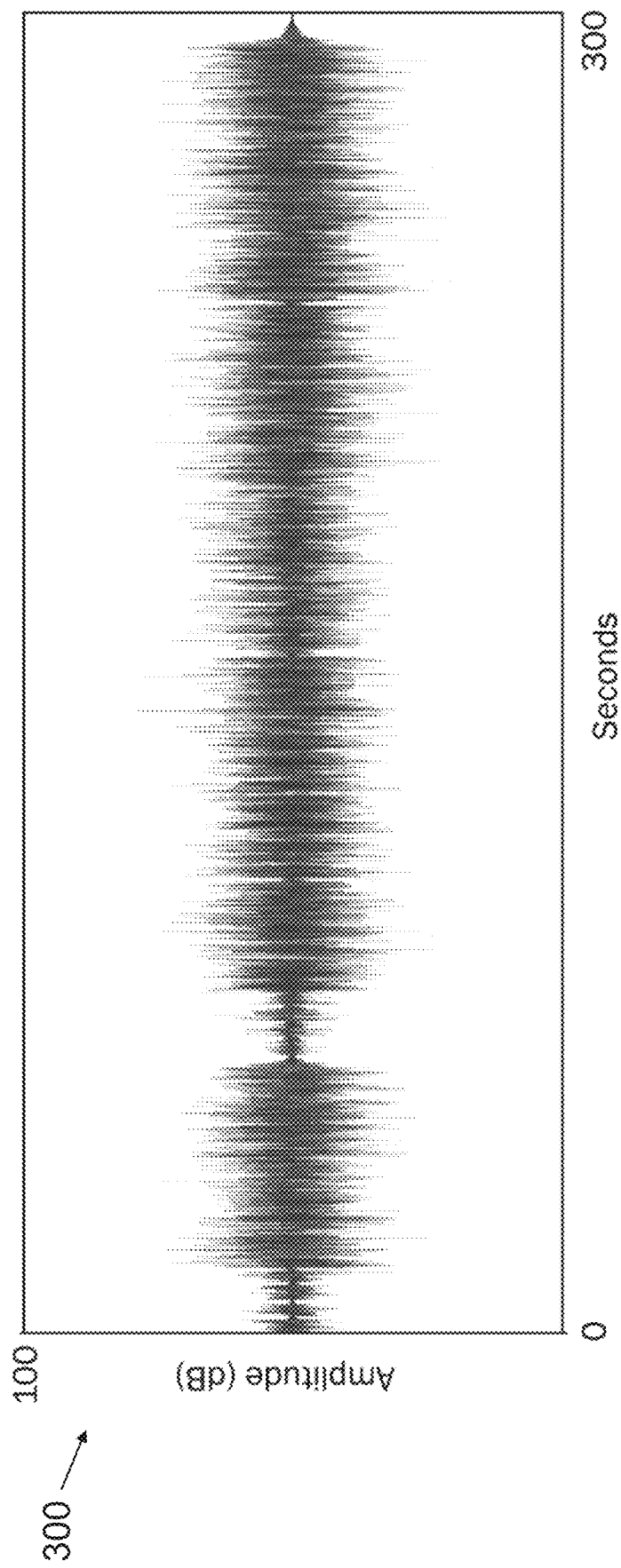
FIG. 3A is a visual illustration of a waveform of a digital music file.
Figure 3B:
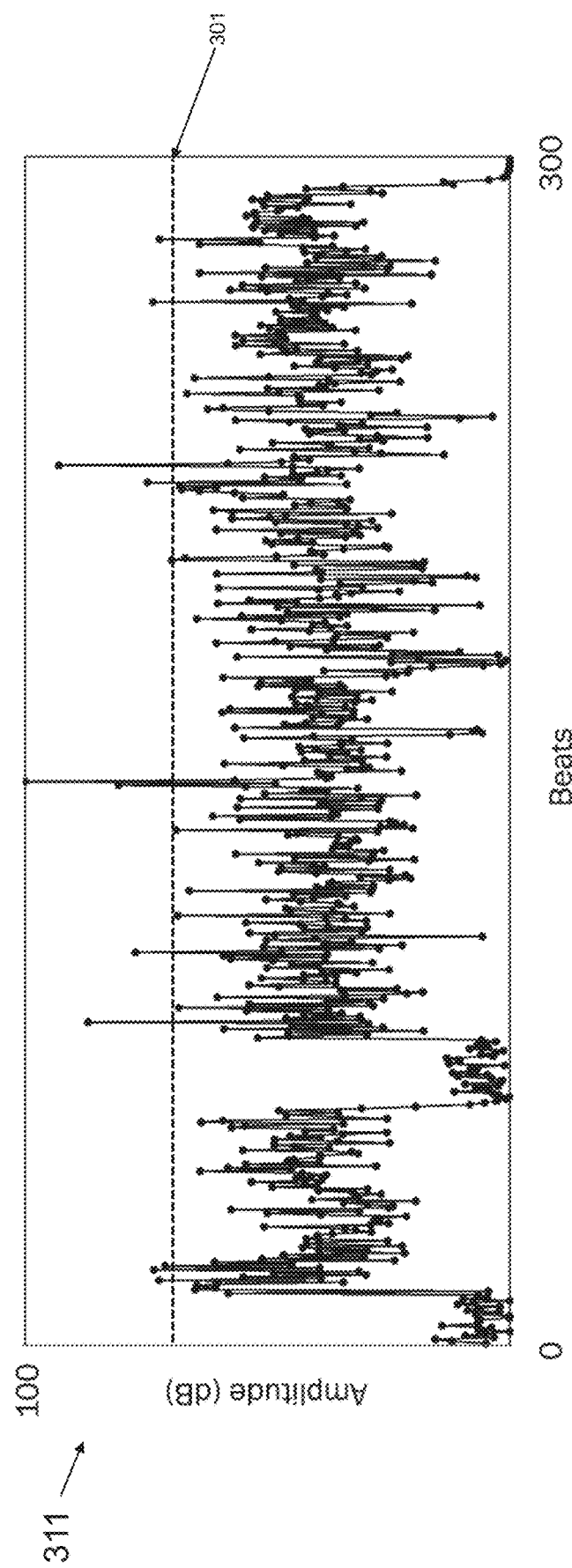
FIG. 3B is a visual representation of an outputs of a loudness metric based on the waveform of FIG. 3A.
Figure 3C:
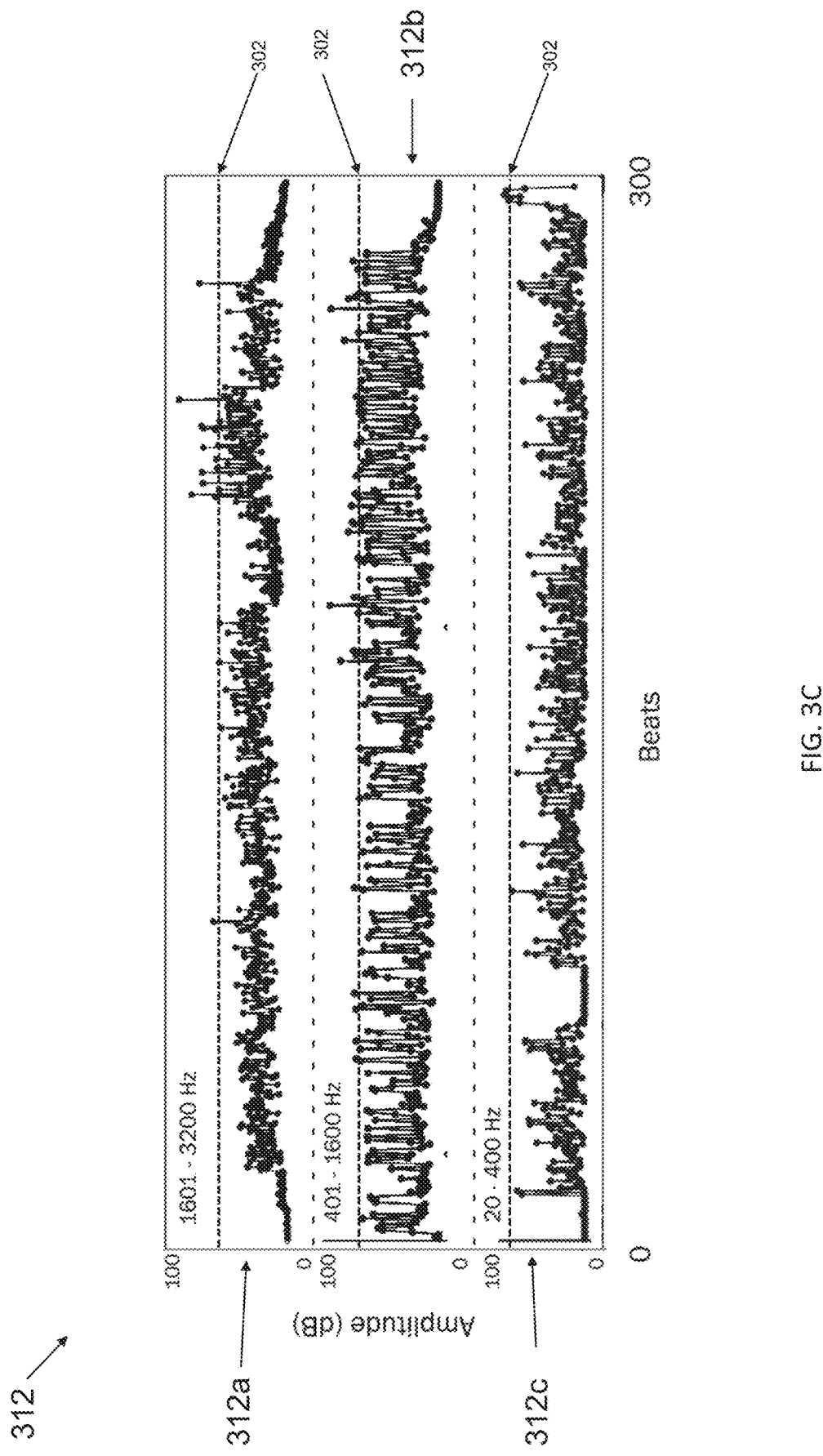
FIG. 3C is a visual representation of outputs of a loudness band ratio metric in three different loudness bands based on the waveform of FIG. 3A.
Figure 3D:
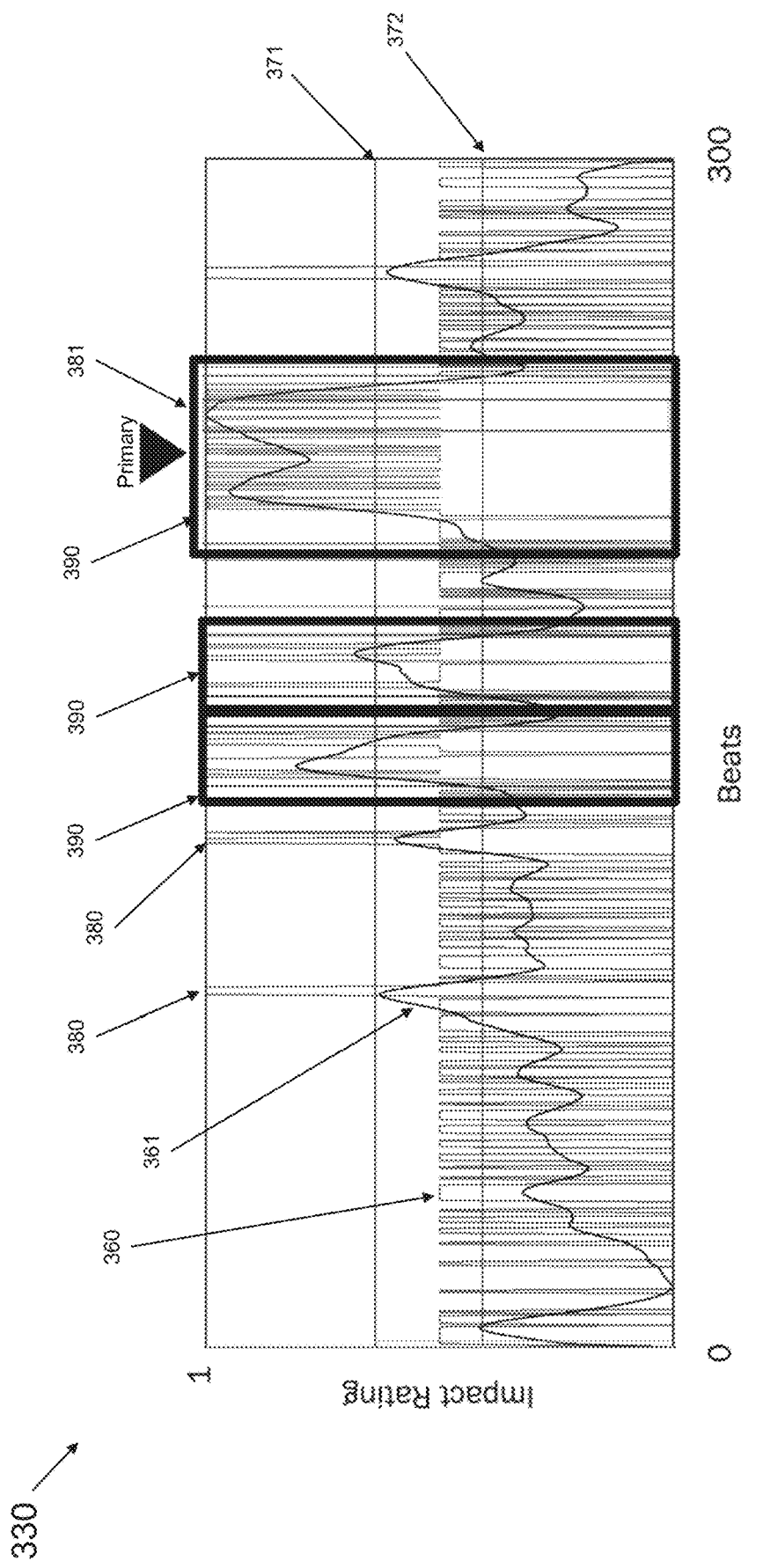
FIG. 3D is an illustration of an example output of a combination algorithm based on the objective audio processing metrics of FIGS. 3B and 3C overlaid with an output of a phrase detection algorithm applied to the output of the combination algorithm.
Figure 3E:
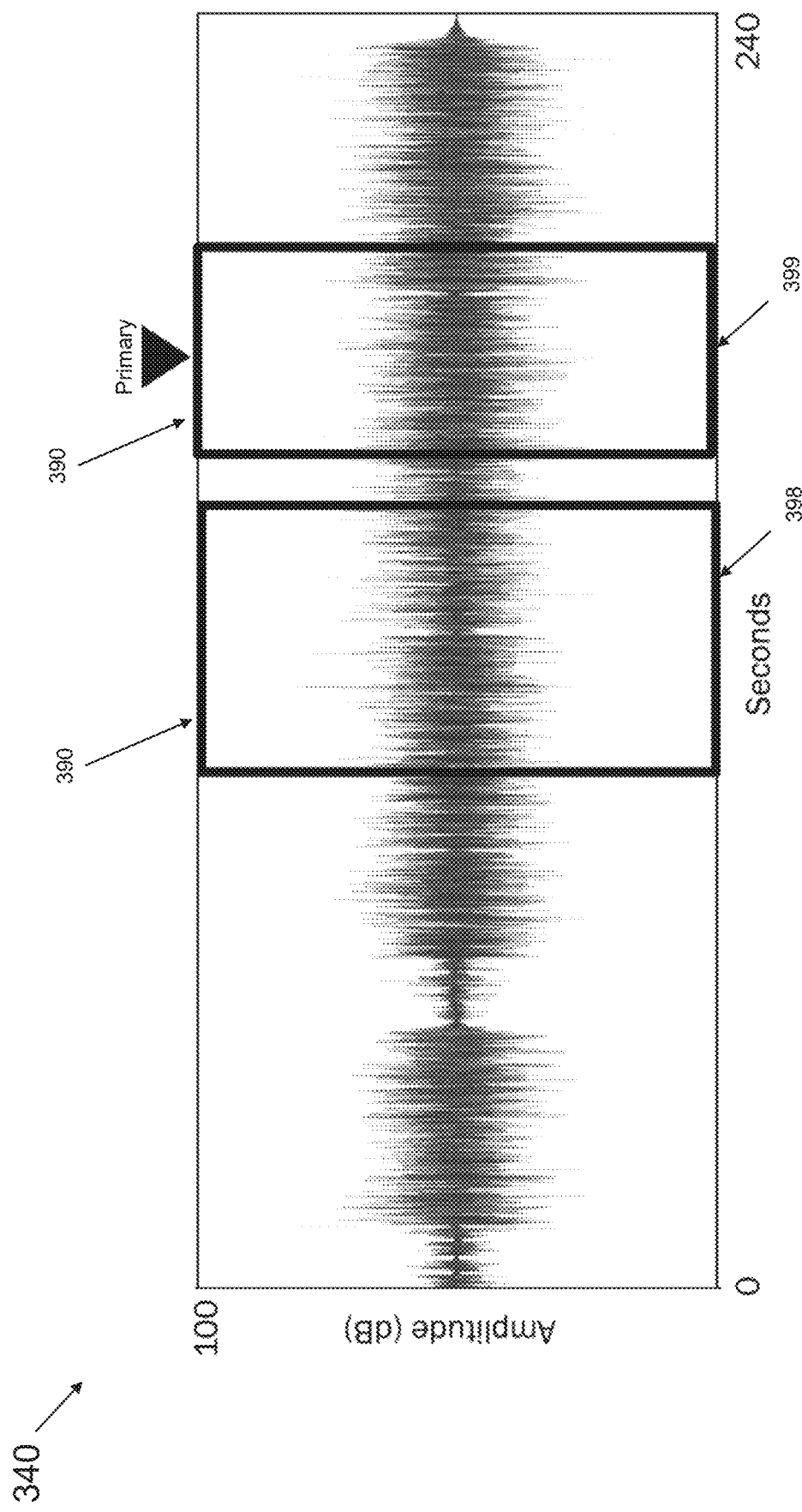
FIG. 3E is a visual illustration of the waveform of FIG. 3A showing the output of the phrase detection algorithm of FIG. 3D.
Figure 4A:
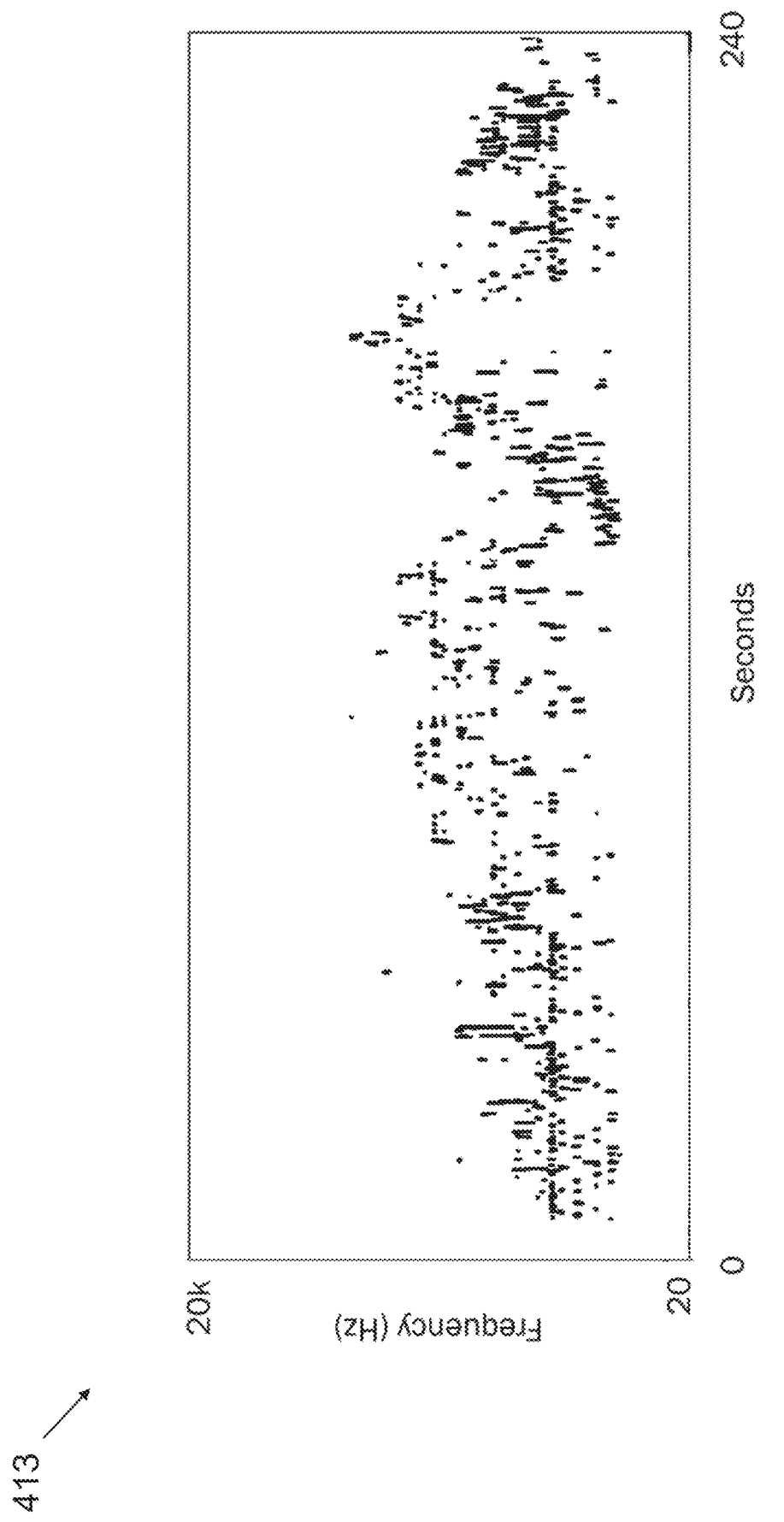
FIG. 4A is a visual representation of an output of a predominant pitch melodia metric based on the waveform of FIG. 3A.
Figure 4B:
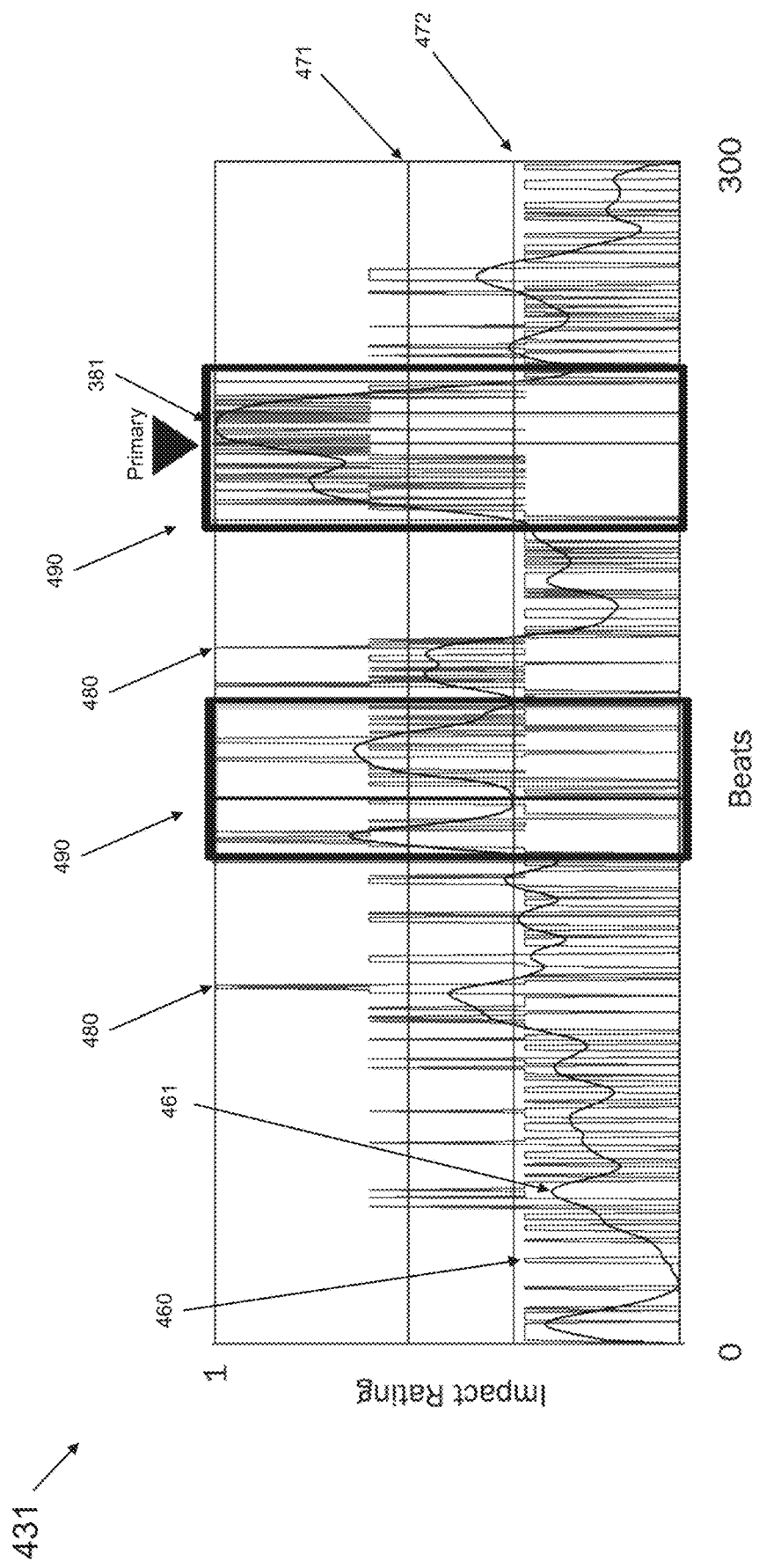
FIG. 4B is an illustration of an example output of a combination algorithm based on the objective audio processing metrics of FIGS. 3B, 3C, and 4A overlaid with an output of a phrase detection algorithm applied to the output of the combination algorithm.
Figure 4C:
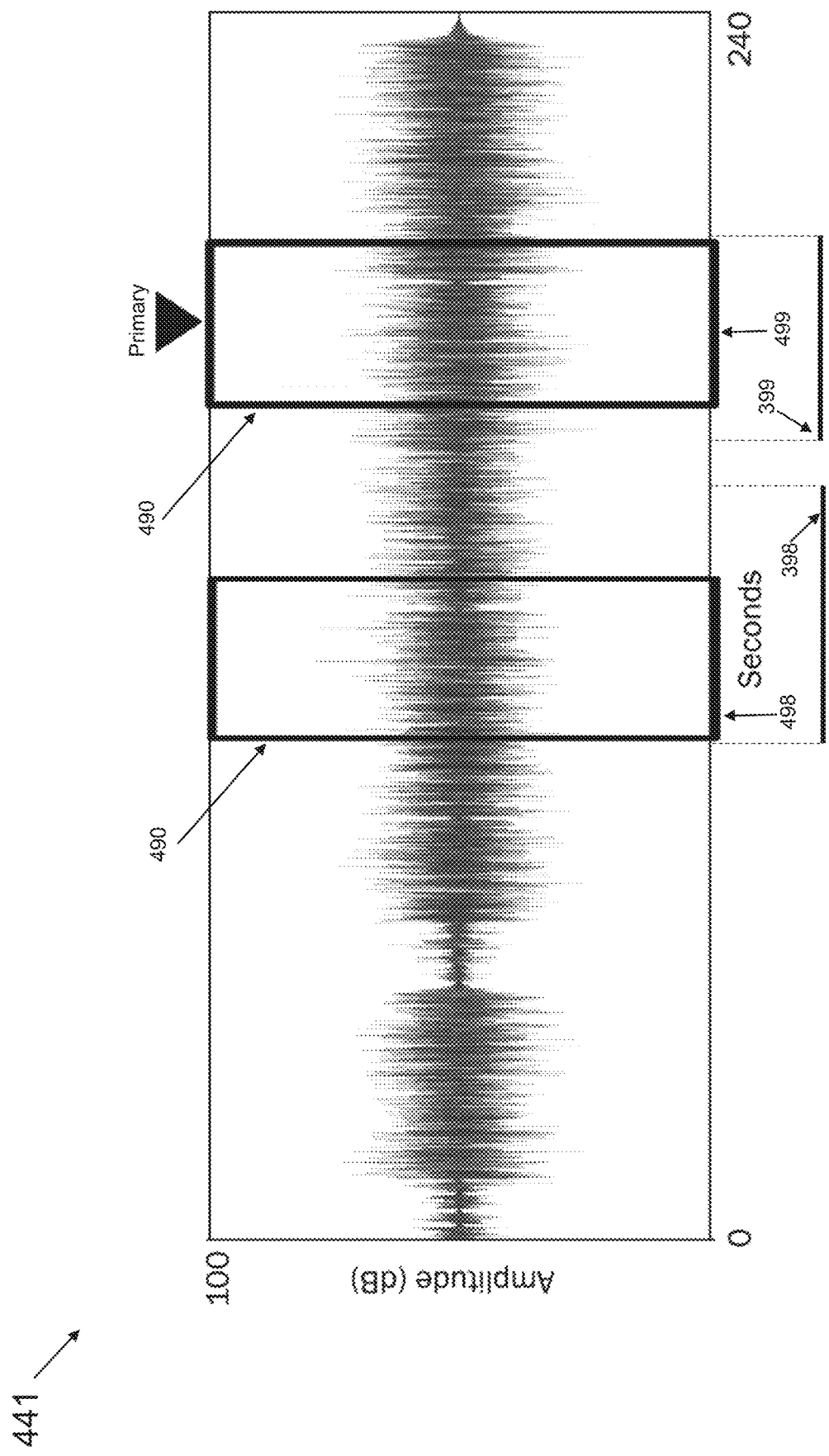
FIG. 4C is a visual illustration of a waveform of FIG. 3A showing the output of the phrase detection algorithm of FIG. 4B and shows a comparison to the output of the phrase detection algorithm shown in FIG. 3E.

FIGS. 3A-3E show processing steps for an example audio file using two objective audio processing metrics according to embodiments of the present disclosure, with FIGS. 4A-4C showing the same audio file processing with the addition of a third metric.

Figure 5A:
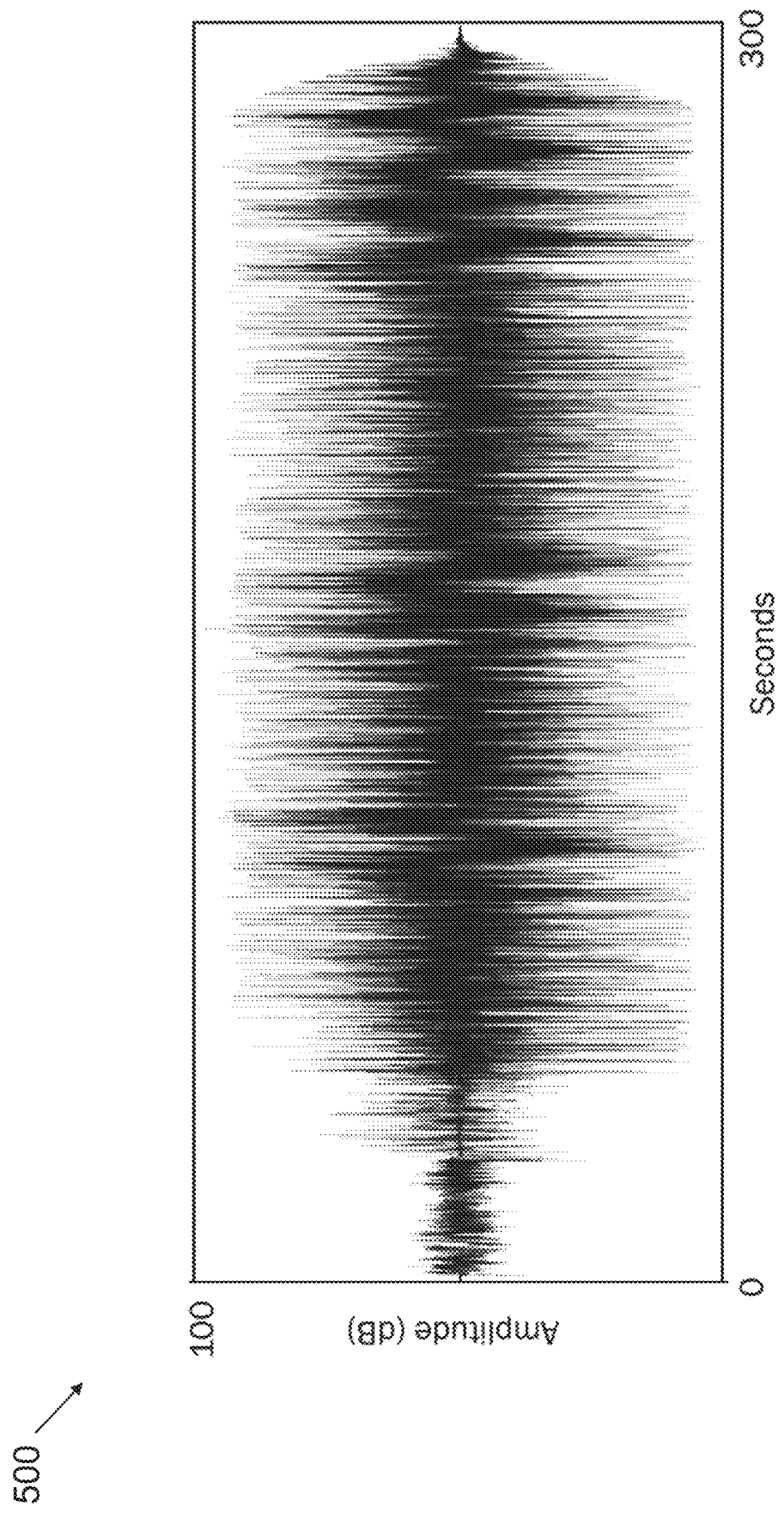
FIG. 5A is a visual illustration of a waveform of a different digital music file.
Figure 5B:
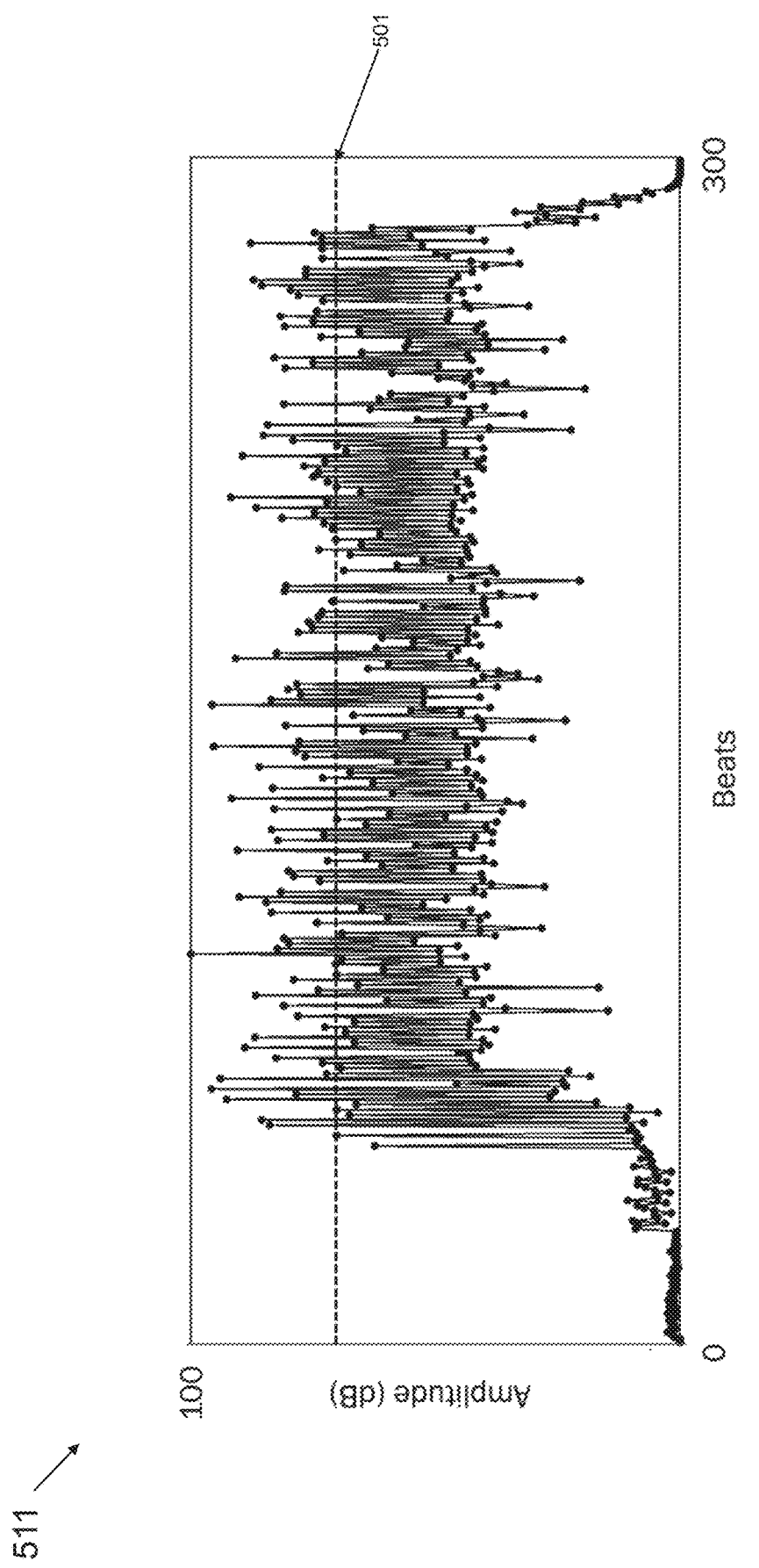
FIG. 5B is a visual representation of an output of a loudness objective audio processing metric based on the waveform of FIG. 5A.
Figure 5C:
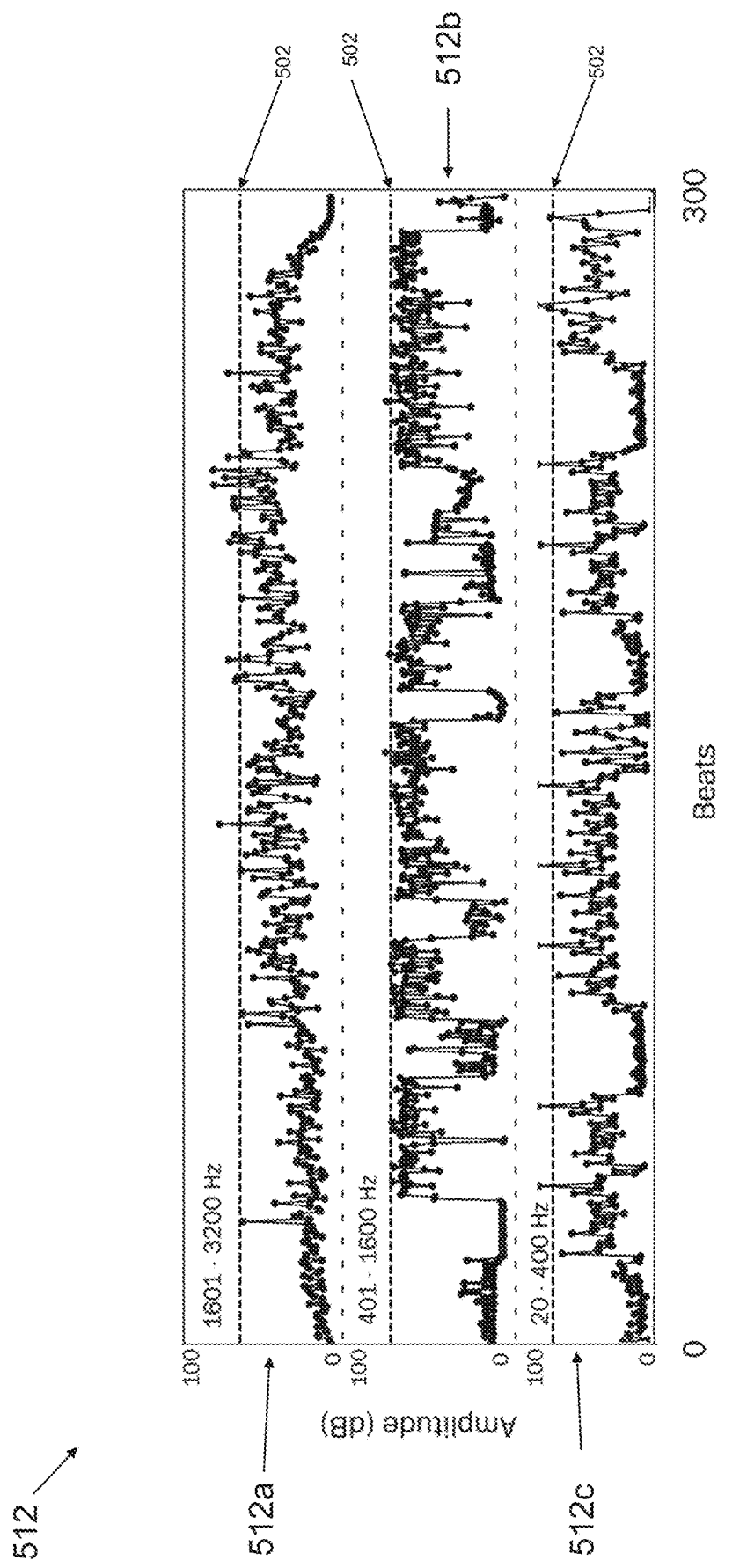
FIG. 5C is a visual representation of outputs of a loudness band ratio algorithm metric in three different loudness bands based on the waveform of FIG. 5A.
Figure 5D:
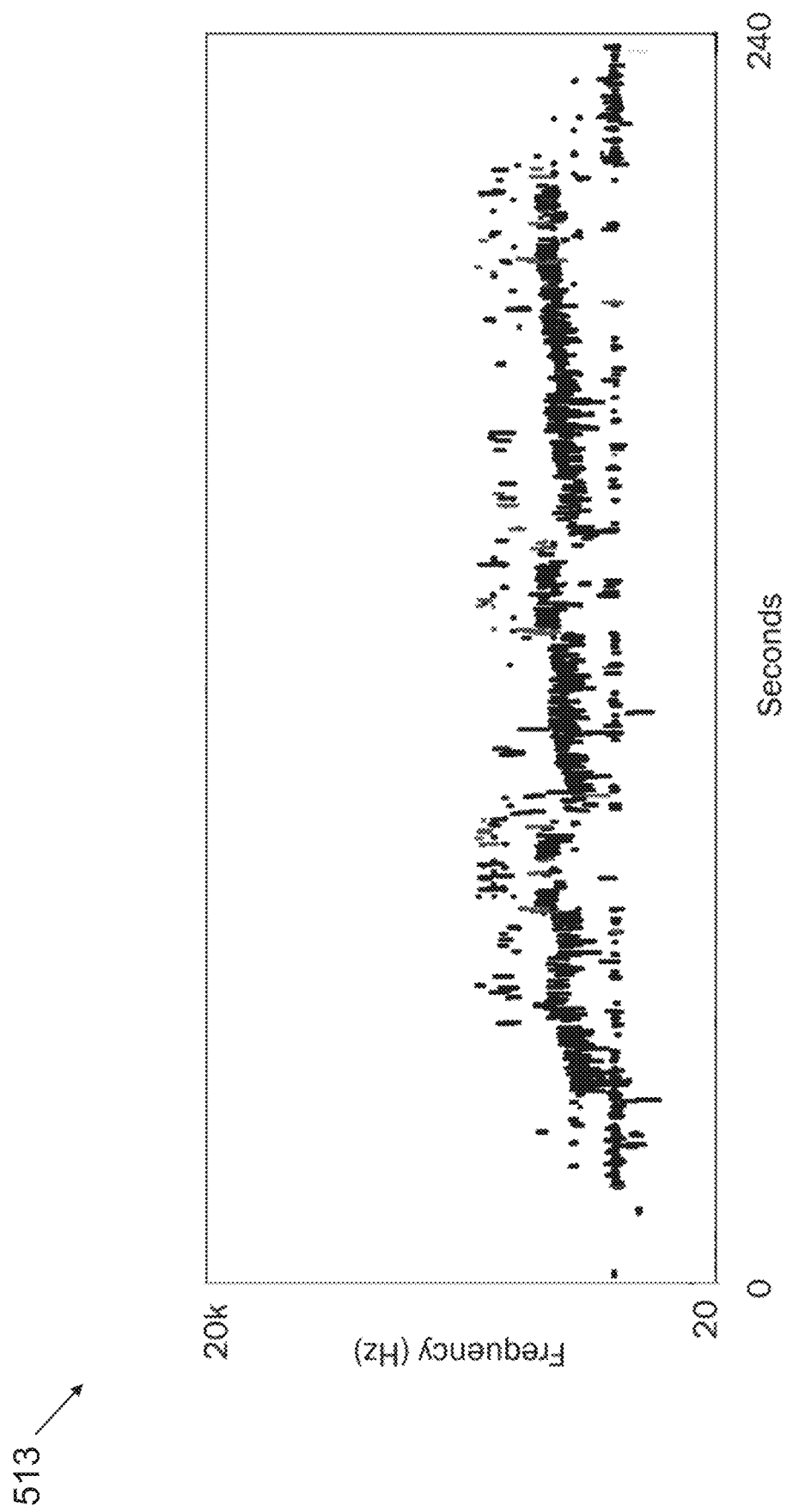
FIG. 5D is a visual representation of an output of a predominant pitch melodia metric run on the waveform of FIG. 5A.
Figure 5F:
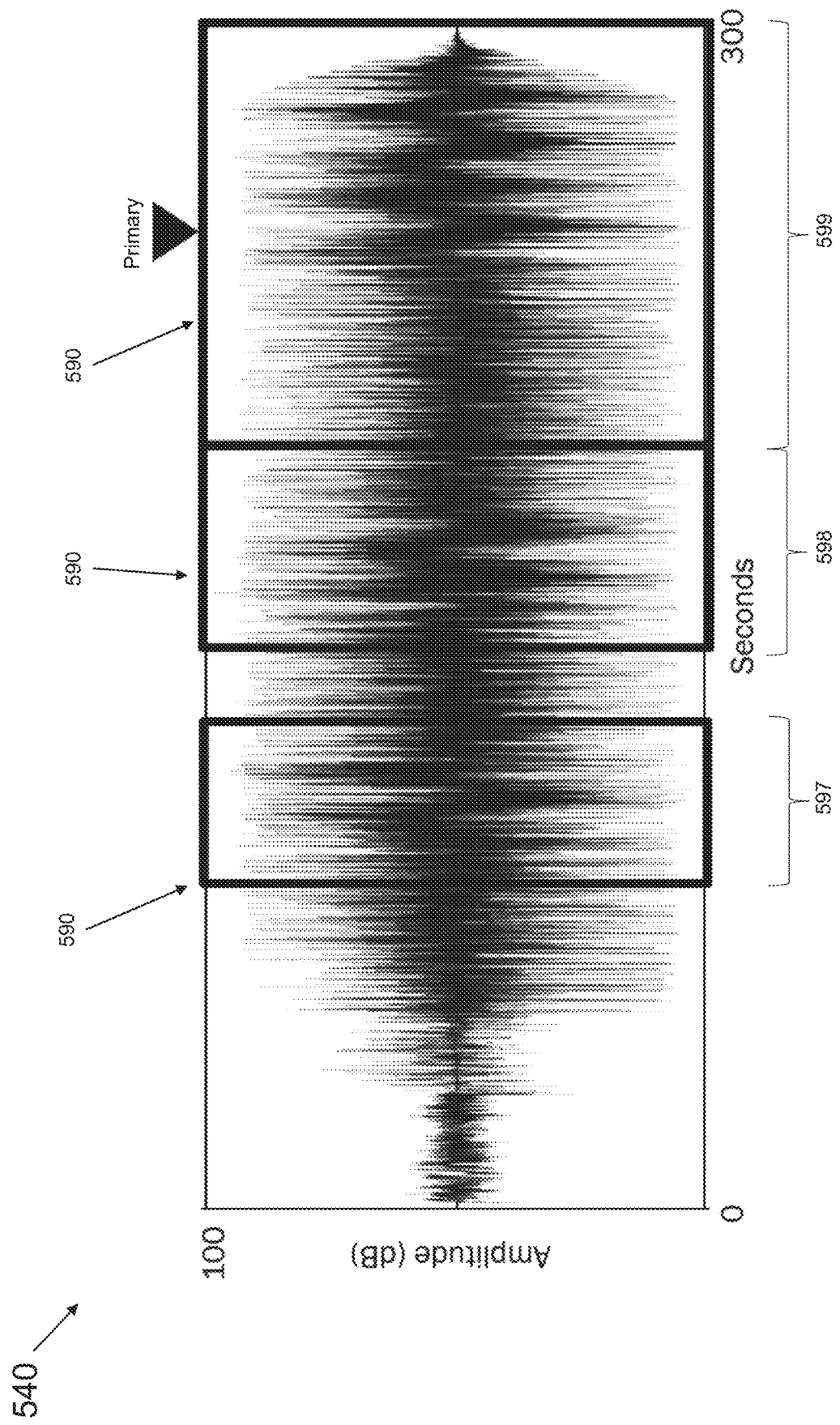
FIG. 5F is a visual illustration of a waveform of FIG. 5A showing the output of the phrase detection algorithm of FIG. 5E.
Figure 6A:
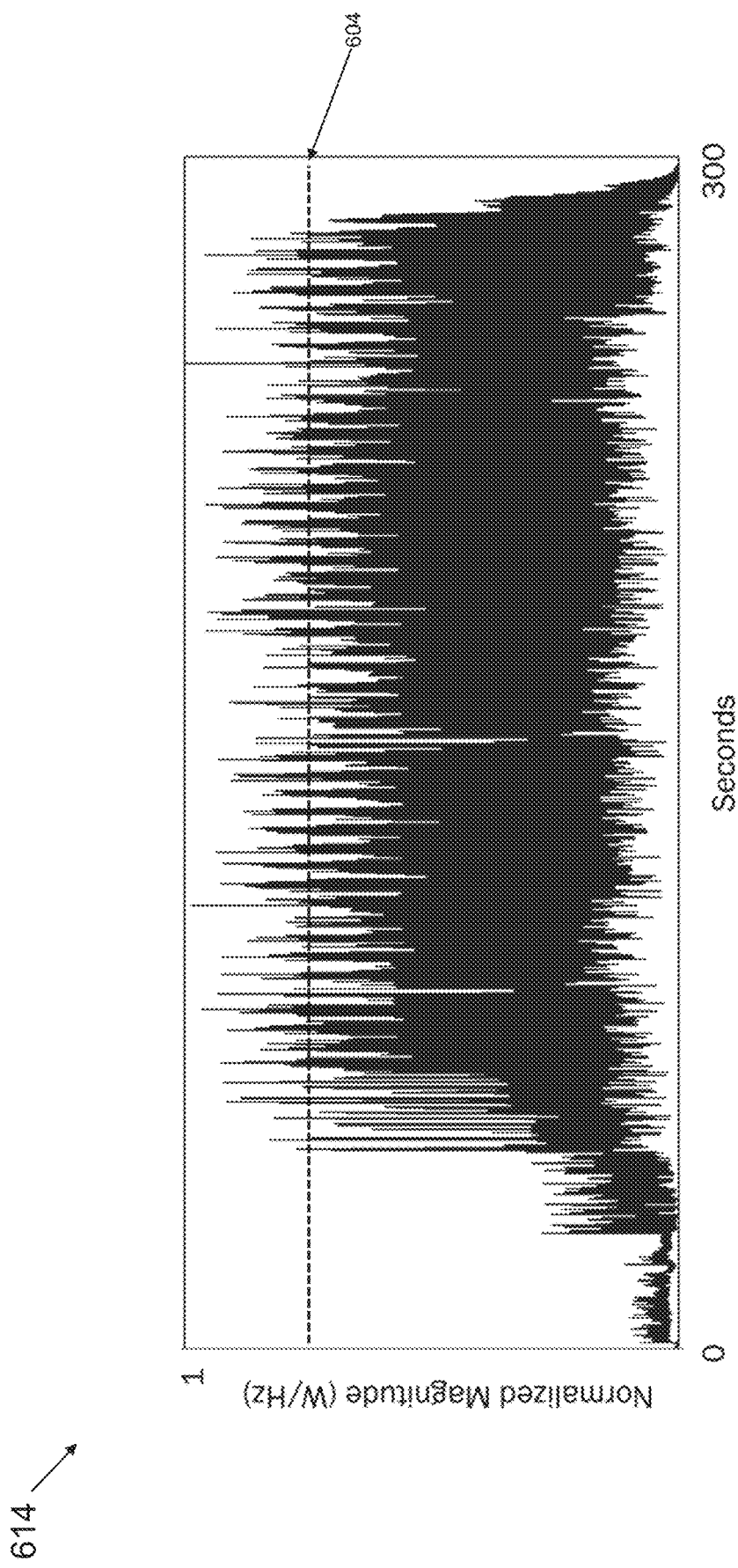
FIG. 6A is a visual representation of an output of a spectral flux metric based on the waveform of FIG. 5A.
Figure 6B:
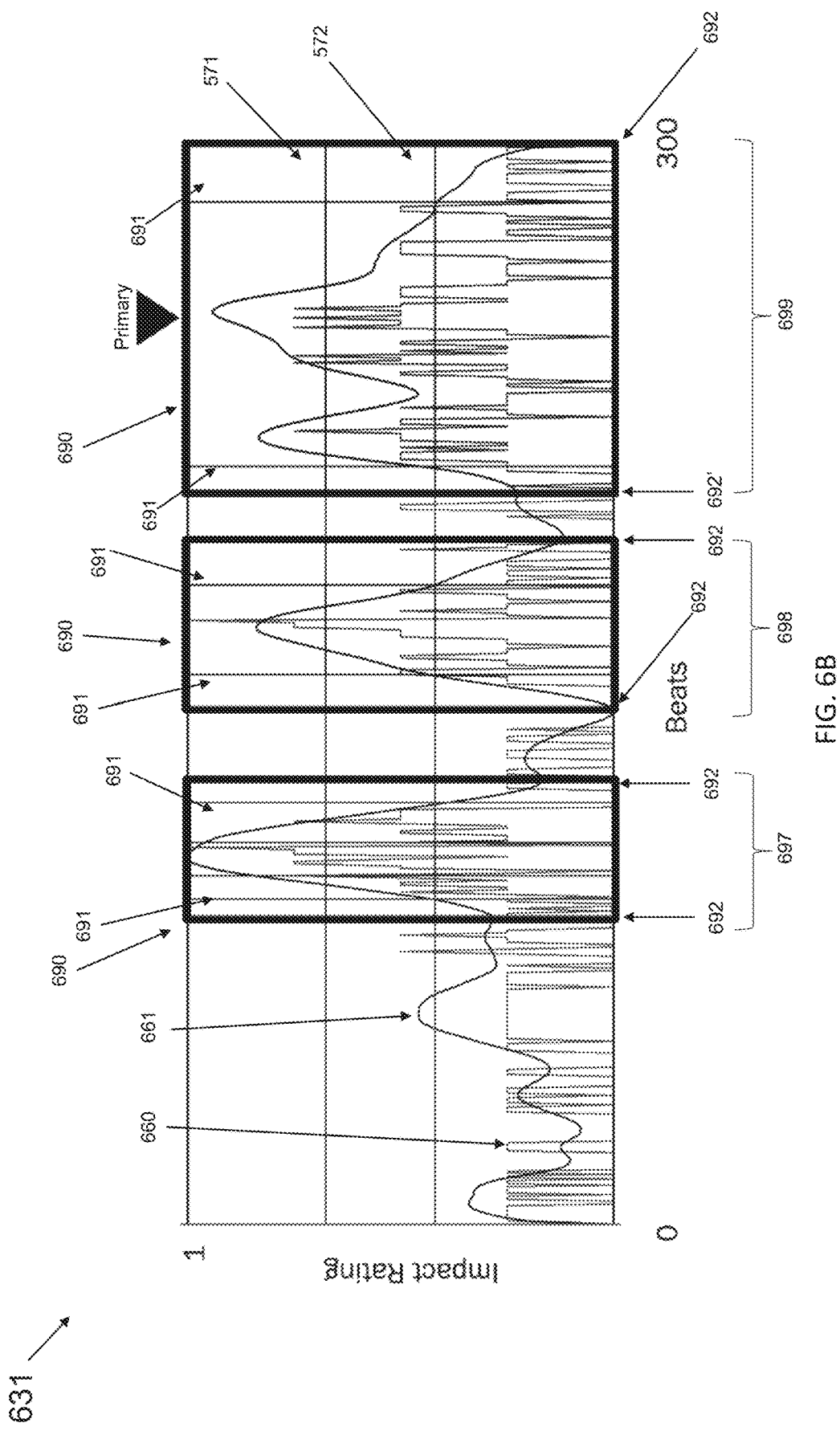
FIG. 6B is an illustration of an example output of a combination algorithm based on the objective audio processing metrics of FIGS. 5B, 5C, 5D, and 6A, overlaid with an output of a phrase detection algorithm applied to the output of the combination algorithm.
Figure 6C:
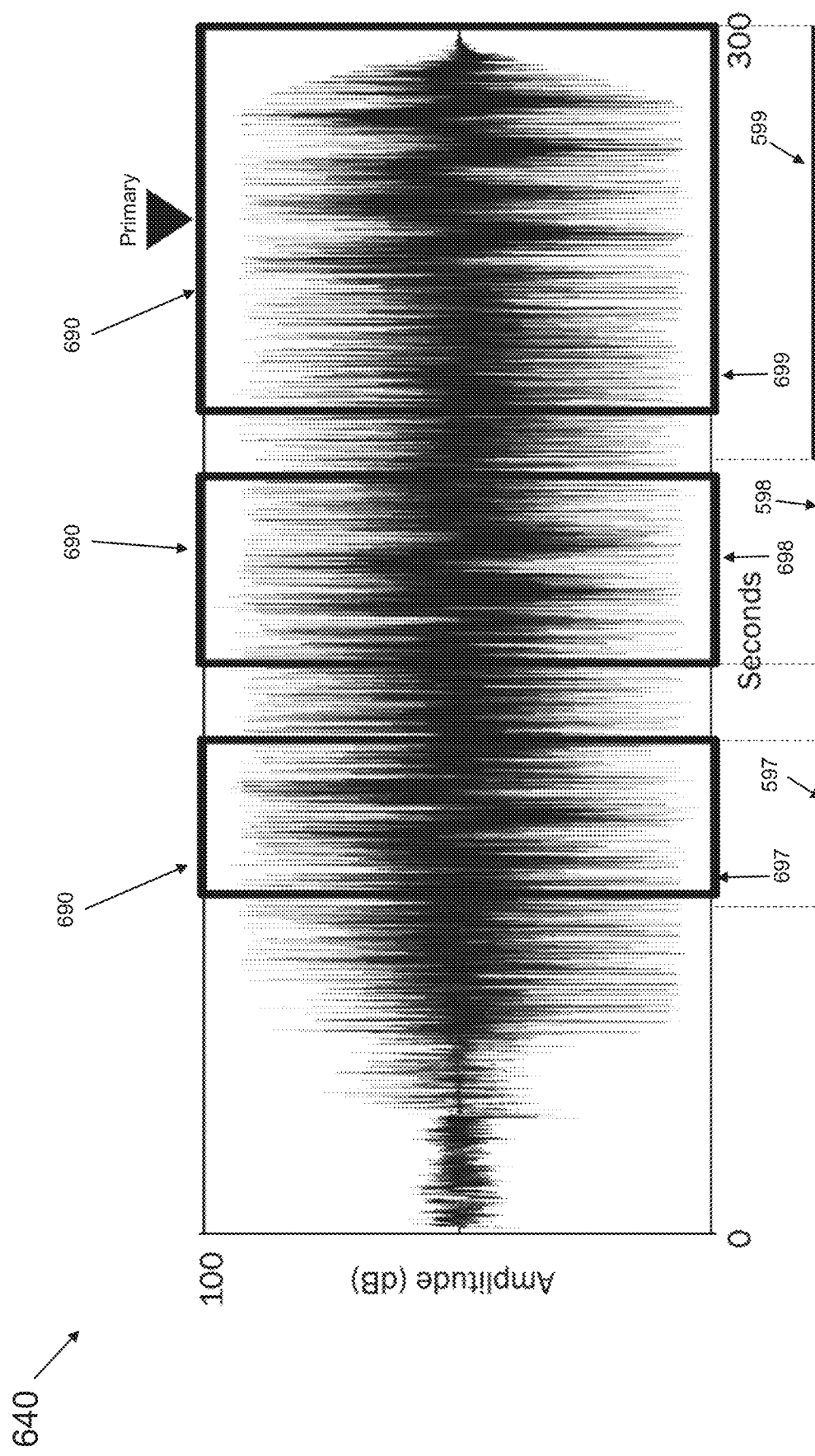
FIG. 6C is a visual illustration of a waveform of FIG. 5A showing the output of the phrase detection algorithm of FIG. 6B and shows a comparison to the output of the phrase detection algorithm shown in FIG. 5F.

FIGS. 5A-5F show processing steps for a different example audio file using three objective audio processing metrics according to embodiments of the present disclosure, with FIGS. 6A-6C showing the same audio file processing with the addition of a fourth metric.

Figure 7:
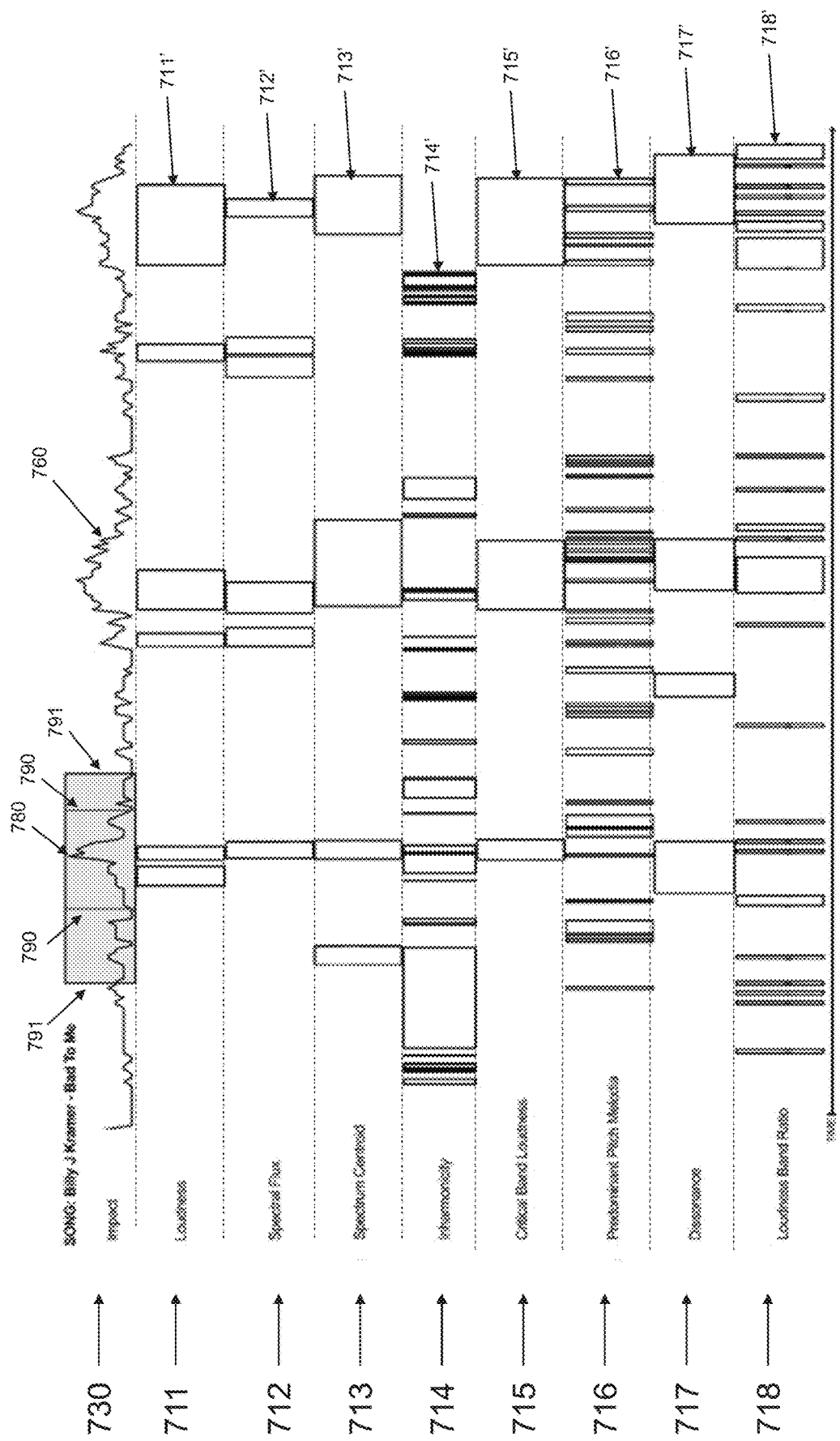
FIG. 7 is a group of plots generated using another song waveform as an input and showing detection outputs from a plurality of objective audio processing metrics based on the song waveform and an output from a combination algorithm based on the outputs of the plurality of objective audio processing metrics overlaid with an output of a phrase detection algorithm applied to the output of the combination algorithm.
Figure 8:
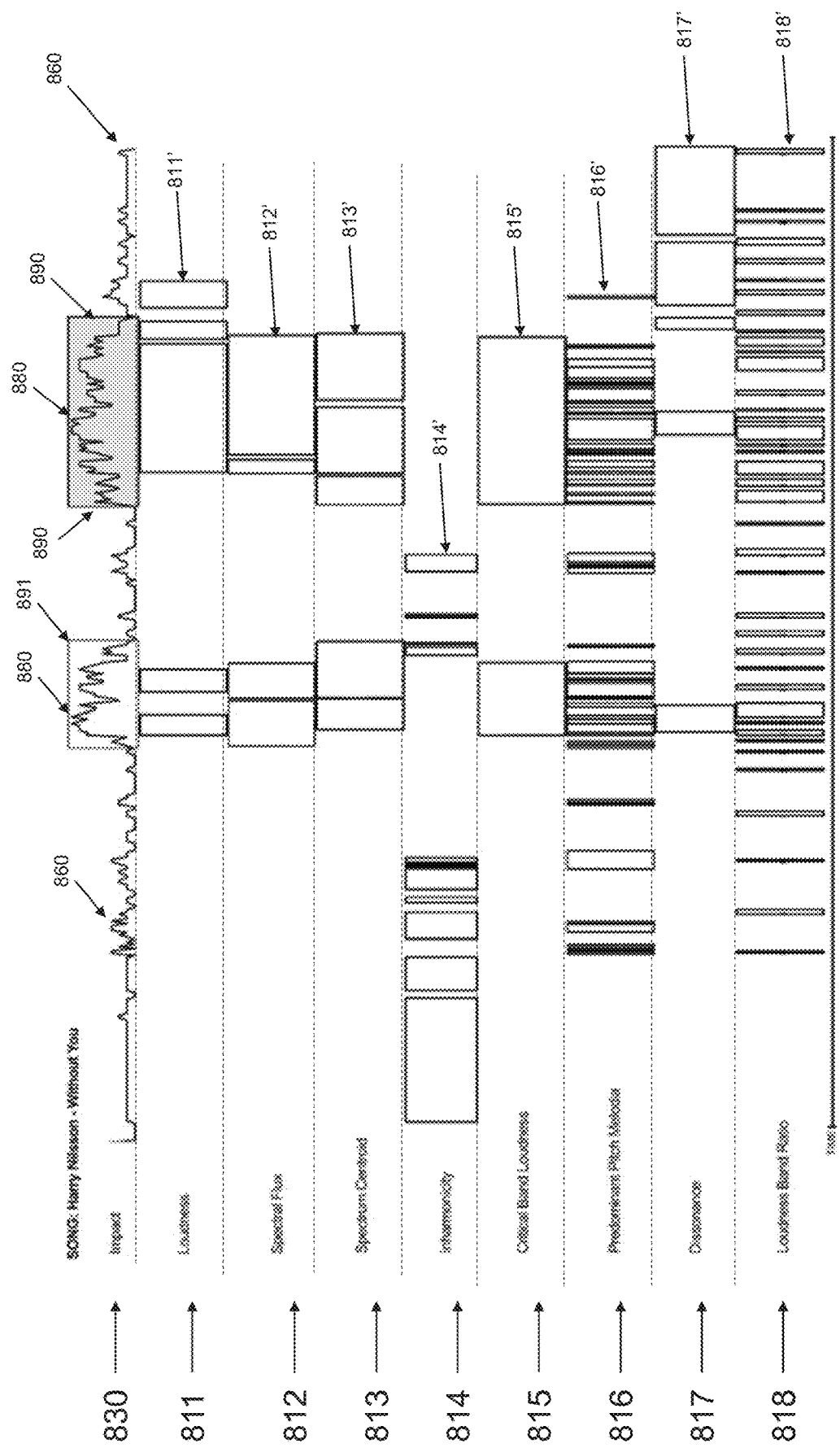
FIG. 8 is a group of plots generated using yet another song waveform as an input and showing detection outputs from a plurality of objective audio processing metrics based on the song waveform and an output from a combination algorithm based on the outputs of the plurality of objective audio processing metrics overlaid with an output of a phrase detection algorithm applied to the output of the combination algorithm.

FIGS. 7 and 8 each show an eight metric processing example according to embodiments of the present disclosure using different example audio files.

FIG. 3A is a graph 300 of audio data with time in seconds along the x-axis and amplitude along the y-axis. In FIG. 3A, the audio data presented is a visual illustration of a waveform encoded in a digital music file. Audio waveform data can be digitally represented by the amplitude of the audio signal's frequency in samples per second. This data can be either compressed or uncompressed, depending on the file type. FIG. 3A illustrates the audio data as a vector of amplitudes, where each value represents the original audio file's frequency value per sample. In the example audio file of FIG. 2, the audio data has a sampling rate of 44.1 kHz and a bit rate between 128 and 192.

FIG. 3B is a graph 311 of the output of an objective audio processing metric using the audio data of FIG. 3A as an input. In the example of FIG. 3B, the metric is the spectrum energy of beats in the audio signal across the whole spectrum and the graph 311 is a visual illustration of the output of a first objective audio processing metric 111 embodiment of the present disclosure. The data presented in FIB. 3B represents the general loudness for each beat of the audio waveform of FIG. 3A. From this data, an upper and a lower envelope can be generated based on a threshold 301. In FIG. 3B, the threshold 301 is the upper quartile of the amplitude and the segments which belong to this upper quartile are detected and saved as start and end time points of where the beats are for each detected segment. The upper quartile is a representative threshold, and other values are possible. Generally, a threshold 301 can be based on a relative value (e.g., a value based on the values of the data, such as an upper 20% of the average or 20% of the maximum value) or an absolute value (e.g., a value that does not change based on the data). Absolute values can be used, for example, when data is normalized as part of the metric (e.g., where output values of the metric are between 0 and 1), or where output values are frequency-dependent, as frequency is a more rigid parameter for recording audio data (e.g., sound amplitude can be scaled for given audio data without changing the nature of the data, such as turning up or down the volume, whereas absolute frequency is typically preserved during record and processing and typically cannot be changed without changing the nature of the data.) Increased loudness is one of the most basic chill response elicitors for listeners, and the start and end points for loudness can then be used as one set of inputs to a combination algorithm, which calculates the most impactful moments in the song of the audio waveform of FIG. 3A, as shown in more detail below. The output of the combination algorithm is also referred to herein interchangeably as chill moments data or a chill moments plot.

FIG. 3C is a set of three graphs 312*a-c* illustrating the output of a second objective audio processing metric 112 embodiment of the present disclosure run on the waveform of FIG. 3A. Each of the three graphs 312*a-c* illustrates the spectrum energy of beats in one of three different energy bands 312*a-c*, each represented by a frequency range in an audio signal (e.g., 20-400 Hz in the first graph 312*a*, 401-1600 Hz in the second graph 312*b*, and 1601-3200 Hz in the third graph 312*c*). The amplitude data in FIG. 3C illustrates the general loudness for each beat of the recording within the three energy bands as a ratio of total energy. In each energy band 312*a-c*, a threshold 302 is applied to generate a lower envelope. In FIG. 3C, the threshold 302 represents an upper quartile of the envelope data that can be calculated, and a post-processing routine is used to detect moments in the audio data where every band is below the threshold 302 for all the bands 312*a-c*. These detected moments are where there is a balance of frequencies and represents where all the 'instruments' in the music are playing all at once (e.g., ensemble vs solo). Because, for example, instrument entrances can elicit chill responses in listeners, the detected start and end points where the bands are all below the thresholds for all the bands are used to calculate the start and end points which are combined with the detected segments of the loudness metric processing output of FIG. 3B to be used as inputs for the combination algorithm, the output of which is presented in FIG. 3D and represents the song's most impactful moments based on the objective audio processing metrics of FIGS. 3B and 3C (e.g., spectrum energy per beat and concurrent spectrum energy per beat in three separate energy bands).

Additionally, while FIG. 3C shows a same threshold 302 applied to each energy band, in some instances, this threshold 302 is relative only to the values of the metric in each energy band (e.g., an upper 20% of the values in the first band 312*a*, instead of the upper 20% of the values in all bands 312*a-c*), and in other instances a different threshold is used in each energy band and could vary as a function of which bands are used and/or the number or size of individual bands. In some instances, a detection algorithm using the threshold 302 in each energy band 312*a-c* returns a positive detection when the threshold is met in any one band 312*a-c*, and in other instances the detection algorithm returns a positive detection where a respective threshold is met in all bands 312*a-c*, some bands 312*a-c*, most bands 312*a-c*, or any other combination thereof. Moreover, while the threshold has been discussed as being a 20% value relative to an average of the metric, this can, alternatively, be relative to a maximum and minimum. Also, while 20% (e.g., an upper quintile) is used throughout the disclosure, other threshold values are possible, such as an upper quartile, upper half, or more or less.

Generally, because the ultimate objective can be to find peak values relative to the song and across a combination of a plurality of different metrics, choosing too high (e.g., 0.1%) or too low (e.g., 80%) of a threshold will effectively negate the contribution of detections from the metric in the combination by making the detections too common or too infrequent. This is, in part, why one individual metric is unable to be robustly correlated with chill eliciting moments in real music. A balance between the strength of the correlation with any individual metric and the value of the threshold can be determined, however a more straightforward approach is to establish that a peak in any one metric is not necessarily a moment of maximum likelihood of eliciting chills because research indicates that one acoustic characteristic alone is not strongly predictive of eliciting the chills.

Rather, what the inventors have discovered and validated, is that it is the concurrence of relative elevations in individual metrics that is associated with acoustic moments that have the strongest characteristics suitable for inducing autonomic physiological responses in human listeners, and detecting these relative elevations is not strongly dependent on exact threshold values, but rather, more simply, requires that some to most of the elevations in each individual metric be detected throughout the entirety of a song, and this can be accomplished by a range of threshold values. For example, thresholds greater than 50% (e.g., the definition of elevated) and as high as 1% (e.g., moments totaling $\frac{1}{100}^{th}$ of the song), with this upper value based on the idea that any chill-inducing moment needs to last more than a few beats of music in order to even be registered and reacted to by the listener. Accordingly, if a very long piece of music is being processed, such as an entire symphony, $1/100^{th}$ of the song may still represent significantly more than a few beats, and thus a maximum threshold value is not able to be established, generally, for all complex audio data (e.g., both pop music and symphonies).

The detection algorithm 130 is the process of identifying the moments in the song where the metric's value is above the threshold and outputting these moments in a new dataset as positive detections during these moments.

FIG. 3D is an impact graph 330 of the output of a combination algorithm 140 run using the detections (e.g., GLIPhs, which are the segments in each metric output above the respective threshold) identified by the detection algorithm 130 in the outputs of the first and second audio processing algorithms of FIGS. 3B and 3C. FIG. 3D also includes the output of a phrase detection algorithm 150 based on the output of the combination algorithm. The example combination algorithm 140 used to generate the chill moments plot 360 of FIG. 3D operates by aggregating concurrences in the detections in outputs of the objective audio processing metrics of FIGS. 3B and 3C.

Example combination algorithms can work as follows: for each beat in the song, if the beat's loudness rises above the threshold for that feature in the metric (e.g., the detection algorithm returns a positive value for one or more beats or time segments in the loudness metric output of FIG. 3B), the combination algorithm adds 1*a weight to an aggregate value for each beat or time segment returned by the detection algorithm. Similarly, if the loudness per beat per band ratio value shows that the feature is below the threshold for that feature, then the metric can add 1*a weight for Loudness per beat per band ratio to the aggregate value. Each beat in the song is considered to be 'on' or 'off' for the metric and those binary features are multiplied by each metric's weight and added up for each beat. This is the general design of the combination algorithm regardless of the metrics being added. In FIG. 3D 4, the y-axis corresponds to values of 0, 1, and 2, where the weights for each metric are simply set to 1. The output of this process is the chill moments plot 360, which has a step-like presentation based on the per-beat time step. The combination algorithm can also generate a moving average 361 of the chill moments plot 360, which shows the value of the chill moments plot 360 across a few beats. Note that, in FIG. 3D, the chill moments plot 360 is normalized to range from 0 to 1 (from the original values of 0 to 2).

The phrase detection algorithm 150 can use the chill moments plot 360 as input to identify regions 380 in the time domain where both metrics are above their respective thresholds. In the simplest form, the phrase detection algorithm 150 returns these peaks regions 380 as phrases. However, multiple peak regions 380 clustered together are more correctly considered a single acoustic 'event' from the perspective of identifying impactful moments (or moments having characteristics suitable for inducing autonomic psychological responses) because two brief moments in music presented only a few beats apart are not processed by human listeners very independently. Accordingly, a more robust configuration of the phrase detection algorithm 150 can attempt to establish windows around groups of peak regions 380 and determine where one group of peak regions 380 becomes separate from another.

The phrase detection algorithm 150 configuration of FIG. 3D considers the moving average 361, as well as an upper bound 371 and a lower bound 372. The moving average 361 is separately normalized to set the peak 381 to "1." In FIG. 3D, the upper bound 371 is approximately 0.65 and the lower bound 371 is approximately 0.40 (relative to the normalized impact rating. In the phrase detection algorithm 150 configuration of FIG. 3D, a peak region 380 is considered part of an identified phrase 390 when the moving average 361 is above the upper bound 371. The phrase detection algorithm 150 then determines beginning and end points for each identified phrase 390 based on the time before and after the peak region(s) 380 where the moving average 361 drops below the lower bound 372. In some examples, only a single bound is used (e.g., the upper bound 371), and the values of the upper bound 371 and the lower bound 372 are, in part, dependent on the number of metrics used, the time-averaging length of the moving average 361, as well as the thresholds used for the individual metrics-because higher threshold values typically return shorter duration detection regions.

Notably, when a plurality of metrics are used (e.g., 8 or more), only one peak region 380 may exist and the value of the peak region 380 may not be a maximal impact rating (e.g., the peak region may correspond to a value of 7 out of a possible 8, assuming eight metrics and equal weightings). A peak region 380, therefore, need not be used at all by the phrase detection algorithm 150, which can instead rely entirely on the moving average 361 (or another time-smoothing function of the chill-moments plot 360) being above an upper bound 371 to establish a moment around which a phrase is to be identified. Also, while the use of additional metrics does not prevent the one or more peak regions 380 from being sufficiently isolated from other elevated regions of the chill moments plot 361 and/or of short enough duration such that the moving average 361 does not rise above the upper bound 371 and thus the phrase detection algorithm 150 does not identify a phrase around those one or more peak regions 380.

In some instances, and as shown in FIG. 3D, a small lead-in and/or lead-out time buffer can be added to the each identified phrase 390 such that, for example, a beginning or ending of the identified phrase 390 is only established when the moving average 361 is below the lower bound 372 for more than the lead-in or lead-out buffer, which accounts for the imprecision in capturing any musical 'build up' or 'let down' period before or after the identified phrase 390 by ensuring that at least a few beats before and/or after any impactful moment is captured in the identified phrase 390. Additionally, this can prevent brief dips in the moving average 361 bifurcating what might be subjectively considered a single impactful moment to a listener, though, as shown in FIG. 3D and discussed in more detail below, such a bifurcation is still seen in FIG. 3D, and can be detected and the split identified phrases 390 merged, if sufficiently close and/or if one if sufficiently short. In some examples, and as also discussed in more detail with respect to FIG. 5E, the phrase detection algorithm 150 can also dynamically adjust the length of the lead-in and/or lead-out time buffers based on a length of the identified phrase 390, a strength of or proximity to a peak in the chill moments plot 361 and/or the moving average 361, and/or an inflection of the moving average 361. In some instances, the start and stop moments of the identified phrase 390 can be triggered by the chill moments plot 360 dropping below a threshold value or to zero.

The phrase detection algorithm 150 can also identify a single primary phrase, as indicated in FIG. 3D as "Primary." The phrase detection algorithm 150 can identify a single primary phrase by, for example, comparing, for each identified phrase 390, the average of the chill moments plot 360 or the moving average 361 in each identified phrase 390 and/or the duration of the moving average 361 being above the upper boundary 371, with the identified phrase 390 having the higher value being identified as the primary phrase. Additionally, and as illustrated in FIG. 3D, two identified phrases 390 can be immediately adjacent to each other and can be combined into a single identified phrase 390 (as shown in FIG. 3E) in the output of the phrase detection algorithm 150.

The phrase detection algorithm 150 outputs the timestamps of the identified phrases 390, which can then be directly mapped onto the original audio waveform, as shown in FIG. 3E. FIG. 3E is a graph 340 of a waveform of FIG. 3A showing identified phrases 390 and their associated timestamps 398, 399.

FIGS. 4A-C illustrate how the chill moments plot 360 and identified phrases 390 of the audio sample of FIG. 3A change when a third objective audio processing metric is added-predominant pitch melodia. FIG. 4A is a graph 413 of an output of a predominant pitch melodia metric based on the waveform of FIG. 3A, that can be thresholded for use by the detection algorithm 130. FIG. 4A represents the predominant pitch value for each moment in time as a frequency value, and a confidence value (not illustrated in FIG. 4A, which represents how clearly the algorithm is seeing the predominant pitch). This new metric is created by multiplying the pitch frequency value by the confidence value. This data is then thresholded using the upper quartile (not illustrated) and in and out points are saved for the times around when the data is above the threshold, in the same manner as done for FIGS. 3A and 3B. Predominant pitch melodia is designed to find the places in which the melody is 'highest' and 'strongest' because composers and musicians often bring the melody higher throughout the performance as a way of calling attention to the melody and higher pitches are known to elicit chill responses in listeners. The thresholded detection for the pitch melodia output is based on the multiplication of the pitch frequency times the confidence value, which is then normalized and thresholded using, for example, an upper quartile. The start and end points from the detection algorithm 130 are then aggregated into the combination algorithm 140 in the same way the metrics of FIGS. 3A and 3B were, and the phrase detection algorithm 150 was re-run, generating the chill moments plot 460, moving average 461, and identified phrases 490 of the impact graph 431 FIG. 4B. In the impact graph 431 of FIG. 4B, the y-axis values are normalized to 0 to 1 from 0, 1, 2, 3 to reflect the addition of a third metric. The resultant identified phrases 490 are mapped onto the audio waveform in FIG. 4C, which also shows a comparison between the timestamps 498, 499 of the identified phrases 490 to the timestamps 398, 399 of the identified phrases 390 using only two metrics (as shown in FIG. 3E). The addition of the third metric did not substantively change the location of the peaks 381, 481 in the moving average 361, 461, but the duration of both identified phrases 390 shrunk slightly, which can indicate an improved accuracy in the detection of the most impactful moments. In addition, the highest peak 481 in the moving average 461 of FIG. 4B has a higher prominence over adjacent peaks than does the highest peak 381 in the moving average 361 of FIG. 3D, which also can indicate an improved confidence in the temporal location of this particular impactful moment.

Because chill elicitors such as relative loudness, instrument entrances and exits, and rising relative pitch have some degree of universality in terms of creating a physiological response in humans, examples of the present disclosure are able to use, in some instances, minimum combinations of two metrics to robustly identify suitable segments across essentially all types and genres of music. Studies have shown that music is unmediated—it is an unconscious process. A listener does not have to understand the language being used in the lyrics nor do they have to be from the culture where the music comes from to have a response to it. The algorithms disclosed are primarily acoustically focused on auditory features shown to elicit physiological responses which activate the reward centers in humans which are largely universal, and the diversity in the auditory features identified by the algorithms enables a concurrence of even two of their resultant metrics to able to identify music segments having characteristics suitable for inducing autonomic physiological responses across essentially all genres of music.

FIG. 5A is a graph 500 of a waveform of a different digital music file. FIG. 5B is a graph 511 of the output from a loudness metric on the waveform input of FIG. 5A and shows a corresponding threshold 501 for use in a detection algorithm 130. FIG. 5C is a graph 513 of the output from a loudness band ratio metric on the same input waveform of FIG. 5A in three different energy bands $512z$, $512b$, $512c$, with respective thresholds 502 for use in a detection algorithm 130. FIG. 5D is a graph of the output from predominant pitch melodia metric, with respective thresholds 503 for use in a detection algorithm 130.

FIG. 5E is a graph 530 showing the chill moments plot 560 output from a combination algorithm 140 using the detections of the metrics of FIGS. 5B-5C as inputs and also shows a moving average 561 of the chill moments plot 560. Similar to the results of FIGS. 3D and 4B, peaks 480 in the chill moments plot 560 and peaks 481 in the moving average 561 are present and where the moving average 561 is above an upper bound 571, the phrase identification algorithm 150 has generated identified phrases 590. In the configuration of the phrase identification algorithm 150 of FIG. 5E, the start and end points of each identified phrases 590 is determined by inflection points 592 in the moving average 561 before and after the locations 591 where the moving average 561 drops below the lower bound 572. FIG. 5E shows the timestamps 597, 598, 599 that are output by the phrase identification algorithm 150 for each identified phrase. The phrase identification algorithm 150 in FIG. 5E has also classified the third phrase as "Primary," which can be done as a function the duration of the moving average 561 or chill moments plot 560 above either of the upper or lower bound 571, 572, and/or based on the average of the moving average 561 or chill moments plot 560 between the inflections 592 and/or the locations 591 where the moving average 561 drops below the lower bound 572. In some instances, but not as shown, the phrase identification algorithm 150 can subsequently enforce a minimum length on the primary phrase, such as 30 seconds, which can, as shown in other examples herein, result in the primary phrase overlapping other phrases. The phrase identification algorithm 150 can extend the length of a phrase in different ways, for example, equally in both directions or preferentially in a direction where the values of the moving average 561 or chill moments plot 560 are higher.

Generally, the time-length of these windows 590 can correspond to a number of factors, such as a predetermined minimum or maximum, to capture adjacent detection if they occur within a maximum time characteristic, or other detection characteristics, such as increased frequency/density of two of the three metrics reaching their criteria. Additionally, while FIG. 5E illustrates an example using three metrics, examples of the present disclosure include dynamically adding (or removing) metrics as inputs to the combination algorithm 140 in response to any of the features of the graph 530, such as the number or length of identified phrases 590, the values and or characteristics (e.g., rate change) of the moving average 561 or chill moments plot 560 in the graph 530 and/or in the identified phrases 590. For example, if a three-metric calculation returns 3 phrases, and adding one or two more metrics reduces this detection to two phrases, the two-phrase output can be used.

FIG. 5E illustrates a three-metric combination based on respective criteria for each metric, two-metric and four-metric (or more) combinations are considered, and some examples include tailoring the respective detection criteria of each metric based on the number of metrics used in the combination. For example, if only two metrics are combined, their respective criteria can be tightened (e.g., decrease a threshold percentile relative to the overall metric output), in order to more clearly enable detections to be identified in the combination algorithm. Conversely, if three or more metrics are combined, each respective detection criteria can be loosened (e.g., increase a threshold percentile relative to the overall metric output), in order to enable the concurrence of the multiple metrics to be more easily identified by the combination algorithm. Alternatively, combining each metric can include assigning a weight to each metric. In the examples presented herein, each metric is combined with a weight of 1.0, that is, a detection in each metric is added as a 1 in the combination algorithm 150, however other values are possible and can be assigned based on the individual metrics being combined or dynamically based on, for example, a genre of music or the output of the respective audio processing metric or any of the outputs from other metrics to be used in the combination algorithm.

Examples also include running a plurality of metrics (e.g., 12 or more) and generating a matrix combination of all possible or more combinations. While the configuration of the presently described system and methods are configured to make such a matrix unnecessary (e.g., if chill eliciting features exist in an audio signal they are extremely likely to be easily identified using any combination of metrics, so long as those metrics are correctly associated with chill-eliciting acoustic features), as an academic exercise it may be useful to locate individual peak moments 581 as precisely as possible (e.g., within 1 or 2 beats), and the exact location can be sensitivity to the number and choice of metrics. Accordingly, with a matrix combination of all possible combinations, the combination can either be averaged itself or trimmed of outliers and then averaged (the result of which may be effectively identical) to identify individual peak moments. Additionally, the phrase identification algorithm 150 could be run on this matrix output, though, again this result may not be meaningfully different from just using all metrics in a single combination with the combination algorithm 140 or from using a smaller subset of metrics (e.g., 3, as shown in FIG. 5E).

Generally, this is likely to be a question of processing power. If, for example, one million songs of a music catalog are to be processed according to examples of the present disclosure, the choice of using 3 or 12 metrics can result in a substantial difference in processing time and money. Hence, dynamically adjusting the number of metrics can be most efficient, if, for example, the combination algorithm 140 is first run on a combination of 3 metrics, and then, if certain conditions are met (e.g., lack of prominence in the peaks 581) a h metric can be run on-demand and added to determine if this achieves a desired confidence in the location of the peaks 481. If, of course, processing power is a non-issue, running 8 or 12 metrics on all $4^{th}$ million songs may provide the 'best' data, even if the effective results (e.g., timestamps of the identified phrases 590) are not meaningfully different from results generated with 3 or 4 metrics. Accordingly, examples of the present disclosure can include a hierarchy or priority list of metrics based on a measured strength of their observed agreement with the results of their combination with other metrics. This can be established on a per-genre basis (or any other separation) by, for example, running a representative sample of music from a genre though a full set of 12 metrics, and then, with a matrix of all possible combinations, establishing a hierarchy of those metrics based on their agreement with the results. This can be established as a subset of less than 12 metrics to be used when processing other music from that genre. Alternatively, or in addition, the respective weights of the detections from each metric can be adjusted in a similar manner if, for example, the use of all 12 metrics is to be maintained for all genres, but each having a unique set of weights based on their identified agreement with the matrix results.

FIG. 5F shows the identified phrases 590 and their associated timestamps 597, 598, 599 from FIG. 5E displayed over the original waveform of FIG. 5A.

FIG. 6A-6C illustrate how the addition of another suitable audio processing metric (e.g., a metric associated from the same phenomena as the others, in this case, chill-eliciting acoustic characteristics) may not substantially change the result. FIG. 6A is a plot 614 of the output another suitable processing metric, spectral flux, using the waveform of FIG. 5A as an input and an associated threshold 604. FIG. 6B is a graph 613 of the combination algorithm 140 and phrase identification algorithm 150 re-run on the detection from the metrics of FIGS. 5B-5D, with the addition of the detection from the spectral flux metric of FIG. 6A. FIG. 6B shows the resulting chill moments plot 660, moving average 691, their respective peaks 680, 681, and the indented phrases 690, including their respective time stamps 697, 698, 699, start/stop points 692 (e.g., inflections in the moving average 690 before or after the locations 691 where the moving average drops below the lower bound 572).

FIG. 6C is a plot 640 of the waveform of FIG. 5A with the updated identified phrases of FIG. 6B. FIG. 6C also shows a comparison between the timestamps 697, 698, 699 of the updated phrases and the original timestamps 597, 598, 599 of the 3-metric output result of FIG. 5F. In FIG. 6C, the identified phrases 690 are generally aligned with the identified phrases 590 of FIG. 5E, as indicated by their detection lengths being almost identical. The length of the primary phrase is shortened due to the introduction of a very slight inflection (as indicated by 692' in FIG. 6B) in the moving average 661 that was not present in the 3-metric result. Generally, this is an example of how the addition of a metric can slightly change the length of phrases by introducing more variability of the data, without meaningfully changing the location of the phrase as capturing peak events. However, the location of the peak 681 in the primary phrase has changed, as shown in a comparison between FIGS. 5E and 6B, which indicates that while the confidence in the location of the identified phrases 590 is high, additional metrics may be needed if an accurate location of the exact peak moment of impact 581, 681 is desired. Note, however, the location of the peaks in the other non-primary phrases did not meaningfully change between FIG. 5E and FIG. 6B.

In some examples, the identification of which window is a primary window can be based on a number of factors, such as frequency and strength of detections in the identified segment and the identification of a primary segment can vary when, for example, two of the identified windows are substantially similar in detection strength (e.g., detection frequency in the identified window) and the swapping of one metric for another subtly changes the balance of the detection in each window without changing the detection of the window itself. Furthermore, in the cases when adding a metric doesn't substantially change the result for a specific song, some metrics will increase the effectiveness (e.g., robustness) across many songs. Thus, adding spectral flux, for example, may not change the results of one particular song in a particular genre, but may improve the confidence in selection of chill phrases substantially in a different genre.

FIG. 7 is a group of plots 730, 711-718 generated using yet another song waveform as an input and showing detection outputs from a plurality of objective audio processing metrics based on the song waveform and an output from a combination algorithm based on outputs of the plurality of objective audio processing metrics overlaid with an output of a phrase detection algorithm applied to the output of the combination algorithm. In FIG. 8 the audio waveform was from a digital copy of the song "Bad to Me" by Billy J Kramer. The impact graph 730 shows a chill moments plot 760 and associated peaks 780, with primary phrase 790 and secondary phrase 791 identified in the chill moments plot 760 by a phrase identification algorithm example. FIG. 7 also shows individual detection plots 711-718 from the eight objective audio processing metrics used as inputs to the combination algorithm for generating the impact graph 730. The eight objective audio processing metric plots are loudness 818, spectral flux 712, spectrum centroid 713, inharmonicity 714, critical band loudness 815, predominant pitch melodia 716, dissonance 717, and loudness band ratio 718. In operation, each of the eight objective audio processing metrics was processed to generate GLIPhs (e.g., using respective thresholds) and the GLIPhs were converted into binary detection segments, as shown in the metric's corresponding detection plot 711-718. The binary detection segments were aggregated using a combination algorithm to generate the chill moments plot 760 in the impact graph 730.

Advantageously, examples of the combination algorithm disclosed herein enable the combination of all of the individual detections from these eight audio processing algorithms to create a combination algorithm that can identify the segments or moments in the audio waveform having the audio characteristics suitable for inducing autonomic physiological responses, as described above. In the present example of FIG. 7, the chill moments plot 760 of the impact graph 730 was generated using an equal weighted combination of the detections of each audio processing algorithm (e.g., as indicated in plots 711-718), and a peak moment 780 was identified from the combination algorithm containing the highest additive value in the chill moments plot 760. This peak moment 780 is bounded by the smaller inner-window 790 drawn within the shaded region, which represents an identified segment. The length of this segment can be determined in a number of ways to include one or more regions of maximum detection value, and here only a singular maximum detection peak 780 is present in the impact plot 730, and the inner-window 790 extends between adjacent local minima in the chill moments plot 760 to define the identified segment 790, with the larger gray window 791 representing the application of a time-based minimum segment length that extends the inner window to a 30-second window.

Because each of the audio processing algorithms of FIG. 7 is representative of one or more of the audio characteristics known to be associated with inducing autonomic physiological responses, the combination of detection regions 711'-718' from the outputs 711-718 from each audio processing algorithm, with equal weighting, as shown in the example of FIG. 7, enables the present combination output 760 (and the resulting impact graph 730) to robustly identify the most 'impactful' moment in audio waveforms across diverse genres of music, where this identified impactful moment has the strongest characteristic suitable for inducing an autonomic physiological response in a listener, based on the audio characteristics detectable by each audio processing algorithm being equally responsible for causing an autonomic physiological response (e.g., having their detected concurrences added with equal weighting). This is in part based on the state of prior and ongoing research discussed in more detail below, which a) uses examples of the present disclosure to determine correlations with brain activity and the identified peaks in combination plots using equal weights, b) has shown equal-weighting to generate extremely strong correlations between identified segments and peak brain activity of subjects listening to the music, and c) is evidence of equal weightings being sufficient to identify moments having the strongest characteristic suitable for inducing an autonomic physiological response in a listener. Moreover, a distinct advantage of the present disclosure is that, due to the complexity of music, equal weighting, as well as using a set of audio processing algorithms sufficient for detecting a wide range of possible audio characteristics (of the desired type, discussed above), enables the present routine to be useful across the widest range of music genres and types. Conversely, weighting of the metrics, as well as adjustment of the individual threshold criteria used to generate the detection regions, can further tailor examples of the present disclosure to be more sensitive to certain genres of music.

Examples of the present disclosure also include making adjustments in each metric to (1) the weighting of the detections in the outputs from each audio processing algorithm, (2) the detection threshold criteria (individually or across all the audio processing algorithms), and/or (3) a time-minimum length of the detections based on the genre or type of music. These example adjustments are possible without compromising the overall robustness of the output, due to the similarities between music of same or similar genres with respect to which audio processing algorithms are more likely to be coordinated with each other (e.g., likely to generate peaks in the Impact plot, causing an identification) vs. uncoordinated, where detections in one or more audio processing algorithms are unlikely to be concurrent with any detections in the other audio processing algorithms. In the present example of FIG. 7, the detections 714' of the Inharmonicity metric shown in plot 714 are very weakly correlated with any other detections in the outputs of the other audio processing algorithms. If this lack of correlation of these detections 714' is associated with this genre of music, increasing the detection criteria of the outlier metric and/or reducing the weighting of the detection segments 714' of the plot 714 can increase the fidelity of the resultant identification (e.g., peak 780 and segment 790) in the impact plot 730.

FIG. 8 is a group of plots 830, 811-818 generated using yet another song waveform as an input and showing detection outputs from a plurality of objective audio processing metrics based on the song waveform and an output from a combination algorithm based on outputs of the plurality of objective audio processing metrics overlaid with an output of a phrase detection algorithm applied to the output of the combination algorithm. In FIG. 8 the audio waveform is from a digital copy of the song "Without You" by Harry Nilsson. The impact graph 830 shows a chill moments plot 860 with a primary phrase 890 and secondary phrase 890 identified in the chill moments plot 860 by a phrase identification algorithm example. FIG. 8 also shows individual detection plots 811-818 from the eight objective audio processing metrics used as inputs to the combination algorithm for generating the impact graph 830. The eight objective audio processing metric plots are loudness 818, spectral flux 812, spectrum centroid 813, inharmonicity 814, critical band loudness 815, predominant pitch melodia 816, dissonance 817, and loudness band ratio 818. In operation, each of the eight objective audio processing metrics was processed to generate GLIPhs (e.g., using respective thresholds) and the GLIPhs were converted into binary detection segments, as shown in the metric's corresponding detection plot 811-818. The binary detection segments were aggregated using a combination algorithm to generate the chill moments plot 860 in the impact graph 830.

In the impact graph 830, both the primary and secondary phrases 890, 891 have peaks 880 in the chill moments plot 860 of equal maximum value. The primary phrase 890 is determined here by having a longer duration of the chill moments plot 860 at the peak value 880, and accordingly received a 30-second fixed-length window, and the secondary phrase 891 received a widow sized by expanding the window from the identified peak 880 to local minima in the chill moments plot 860. Other criteria for expanding the phrase window around an identified moment can be used, such as evaluating the local rate-change of the chill moments plot 860 of the change in the running average before and after the identified moment and/or evaluating the strength of adjacent peaks in the chill moments plot 860 to extend the window to capture nearby regions of the waveform having strong characteristics suitable for inducing an autonomic physiological response in a listener. This method generates a window having the highest possible overall average impact within a certain minimum and maximum time window.

Impact Curve Taxonomy

Figure 9A:
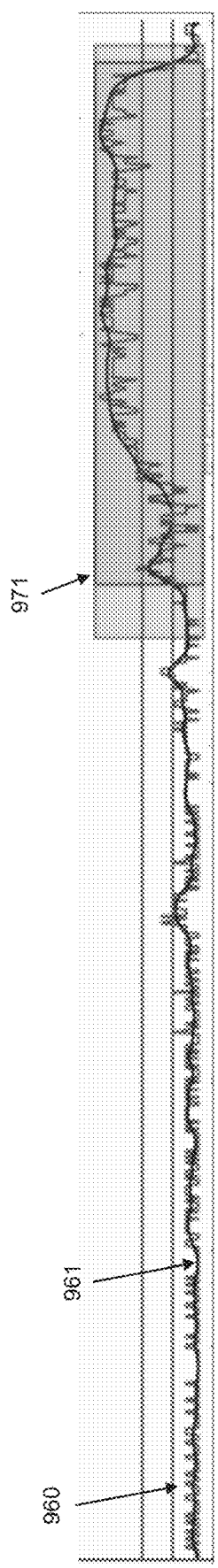
FIGS. 9A-9D are output plots from a combination algorithm run on objective audio metric outputs of four different songs.
Figure 9B:
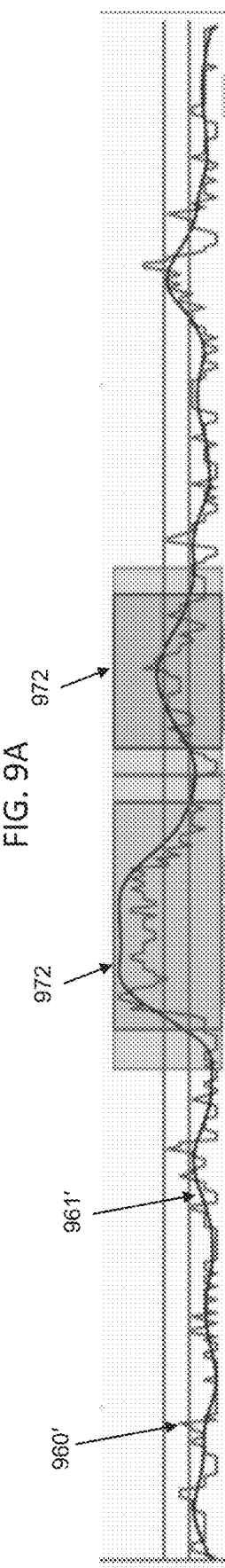
Figure 9C:
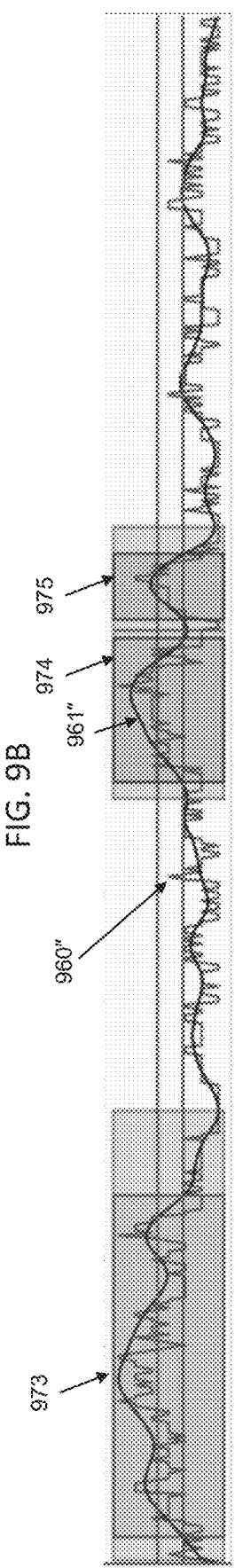
Figure 9D:
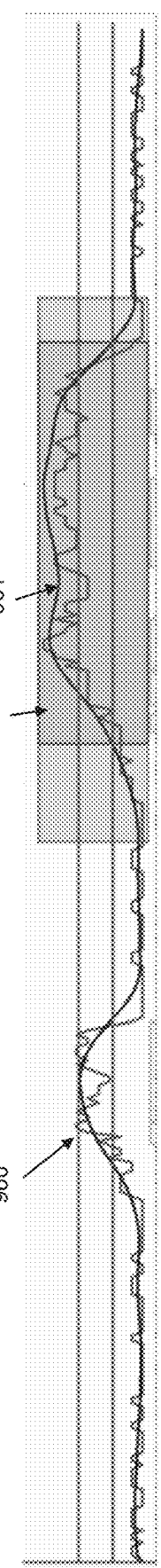

Examples of the present disclosure also include musical taxonomy created with embodiments of the chill moments plot data described herein. This taxonomy can be based on, for example, where the areas of highest or lowest impact occur within a song or any aspect of the shape of the chill moments plot. Four examples are provided in FIGS. 9A-9D. FIGS. 9A-9D shows different chill moments plots (stepped line) 960, 960', 960", 960''' with a moving average (smooth line) 961, 961', 961", 961''' as well as windows 971-976 indicating identified chill moment segments in the four different songs. FIG. 9A is "Stairway to Heaven" by Lez Zeppelin, FIG. 9B is "Every Breath You Take" by The Police, FIG. 9C is "Pure Souls" by Kanye West, and FIG. 9D is "Creep" by Radiohead. Examples of the present disclosure include systems and methods for classifying various examples of the chill moments plot, moving average, and identified phrases to generate a searchable impact curve taxonomy that enables searching for music based on the impact taxonomy of a song. Example searches include peak locations of the chill moments plot or the moving average, phrase location and duration, variability in the chill moments plot or the moving average, or other properties related to the concurrence of chill producing elements. It also enables media producers to match a song's impact contours with synced media, such as in the case of video commercials or feature films.

Objective Audio Processing Metrics

Examples of the present disclosure provide for an audio processing routine that combines the outputs of two or more objective audio metrics into a single audio metric, referred to herein as a chill moments plot. However, the name 'chill moments plot' refers to the ability of examples of the present disclosure to detect the moments in complex audio data (e.g., music) that have characteristics suitable for inducing autonomic physiological responses in human listeners—known as 'the chills'. The ability of the audio processing examples of the present disclosure to detect the moments having these characteristics is a function of both the metrics chosen and the processing of the output of those metrics. Therefore, some choices of metrics and/or some configurations of the detection and combination algorithms will increase or reduce the strength of the detection of characteristics suitable for inducing autonomic physiological responses in human listeners, or even detect for other characteristics. The simplest example of detecting other characteristics comes by inverting the detection algorithms (e.g., the application of thresholds to the outputs of the objective audio processing metrics) or the combination algorithm. Inverting the detection algorithms (e.g., detecting a positive as being below a lower 20% threshold instead of as above an upper 20%) generally identifies moments in each metric that have the least association with inducing chills and processing the concurrence of these detections with the combination algorithm will return peak concurrences for moments having the weakest characteristics suitable for inducing autonomic physiological responses in human listeners. Alternatively, without changing the operation of the detection algorithms, minima in the combination algorithm output can also generally represent moments having the weakest characteristics suitable for inducing autonomic physiological responses in human listeners, though possibly with less accuracy than if a lower threshold is used for detection in each metric's output. Accordingly, this inversion is possible when metrics are used that individually correspond to acoustic features known to be associated with inducing autonomic physiological responses in human listeners.

Alternatively, other metrics can be used that have different associations. For example, a set of two or more metrics that are associated with acoustic complexity or, inversely, acoustic simplicity. In these two examples, the combination algorithm could robustly detect peak moments or phrases of acoustic complexity or simplicity. However, overall complexity or simplicity may lack a robust definition that applies across all types and genres of music—this can make the selection of individual metrics difficult. Regardless, examples of the present disclosure provide for ways to utilize multiple different objective audio processing metrics to generate a combined metric that accounts for concurrent contributions across multiple metrics.

In contrast to more nebulous, or even subjective, acoustic descriptions such as complexity or simplicity, a listener experience of an autonomic physiological response when listening to music is a well-defined test for overall assessment, even if such events are not common: a listener either experiences a chills effect while listening to a song or they do not. This binary test has enabled research into the phenomenon to establish verifiable connections between acoustic characteristics and the likelihood of a listener experiencing an autonomic physiological response. This research, and the associated quantifiable acoustic characteristics, helps to establish a set of metrics to consider as being relevant to the present objective of determining, without human assessment, the moment or moments in any song having characteristics most suitable for inducing autonomic physiological responses. Moreover, both the complexity and diversity of music make it unlikely that any one objective audio processing metric alone could be reliably and significantly correlated with peak chill-inducing moments in music. The inventors of the present disclosure have discovered that concurrences in relatively-elevated (e.g., not necessarily the maximum) events in multiple metrics associated with chill-inducing characteristics can solve the problems associated with any single metric and robustly identify individual moments and associated phrases in complex audio signals (e.g., music) that have the strongest characteristics suitable for inducing autonomic physiological responses in human listeners. Based on this, a combination algorithm (as discussed herein) was developed to combine the inputs from two or more individual objective audio processing metrics which can be, for example, to identify acoustic characteristics associated with a potential listener's experience of the chills.

Examples of the present disclosure include the use of objective audio processing metrics related to acoustic features found in the digital recordings of songs. This process does not rely on data from outside sources, e.g. lyrical content from a lyric database. The underlying objective audio processing metrics must be calculable and concrete in that there must be an 'effective method' for calculating the metric. For example, there are many known effective methods for extracting pitch melody information from recorded music saved as a .wav file or any file that can be converted to a .wav file. In that case, the method may rely upon pitch information and specifically search for pitch melody information that is known to elicit chills.

The objective audio processing metrics capable, in combination, to detect chills can rely upon social consensus to determine those elicitors known to create chills. These are currently drawn from scientific studies of chills, expert knowledge from music composers and producers, and expert knowledge from musicians. Many of these are generally known, e.g., sudden loudness or pitch melody. When the goal is to identify impactful musical moments, any objective audio processing metrics that are known to represent (or can empirically be shown to represent through experimentation) a connection to positive human responses, can be included in the algorithmic approach described herein. Representative example metrics that are objectively well-defined include loudness, loudness band ratio, critical band loudness, melody, inharmonicity, dissonance, spectral centroid, spectral flux, key changes (e.g., modulations), sudden loudness increase (e.g., crescendos), sustained pitch, and harmonic peaks ratio. Examples of the present disclosure include any two or more of these example metrics as inputs to the combination algorithm. The use of more than two of these example metrics generally improves the detection of the most impactful moments in most music.

Generally, the use of more than two metrics provides improved detection across a wider variety of music, as certain genres of music have common acoustic signatures and, within such a genre, concurrences in two or three metrics may be equally as good as using eight or more. However, in other genres, especially those where the acoustic signatures associated with those two or three metric metrics are uncommon or not very dynamic, adding additional metrics can provide a more significant benefit. Adding additional metrics may dilute or reduce the effectiveness of the combination algorithm in some specific types of music, but so long as the added metrics are measuring acoustic characteristics that are both distinct from the other metrics and associated with inducing the chill phenomenon in listeners, their inclusion will increase the overall performance of the combination algorithm across all music types. All of the example metrics presented above satisfy this criteria when used in any combination, but this does not preclude any one metric from being replaced with another if it satisfies the criteria. In addition, given the similarities that exist within certain genres of music, examples of the present disclosure include both preselecting the use of certain metrics when a genre of music is known and/or applying uneven weightings to the detections of each metrics. Examples can also include analyzing the outputs of individual metrics As an extreme example, music from a solo vocalist may simply lack the instrumentation to generate meaningful data from certain metrics (e.g., dissonance) and thus the unaltered presence of detections from these metrics add a type of random noise onto the output of the combination algorithm. Even if multiple metrics are adding this type of noise to the combination algorithm, so long as two or three relevant metrics are used (e.g., measuring acoustic characteristics that are actually in the music), concurrent detections are extremely likely to be detected above the noise. However, it is also possible to ascertain when a given metric is providing random or very low strength detections and the metric's contribution to the combination algorithm can be reduced by lowering its relative weighting based on the likelihood that the output is not meaningful or their contribution can be removed entirely if a high enough confidence of its lack of contribution can be established.

There are also many qualities that have been identified as being associated with chills which have no commonly known effective objective detection method. For example, virtuosity is known to be a chill elicitor for music. Virtuosity is generally considered to have aesthetic features related to the skill of the performer, but there are no well-defined 'effective methods' for computing identifiable sections within musical recordings which qualify as exemplifying such a subjective value as 'virtuosity'. Also, testing the efficacy of a 'virtuosity-identifying' algorithm could prove to be difficult or impossible.

The general method of using concurrent elicitors applies to any specific use case. Consider the case of identifying irritating or annoying portions of musical recordings (for use cases in avoiding playing music that matches these qualities for example), where, as a first step, it would be necessary to conceptually identify what irritating or annoying means in aesthetic terms, and then create effective statistical methods for identifying those features. Those features can then be aggregated through the methods described herein and progressively more-effective means of identifying the types of portions can be built through expanding the metrics used, tuning their thresholds for detections, and/or adjusting their relative detection weights prior to being combined according to examples of the combination algorithm.

Example of the present disclosure can include additional detection metrics not illustrated in the present figures. Examples include sudden dynamic increase/crescendos, sustained pitch, harmonic peaks ratio, and chord changes/modulations.

Sudden dynamic increase/crescendos: Examples include first finding the $1^{st}$ derivative of loudness as a representation of the changes in loudness, and using thresholds and a detection algorithm to identify GLIPhs around the regions where the $1^{st}$ derivative is greater than the median and also where the peak of the region of the $1^{st}$ derivative exceeds the median plus the standard deviation.

Sustained pitch: Examples include a detection algorithm to identify GLIPh regions where the predominant pitch confidence values and pitch values are analyzed to highlight specific areas where long sustained notes are being held in the primary melody. The detection metric in this case involves highlighting regions where the pitch frequency has low variance and exceeds a chosen duration requirement (e.g. longer than 1 second).

Harmonic peaks ratio: Examples include a detection algorithm to identify GLIPh regions where the ratio of the base harmonics are compared to the peak harmonics to find sections where the dominant harmonics are not the first, second, third or fourth harmonics. These sections highlight timbral properties that correlate with chill inducing music. The detection metric in this case involves only selecting regions which conform to specific ratios of harmonics in the signal. For example, selecting regions where the first harmonic is dominant compared to all the other harmonics would highlight regions with a specific type of timbral quality. Likewise, selecting regions where the upper harmonics dominate represent another type of timbral quality.

Key changes/modulations: Examples include using a detection algorithm to identify GLIPh regions where the predominant chords shift dramatically, relative to the predominant chords established in the beginning of the song. This shift indicates a key change or a significant chord modulation. The detection metric in this case does not involve a threshold and directly detects musical key changes.

Experimental Validations

In two separate investigations, the chill phenomenon (e.g., the autonomous physiological response associated with the acoustic characteristics analyzed by examples of the present disclosure) was investigated by comparing the data from the output of example implementations of the present disclosure to both the brain activations and listeners' behavioral responses.

In both studies, the implemented configuration of the algorithm was the same. To produce prediction data, a chill moments plot was generated using a combination algorithm run using the GLIPh detections of eight objective audio processing metrics as inputs. The nature of the eight objective audio processing metrics that were use are described in earlier sections. Specifically for the experimental validation studied described herein, the eight objective audio processing metrics used were: loudness, critical band loudness, loudness band ratio, spectral flux, spectrum centroid, predominant pitch melodia, inharmonicity, and dissonance, which are the eight metrics illustrated in FIGS. 7 and 8.

In the same fashion as described in previous sections, the eight objective audio processing metrics were applied individually to a digital recording and a respective threshold for the output of each metric was used to produce a set of detections (e.g., GLIPhs) for each metric. The sets of detections were combined using a combination algorithm embodiment of the present disclosure to produce a chill moments dataset, that included a moving average of the output of the combination algorithm to present a continuous graph of the relative impact within the song using for comparison. The moving average of the output of the combination algorithm produced for a recording was compared to the temporal data gathered from human subjects listening to the same song in a behavioral study and, separately, in an fMRI study.

Behavioral Study

A behavioral study was conducted to validate the ability of examples of the present disclosure to detect peak impactful (e.g., highest relative likelihood of inducing an autonomic physiological response) moments and, generally, to validate the ability of examples of the present disclosure to predict a listener's subjective assessment of a song's impactful characteristics while listening. In the behavioral study, from a list of 100 songs participants listened to self-selected, chill-eliciting musical recordings (e.g., songs selected by users who were asked to pick a song they knew that had or could give them the chills) while moving an on-screen slider in real time to indicate their synchronous perception of the song's musical impact (lowest impact to highest impact). The music selected by participants was generally modern popular music, and the selected songs ranged roughly from 3 to 6 minutes in length. The slider data for each participant was cross-correlated with the output for each song as generated by the output of a combination algorithm run on the outputs of the eight objective audio processing metrics where the participant's selected song was used as an input.

Figure 10A:
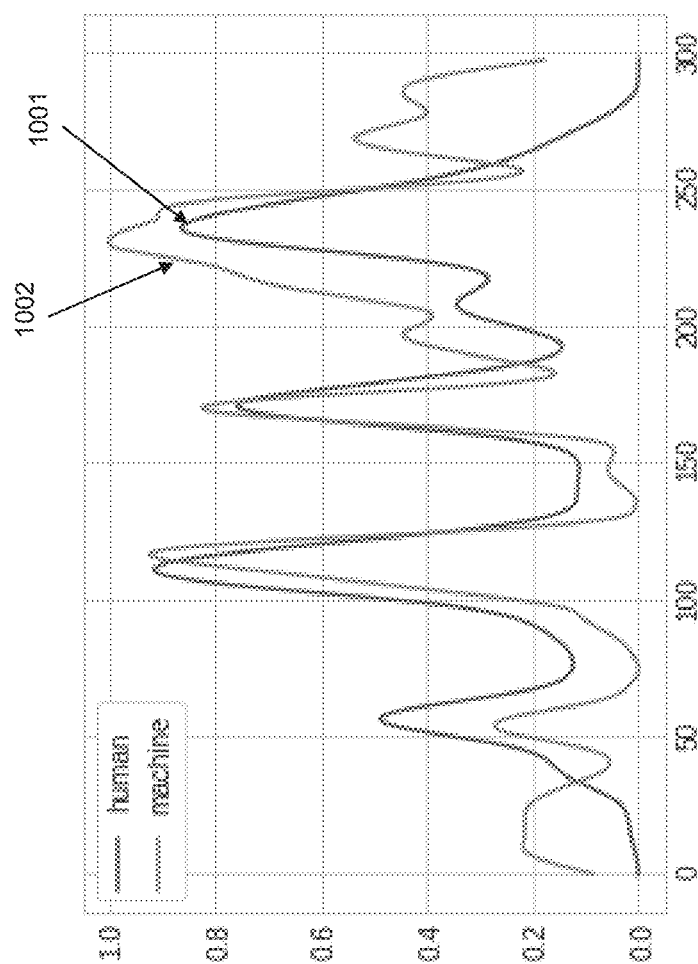
FIG. 10A is a graph of an example of subject data from a behavioral study.

The behavioral study was conducted using 1,500 participations. The participants' responses were significantly correlated with the prediction of the combination algorithm for the respective song. Participants indicated higher impact during phrases predicted to be chill-eliciting by the combination algorithm. In FIG. 10A, a graph plotting the results of a participant's slider data 1001 (labeled as 'human') is superimposed onto the moving average of the combination algorithm output 1002 (labeled as 'machine'). In the result of FIG. 10A, participant Number 8 was listening to the song Fancy by Reba McEntire.

Using the 1,500 participant's continuous slider-data received during their listening of their selected song, Pearson's correlation coefficients were produced from the slider data and the moving average of the combination algorithm's output. Table 1 presents the Pearson correlation coefficients for each of the 34 songs chosen by the 1,500 participants (many participants chose the same songs). The aggregate Pearson correlation coefficient for the 1,500 participants was 0.52, with a probability (p value) of less than 0.001. In other words, the strongest possible statistical evidence was obtained showing that the combination algorithm using detections from eight objective audio processing metrics was able to predict impactful moments in music, as judged by real human listeners.

TABLE 1

Individual Pearson Correlation values and total aggregate average correlation value

| Participant ID | Song | Pearson coeff |
| --- | --- | --- |
| 0 | Dizzy | 0.34 |
| 1 | Tequila | 0.76 |
| 2 | ChasingCars | 0.8 |
| 3 | Living On A Prayer | 0.77 |
| 4 | They Can't Take That Away From Me | 0.43 |
| 5 | Groove Is In The Heart | 0.34 |
| 6 | Safe and Sound | 0.72 |
| 7 | Walking On Sunshine | 0.66 |
| 8 | Fancy | 0.71 |
| 9 | A Case of You | 0.69 |
| 10 | Girl in the War | 0.41 |
| 11 | Long Black Veil | 0.8 |
| 12 | Lua | 0.65 |
| 13 | Make You Feel My Love | 0.41 |
| 14 | Set Yourself on Fire | 0.63 |
| 15 | The Drugs Don't Work | 0.47 |
| 16 | Acquiesce | 0.53 |
| 17 | Everything I've Got | 0.05 |
| 18 | Honey Pie | 0.63 |

TABLE 1-continued

Individual Pearson Correlation values and
total aggregate average correlation value

| Participant ID | Song | Pearson coeff |
| --- | --- | --- |
| 19 | Atlantic City | 0.29 |
| 20 | Morning Theft | 0.72 |
| 21 | Needle In The Hay | 0.62 |
| 22 | West End Blues | 0.31 |
| 23 | Bohemian Rhapsody | 0.53 |
| 24 | Hikayem Bitmedi | 0.62 |
| 25 | How To Save a Life | 0.65 |
| 26 | Numb | 0.26 |
| 27 | Wild World | 0.58 |
| 28 | This Love | 0.36 |
| 29 | Bottom of the Deep Blue Sea | 0.35 |
| 30 | False Confidence | 0.3 |
| 31 | In My Life | 0.47 |
| 32 | Bernadette | 0.66 |
| 33 | Heart of the Country | 0.17 |
|  | Aggregate Pearson Corellation Coefficent | 0.52 | fMRI Study

Data was reanalyzed from a natural music listening task which participants heard musical stimuli during a passive listening task. Seventeen musically-untrained participants were scanned while they listened to 9 minute long segments of symphonies by the baroque composer William Boyce (1711-1779). A whole brain analysis was conducted during the listening session using a general linear model to determine voxels in which activation levels were correlated with higher predicted impact as predicted the combination algorithm using detections from same the 8 objective audio processing metrics used in the behavioral study. FIG. 10B is an fMRI snapshot from this study showing a broad network of neural activations associated with increases during identified peak moments in the music, as identified by the combination algorithm, and compared to non-peak moments.

Analysis of the fMRI study revealed significant tracking of the moving average of the output of the combination algorithm (p<0.01, cluster-corrected at q<0.05; (Cohen's d=0.75) in multiple brain areas including dorsolateral and ventrolateral prefrontal cortex, posterior insula, superior temporal sulcus, basal ganglia, hippocampus and sensorimotor cortex, as shown in FIG. 10B. No brain areas showed negative correlation with predicted impact. Control analysis with loudness measurements revealed significant response only in the sensorimotor cortex, and no brain areas showed negative correlation with loudness. These results demonstrate that distributed brain areas involved in perception and cognition are sensitive to musical impact and that the combination algorithm in combination with detections from 8 objective audio processing metrics, according to examples of the present disclosure, is able to identify temporal moments and segments in digital music data that strongly correlate with the peak brain activity in brain areas involved in perception and cognition.

Moreover, the published research supports this. The foundational research by Blood and Zatorre concludes that, "Subjective reports of chills were accompanied by changes in heart rate, electromyogram, and respiration. As intensity of these chills increased, cerebral blood flow increases and decreases were observed in brain regions thought to be involved in reward motivation, emotion, and arousal, including ventral striatum, midbrain, amygdala, orbito-frontal cortex, and ventral medial prefrontal cortex. These brain structures are known to be active in response to other euphoria-inducing stimuli, such as food, sex, and drugs of abuse." Research by de Fleurian and Pearce states, "Structures belonging to the basal ganglia have been repeatedly linked with chills. In the dorsal striatum, increases in activation have been found in the putamen and left caudate nucleus when comparing music listening with and without the experience of pleasant chills."

Experimental Conclusions

The results of the behavioral and fMRI studies are significant. Clear connections can be drawn back to academic literature, which describe the "chills response" in humans and the elements attendant to those responses. In the self-reporting behavioral study, the test subjects indicated where they are experiencing high musical impact, which is directly related to the musical arousal required for a chill response. And, in the fMRI study, high activation in areas responsible for memory, pleasure, and reward were seen to strongly correspond with the output of the combination algorithm. Accordingly, with the strongest statistical significance possible given the nature and size of the experiments, the behavioral and fMRI studies together validated the ability of embodiments of the present disclosure to predict listeners' neurological activity associated with autonomic physiological responses.

INDUSTRIAL APPLICATION AND EXAMPLE IMPLEMENTATIONS

Several commercial applications for examples of the present disclosure can be employed based on the basic premise that curating large catalogs and making aesthetic judgments around musical recordings is time-consuming. For example, automating the ranking and searching of recordings for specific uses saves time. The amount of time it takes for humans to go through libraries of musical recordings to choose a recording for any use can be prohibitively large. It usually takes multiple listenings to any recording to make an aesthetic assessment. Given that popular music has song lengths between 3-5 minutes, this assessment can take 6-10 minutes per song. There is also an aspect of burnout and fatigue: humans listening to many songs in a row can lose objectivity.

One representative use case example is for a large music catalog holder (e.g., an existing commercial service, such as Spotify, Amazon Music, Apple Music, or Tidal). Typically, large music catalog holders want to acquire new 'paid subscribers' and to convert 'free users' to paid subscribers. Success can be at least partially based on the experience users have when interacting with a free version of the computer application that provides access to their music catalog. Accordingly, by applying examples of the present disclosure, a music catalog service would have the means to deliver the "most compelling" or "most impactful" music to a user, which would, in turn, likely have a direct effect on the user's purchasing decisions. In this example, a database of timestamps could be stored along with a digital music catalog, with the timestamps representing one or more peak impactful moments as detected by a combination algorithm previously run on objective audio processing metrics of each song, and/or one or more impactful music phrases as generated by a phrase detection algorithm previously run on the output of the combination algorithm. Generally, for every song in a service's catalog, metadata in the form of timestamps generated by examples of the present disclosure can be provided and used to enhance a user's experience. In an example embodiment of the present disclosure, samples of songs are provided to a user that contain their peak impactful moments and/or the sample can represent one or more identified impactful phrases.

Another example use case exists in the entertainment and television industries. When directors choose music for their productions, they often must filter through hundreds of songs to find the right recordings and the right portions of the recordings to use. In an example embodiment of the present disclosure, a software application provides identified impactful phrases and/or a chill moments plot to a user (e.g., film or television editor, producer, director, etc.) to enable the user to narrowly focus on highly-impactful music within their chosen parameters (e.g., a genre) and find the right recordings and phrases for their production. This can include the ability to align impactful moments and phrases in songs with moments in a video.

In an example embodiment of the present disclosure, a cloud-based system enables users to search, as an input, through a large catalog of musical recordings stored in a cloud and delivers, as an output, a search result of one or more songs that contains or identifies the most impactful moments in each song result returned. In an example embodiment of the present disclosure, a local or cloud-based computer-implemented service receives digital music recordings as an input, which are processed through examples of the present disclosure to create data regarding timestamps for each song's peak impactful moment(s) and/ or for the most impactful phrase(s), as well as any other musical features provided as a result of the processing using the objective audio processing metrics. Examples include using the stored data to be combined with an organization's pre-existing meta-data for the use of improving recommendation systems using machine learning techniques or to generate actual audio files of the most impactful phrases, depending on the output desired.

Music therapy has also been shown to improve medical outcomes in a large variety of situations, including decreasing blood pressure, better surgery outcomes with patient-selected music, pain management, anxiety treatment, depression, post-traumatic stress disorder (PTSD), and autism. Music therapists have the same problems with music curation as do directors and advertisers—they need to find music of specific genres that their patients can relate to and that also elicit positive responses from their patients. Accordingly, examples of the present disclosure can be used to provide music therapists with segments of music to improve the outcomes of their therapies by increasing the likelihood of a positive (e.g., chills) response from the patient. Some patients with specific ailments (e.g. dementia or severe mental health conditions) cannot assist the therapist with music-selection. If the patient can name a genre, rather than a specific song or artist name, examples of the present disclosure allow the therapist to choose impactful music from that genre. Or if the patient is able to name an artist and the therapist isn't familiar with the artist, examples of the present disclosure can be used to sort the most impactful moments from a list of songs so that the therapist can play those moments to see if any of them generate a response from the patient. Another example is a web interface that helps a music therapist to search for music based on the age of the patient and search for music that is likely to elicit an emotional response from the patient (e.g., find the most impactful music from the time period when the patient was between the ages of 19-25). Another example is a web interface that helps a music therapist to select the least impactful music from a list of genres for the use of meditation exercises with patients that have PTSD.

Social Media

Examples of the present disclosure include social media platforms and applications configured to use the example system and methods described herein to enable users to find the most impactful chill phrases that can be paired with their video content with the hopes of maximizing their views and engagement time, as well as reducing the users' search time for finding a song and searching for a section to use. Examples include controlling a display of a mobile device or a computer to display a visual representation of data of chill moments plot and/or visual identifications of identified phrases (e.g., time stamps, waveforms, etc.), which can accompany a selection from a respective song. In some examples, the display is interactive to enable a user to play or preview the identified phrases through an audio device. Examples of the present disclosure can provide a number of advantages to social media systems, including the ability to find impactful music segments to pair with short video content, maximize video view and engagement time, reduce user input and search time, and reduce licensing costs by diversifying music choices.

Non-limiting example implementations include a) examples of the present disclosure being integrated into existing social media platform, b) systems and methods for auditioning multiple chill phrase selections to see how they pair with user generated content, c) user interfaces and/or UI elements that visually represent the song's chill moment, d) using CB-MIR features to help users discover music from different eras and musical genres, e) using CB-MIR features to further refine audio selections within social media apps, f) providing a way for users to license pieces of music most likely to connect with listeners, g) previewing songs by identified impactful phrases to speed up music search listening time, and h) providing a way for social media platforms to expand song selections while controlling licensing costs.

Figure 11:
FIG. 11 is an illustration of a mobile device display showing a social media application incorporating examples of the present disclosure.

FIG. 11 is an illustration of a mobile device display 1100 showing a social media application incorporating examples of the present disclosure. FIG. 11 illustrates a user-selection of a photograph 1101 as well as an overlay of audio data 1102 visually presenting a music track selection with a window identifying a chill phrase 1103, as well as a line 1104 representing an average of the chill moments plot for the selected music track.

Music Streaming Platforms

Examples of the present disclosure include integration with music streaming services to help users discover music that is more impactful and enhance their playlists by, for example, being able to find and add music to a playlist with similar chill moments characteristics and/or track predicted by systems and methods of the present disclosure to produce highly positive emotional and physical effects in humans. Examples can also allow users to be able to listen to the most impactful section during the song previews.

Figure 12:
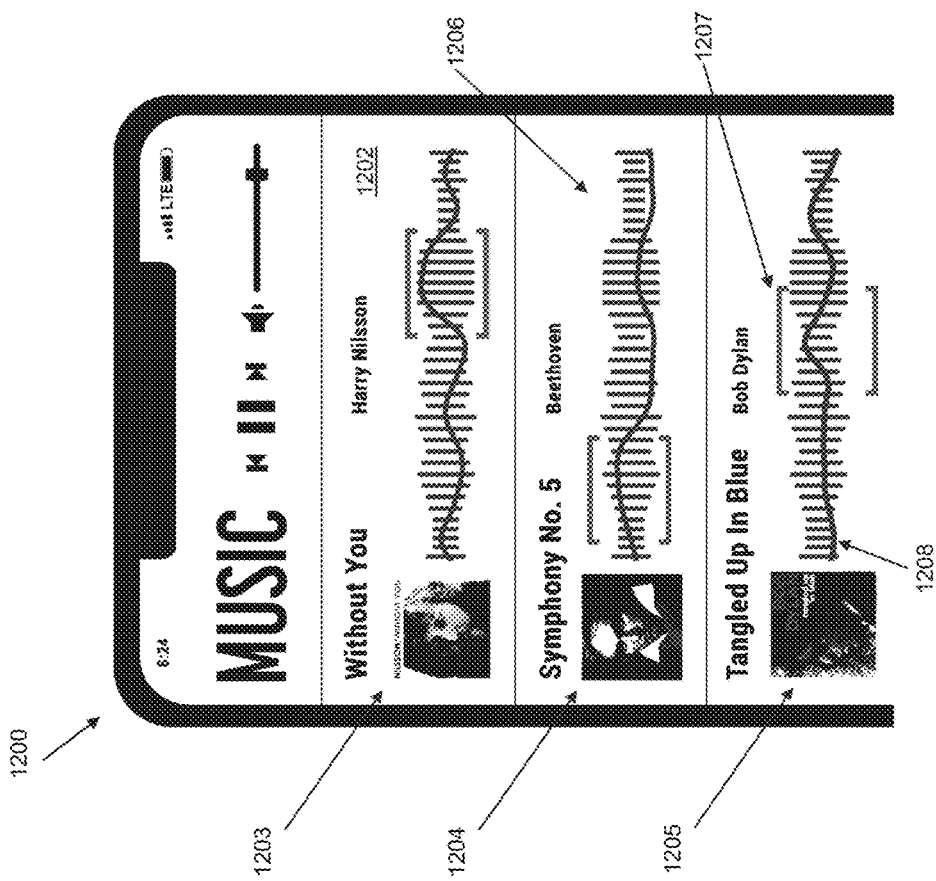
FIG. 12 is an illustration of a mobile device display showing a music streaming application incorporating examples of the present disclosure.

FIG. 12 is an illustration of a mobile device display 1200 showing a music streaming application incorporating examples of the present disclosure. FIG. 12 shows an interface 1202 of a representative music streaming application, illustrating a user-selection of music tracks 1203, 1204, 1205 as well as an overlay of audio data 1206 for each music track with a window 1207 identifying a chill phrase, as well as a line 1208 representing an average of the chill moments plot for the selected music track. Examples include examples of the present disclosure enabling users of a music streaming platform to search for specific chill plot taxonomies, which can assist a user, for example, in the creation of a playlist with all songs that have an impactful finish, beginning, or middle, as well as a playlist of songs that contain a mixture of song taxonomies.

Song Catalogs

Non-limiting example implementations include systems and methods for assisting creators in finding the right music for television series and films. Specifically, the music that fits the timing of a scene. Using existing techniques, especially from large catalogs, this process can be a time-consuming task. Examples of the present disclosure can assist a creator, for example, with the filtering of music search results by impactful phrases within those songs (e.g., phrase length and taxonomy). Examples also enable creation of new types of metadata associated with chill moments (e.g., time stamps indicting chill moment segment locations), which can reduce search time and costs.

Figure 13:
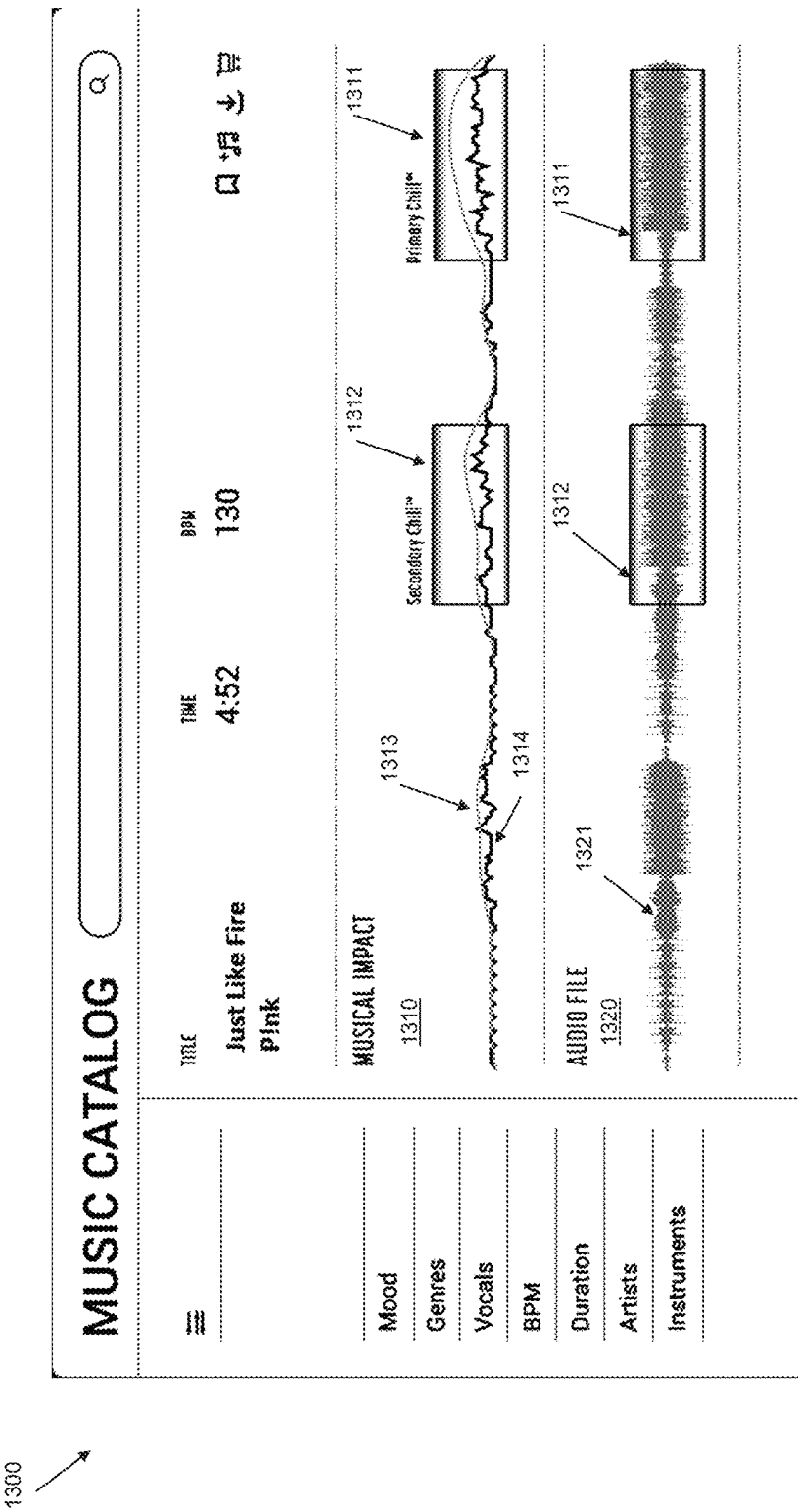
FIG. 13 is an illustration of a computer display showing a music catalog application incorporating examples of the present disclosure.

FIG. 13 is an illustration of a user interface 1300 presented on a computer display showing a music catalog application incorporating examples of the present disclosure. FIG. 13 illustrates a user-selection of a song that presents a window 1320 audio data 1321 representing a music track selection with a separate musical impact window 1310 with an output 1314 from a combination algorithm processing the selected song as well as a line 1313 representing an average of the chill moments plot. The musical impact window 1310 also presents a visual indication of first and second identified impactful phrases 1311, 1312 for the selected music track.

Example features include a) the ability to filter a song database by characteristics of the song's chill moments plot, b) identify predictably impactful song, c) find identified chill segments within songs, d) populate music catalogs with new metadata corresponding to any of the data generated using the methods described herein, and e) reduce search time and licensing costs. Examples of the present disclosure also include user interfaces that provide for user-control over the parameters of the combination algorithm and phrase detection algorithm. For example, allowing a user to adjust or remove weights for one or more input metrics to find different types of phrases. This on-the-fly adjustment can re-run the combination algorithm and phrase detection algorithm without reprocessing individual metrics. This functionality can, for example, enable the search for songs that have big melodic peaks by increasing the weights of the pitch- and melody-related parameters or to increase the weights of timbre related metrics to find moments characterized by a similar acoustic profile. Examples include user interfaces that enable a user to adjust parameters, such as metric weights individually or pre-selected arrangements identifying pre-selected acoustic profiles. Through the use of interactable elements (e.g., toggles, knobs, sliders, or fields), the user can cause the displayed chill moments plot and associated phrase detections to react immediately and interactively.

Example implementations include: a) providing data associated with the chill moments plot in a user interface of video editing software, b) providing data associated with the chill moments plot in a user interface of a music catalog application to make it easier for a user to preview tracks using identified phrases and/or seek in individual tracks based on the chill moments data, c) providing data associated with the chill moments plot in the user interface of an audio editing software, d) providing data associated with the chill moments plot in a user interface of a music selection application on a passenger aircraft to assist passengers' selection of music, e) providing data associated with the chill moments in the user interface of kiosk in a physical and digital record store, and f) enabling a user to preview artists and individual song using impactful phrases.

Examples of the present disclosure include systems and methods for: a) providing data associated with the chill moments plot in social media platforms for generating instant social media slideshows, b) generating chill moments plots for live music, c) populating data associated with the chill moments plot into existing digital music catalogs to enable the preview by impactful phrase, d) providing data associated with the chill moments plot into software for the auditioning of multiple chill moments phrases to see how they pair with a visual edit sequence, and e) processing data associated with the chill moments plot to provide catalog holders new metadata and new opportunities to license impactful portions of their songs.

Production of Audio, Film, Television, Advertising

Figure 14:
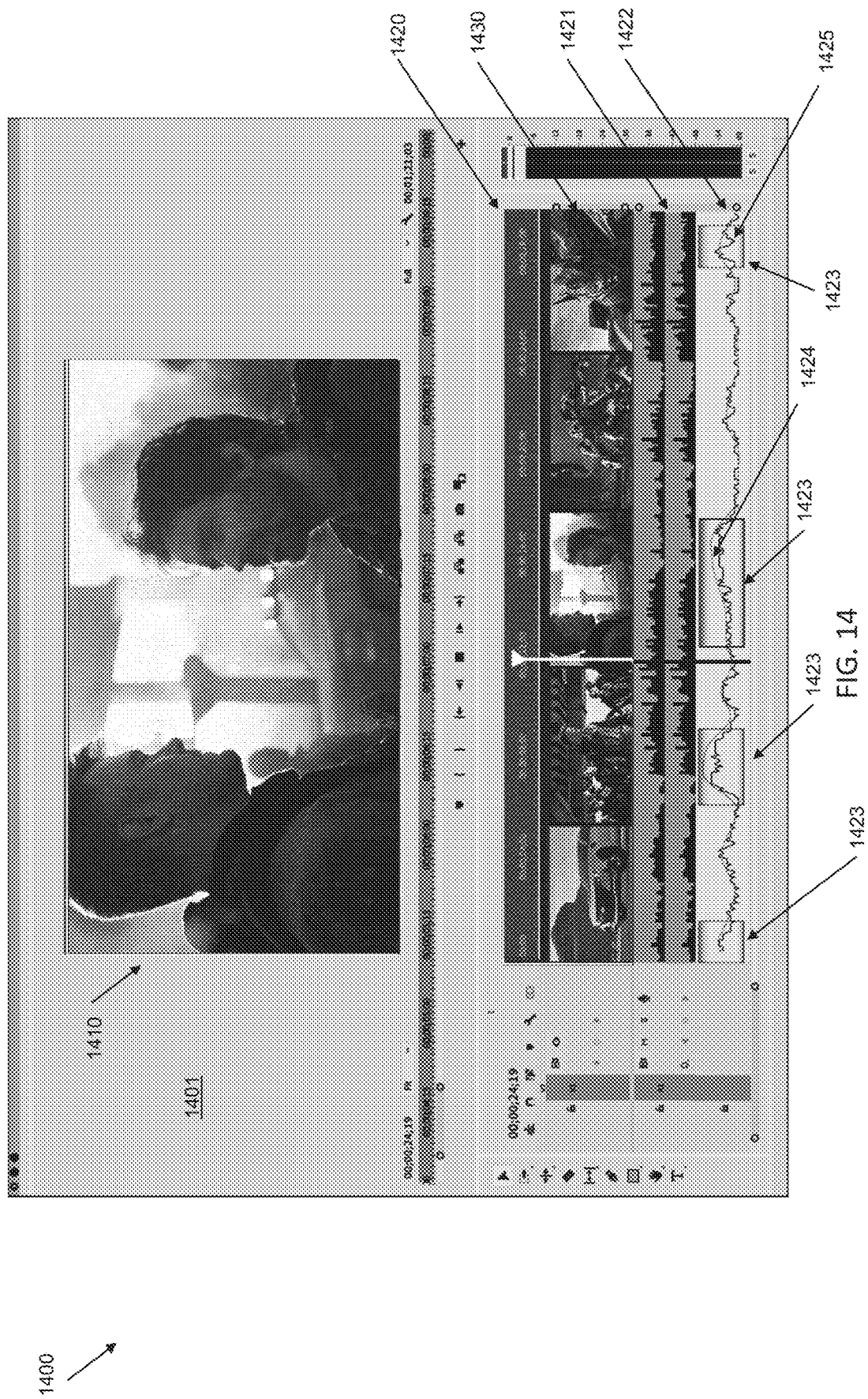
FIG. 14 is an illustration of a computer display showing a video production application incorporating examples of the present disclosure.

Producers and marketers for film, television and advertising want to find music that connects with the audience they are targeting. Examples of the present disclosure include systems and methods for using data associated with the chill moments plot to assist users in finding impactful moments in recorded music and allowing them to pair these chill phrases with their advertisement, television, or film scenes. One example advantage is the ability to pair a song's identified chill segments with key moments in advertisements. FIG. 14 is an illustration of a software interface 1400 on a computer display showing a video production application 1401 incorporating examples of the present disclosure. FIG. 14 shows a current video scene 1410 and an audio-video overlay 1420 showing the time-alignment of the audio track with a video track 1430. The audio-video overlay 1420 includes two-channel audio data 1421 representing a music track selection with an adjacent 1422 window identifying identified chill phrases 1423, as well as a line 1424 representing an average of the chill moments plot 1425 for the selected music track 1421. Example implementations in the audio production context include systems and methods for providing visual feedback of a chill plot and phrase selections in real-time as different mixes of song tracks are configured. Examples can also provide a more detailed breakdown of what metrics are feeding into the chill plot for the current song being edited/mixed to allow producers to gain insight on how they might improve their music.

Gaming

Examples of the present disclosure include systems and methods for enabling game developers to find and use the most impactful sections of music to enhance game experiences, thereby reducing labor and production costs. Examples of the present disclosure include using the system and methods disclosed herein to remove the subjectivity of the game designer and allows them to identify the most impactful parts of the music and synchronize them with the most impactful parts of the gaming experience. For example, during game design, music to indicate cut scenes, level changes, and challenges central to the game experience. Example advantages include enhancing user engagement by integrating the most impactful music, providing music discovering for in-app music purchases, aligning music segments with game scenarios, and reducing labor and licensing costs for game manufacturers. Examples include providing music visualization that is synchronized with chill plot data, which can include synchronizing visual cues in a game, or even dynamic lighting systems in an environment where music is played. Examples include assisting in the creation of music tempo games that derive their timing and interactivity from chill plot peaks. Example implementations include cueing of a chill moment segment of a song in real time, in synch with user gameplay and using data associated with the chill moments plot to indicate cut scenes, level changes, and challenges central to the game experience.

Health & Wellness

People often want to find music that is going to help them relieve stress and improve their wellbeing and this can be done through creating a playlist from music recommendations based on data associated with the chill moments plot. Example implementations of the systems and methods of the present disclosure include: a) using data associated with the chill moments plot to select music that resonates with Alzheimer's or dementia patients, b) using data associated with the chill moments plot as a testing device in a clinical setting to determine the music that best resonates with Alzheimer's or dementia patients, c) using data associated with the chill moments plot to integrate music into wearable heath/wellness products, d) using data associated with the chill moments plot to select music for exercise activities and workouts, e) using data associated with the chill moments plot to help lower a patient's anxiety prior to surgery, f) using data associated with the chill moments plot in a mobile application with which doctors may prescribe curated playlists to treat pain, depression, and anxiety, g) using data associated with the chill moments plot to select music for meditation, yoga, and other relaxation activities, and h) using data associated with the chill moments plot to help patients with pain, anxiety, and depression.

Computer Systems and Cloud-Based Implementations

Figure 15:
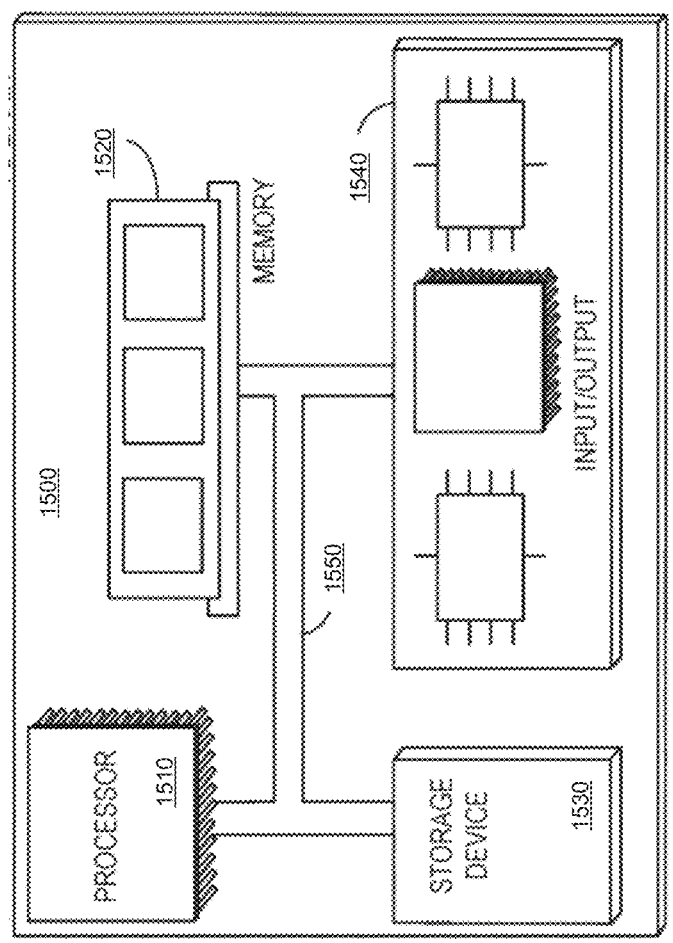
FIG. 15 is a block diagram of one exemplary embodiment of a computer system for use in conjunction with the present disclosure.

FIG. 15 is a block diagram of one exemplary embodiment of a computer system 1500 upon which the present disclosures can be built, performed, trained, etc. For example, referring to FIGS. 1A to 14, any modules or systems can be examples of the system 1500 described herein, for example the input 12, objective audio processing metrics, 111, 112, the detection algorithms 130, the combination algorithm 140, and the phrase detection algorithm 150, output 19, and any of the associated modules or routines described herein. The system 1500 can include a processor 1510, a memory 1520, a storage device 1530, and an input/output device 1540. Each of the components 1510, 1520, 1530, and 1540 can be interconnected, for example, using a system bus 1550. The processor 1510 can be capable of processing instructions for execution within the system 1500. The processor 1510 can be a single-threaded processor, a multi-threaded processor, or similar device. The processor 1510 can be capable of processing instructions stored in the memory 1520 or on the storage device 1530. The processor 1510 may execute operations such as a) executing an audio processing metric, b) applying a threshold to the output of one or more audio processing metrics to detect GLIPhs, c) executing a combination algorithm based on the detections of two or more audio processing metrics, d) executing a phrase detection algorithm on the output of a combination algorithm, e) storing output data from any of the metrics and algorithms disclosed herein, f) receiving a digital music file, g) outputting data from any of the metrics and algorithms disclosed herein, h) generating and/or outputting a digital audio segment based on a phrase detection algorithm, i) receiving a user request for data from any of the metrics and algorithms disclosed here and outputting a result, and j) operating a display device of a computer system, such as a mobile device, to visually present data from any of the metrics and algorithms disclosed herein, among other features described in conjunction with the present disclosure.

The memory 1520 can store information within the system 1500. In some implementations, the memory 1520 can be a computer-readable medium. The memory 1520 can, for example, be a volatile memory unit or a non-volatile memory unit. In some implementations, the memory 1520 can store information related functions for executing objective audio processing metrics and any algorithms disclosed herein. The memory 1520 can also store digital audio data as well as outputs from objective audio processing metrics and any algorithms disclosed herein.

The storage device 1530 can be capable of providing mass storage for the system 1500. In some implementations, the storage device 1530 can be a non-transitory computer-readable medium. The storage device 1530 can include, for example, a hard disk device, an optical disk device, a solid-state drive, a flash drive, magnetic tape, and/or some other large capacity storage device. The storage device 1530 may alternatively be a cloud storage device, e.g., a logical storage device including multiple physical storage devices distributed on a network and accessed using a network. In some implementations, the information stored on the memory 1520 can also or instead be stored on the storage device 1530.

The input/output device 1540 can provide input/output operations for the system 1500. In some implementations, the input/output device 1540 can include one or more of the following: a network interface device (e.g., an Ethernet card or an Infiniband interconnect), a serial communication device (e.g., an RS-232 10 port), and/or a wireless interface device (e.g., a short-range wireless communication device, an 802.7 card, a 3G wireless modem, a 4G wireless modem, a 5G wireless modem). In some implementations, the input/output device 1540 can include driver devices configured to receive input data and send output data to other input/output devices, e.g., a keyboard, a printer, and/or display devices. In some implementations, mobile computing devices, mobile communication devices, and other devices can be used.

In some implementations, the system 1500 can be a microcontroller. A microcontroller is a device that contains multiple elements of a computer system in a single electronics package. For example, the single electronics package could contain the processor 1510, the memory 1520, the storage device 1530, and/or input/output devices 1540.

FIG. 16 is a block diagram of one exemplary embodiment of a cloud-based computer network 1610 for use in conjunction with the present disclosures. The cloud-based computer network 1610 can include a digital storage service 1611 and a processing service 1612, each of which can be provisioned by one or more individual computer processing and storage devices located in one or more physical locations. The cloud-based computer network 1610 can send and receive 1621, 1631, via the internet or other digital connection means, data from individual computer systems 1620 (e.g., a personal computer or mobile device) as well as from networks 1630 of individual computer systems 1620 (e.g., a server operating a music streaming service). The cloud-based computer network 1610 may facilitate or complete the execution of operations such as a) executing an audio processing metric, applying a threshold to the output of one or more audio processing metrics to detect GLIPhs, b) executing a combination algorithm based on the detections of two or more audio processing metrics, c) executing a phrase detection algorithm based on the output of a combination algorithm, d) storing output data from any of the metrics and algorithms disclosed herein, e) receiving a digital music file, f) outputting data from any of the metrics and algorithms disclosed herein, g) generating and/or outputting a digital audio segment based on a phrase detection algorithm, h) receiving a user request for data from any of the metrics and algorithms disclosed here and outputting a result, and i) operating a display device of a computer system, such as a mobile device, to visually present from data any of the metrics and algorithms disclosed herein, among other features described in conjunction with the present disclosure.

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example, a computer-readable medium, for execution by, or to control the operation of, a processing system. The computer readable medium can be a machine-readable storage device, a machine-readable storage substrate, a memory device, a composition of matter effecting a machine-readable propagated signal, or a combination of one or more of them.

Various embodiments of the present disclosure may be implemented at least in part in any conventional computer programming language. For example, some embodiments may be implemented in a procedural programming language (e.g., "C" or ForTran95), or in an object-oriented programming language (e.g., "C++"). Other embodiments may be implemented as a pre-configured, stand-alone hardware element and/or as preprogrammed hardware elements (e.g., application specific integrated circuits, FPGAs, and digital signal processors), or other related components.

The term "computer system" may encompass all apparatus, devices, and machines for processing data, including, by way of non-limiting examples, a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Such implementation may include a series of computer instructions fixed either on a tangible, non-transitory medium, such as a computer readable medium. The series of computer instructions can embody all or part of the functionality previously described herein with respect to the system. Computer readable media suitable for storing computer program instructions and data include all forms of non-volatile or volatile memory, media and memory devices, including by way of example, semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Those skilled in the art should appreciate that such computer instructions can be written in a number of programming languages for use with many computer architectures or operating systems. Furthermore, such instructions may be stored in any memory device, such as semiconductor, magnetic, optical, or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the present disclosure may be implemented as a combination of both software (e.g., a computer program product) and hardware. Still other embodiments of the present disclosure are implemented as entirely hardware, or entirely software.

One skilled in the art will appreciate further features and advantages of the disclosures based on the provided for descriptions and embodiments. Accordingly, the inventions are not to be limited by what has been particularly shown and described. For example, although the present disclosure provides for processing digital audio data to identify impactful moments and phrases in song, the present disclosures can also be applied to other types of audio data, such as speech or environmental noise, to assess their acoustic characteristics and their ability to elicit physical responses from human listeners. All publications and references cited herein are expressly incorporated herein by reference in their entirety.

Examples of the above-described embodiments can include the following:

1. A computer-implemented method of identifying segments in music, the method comprising: receiving, via an input operated by a processor, digital music data; processing, using a processor, the digital music data using a first objective audio processing metric to generate a first output; processing, using a processor, the digital music data using a second objective audio processing metric to generate a second output; generating, using a processor, a first plurality of detection segments using a first detection routine based on regions in the first output where a first detection criteria is satisfied; generating, using a processor, a second plurality of detection segments using a second detection routine based on regions in the second output where a second detection criteria is satisfied; combining, using a processor, the first plurality of detection segments and the second plurality of detection segments into a single plot representing concurrences of detection segments in the first and second pluralities of detection segments; wherein the first and second objective audio processing metrics are different.

2. The method of example 1, comprising: identifying a region in the single plot containing the highest number of concurrences during a predetermined minimum length of time requirement; and outputting an indication of the identified region.

3. The method of example 1 or example 2, wherein combining comprises calculating a moving average of the single plot.

4. The method of example 3, comprising: identifying a region in the single plot where the moving average is above an upper bound; and outputting an indication of the identified region.

5. The method of any of examples 1 to 4, wherein one or both of the first and second objective audio processing metrics are first-order algorithms and/or are configured to output first-order data.

6. The method of any of examples 1 to 5, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

7. The method of any of examples 1 to 6, further comprising: applying a low-pass envelope to either output of the first or second objective audio processing metrics.

8. The method of any of examples 1 to 7, wherein the first or second detection criteria comprises an upper or lower boundary threshold.

9. The method of any of examples 1 to 8, wherein detecting comprises applying a length requirement filter to eliminate detection segments outside of a desired length range.

10. The method of any of examples 1 to 9, wherein the combining comprises applying a respective weight to first and second plurality of detection.

11. A computer system, comprising: an input module configured to receive a digital music data; an audio processing module configured to receive the digital music data and execute a first objective audio processing metric on the digital music data and a second objective audio processing metric on the digital music data, the first and second metrics generating respective first and second outputs; a detection module configured to receive, as inputs, the first and second outputs and, generate, for each of the first and second outputs, a set of one or more segments where a detection criteria is satisfied; a combination module configured to receive, as inputs, the one or more segments detected by the detection module and aggregate each segment into a single dataset containing concurrences of the detections.

12. The computer system of example 11, comprising: a phrase identification module configured to receive, as input, the single dataset of concurrences from the combination module and identify one or more regions where the highest average value of the single dataset occur during a predetermined minimum length of time.

13. The computer system of example 12, where the phrase identification module is configured to identify the one or more regions based on where a moving average of the single dataset is above an upper bound.

14. The computer system of examples 12 or 23, where the phrase identification module is configured to apply a length requirement filter to eliminate regions outside of a desired length range.

15. The computer system of any of examples 11 to 14, wherein the combination module is configured to calculate a moving average of the single plot.

16. The computer system of any of examples 11 to 15, wherein one or both of the first and second objective audio processing metrics are first-order algorithms and/or are configured to output first-order data.

17. The computer system of any of examples 11 to 16, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

18. The computer system of any of examples 11 to 17, wherein the detection module is configured to apply a low-pass envelope to either output of the first or second objective audio processing metrics.

19. The computer system of any of examples 11 to 18, wherein the detection criteria comprises an upper or lower boundary threshold.

20. The computer system of any of examples 11 to 1, wherein the detection module is configured to apply a length requirement filter to eliminate detection segments outside of a desired length range.

21. The computer system of any of examples 11 to 20, wherein the combination module is configured to applying respective weight to the first and second plurality of detections before aggregating each detected segment based on the respective weight.

22. A computer program product, comprising a tangible, non-transient computer usable medium having computer readable program code thereon, the computer readable program code comprising code configured to instruct a processor to: receive digital music data; process the digital music data using a first objective audio processing metric to generate a first output; process the digital music data using a second objective audio processing metric to generate a second output; generate a first plurality of detection segments using a first detection routine based on regions in the first output where a first detection criteria is satisfied; generate a second plurality of detection segments using a second detection routine based on regions in the second output where a second detection criteria is satisfied; combine the first plurality of detection segments and the second plurality of detection segments into a single plot based on concurrences of detection segments in the first and second pluralities of detection segments; wherein the first and second objective audio processing metrics are different.

23. The computer program product of example 22, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

24. The computer program product of examples 22 or 23, containing instruction to: identify a region in the single plot containing the highest number of concurrences during a predetermined minimum length of time requirement; and output an indication of the identified region.

25. The computer program product of any of examples 22 to 24, containing instruction to: identify one or more regions where the highest average value of the single dataset occur during a predetermined minimum length of time.

26. The computer program product of any of examples 22 to 25, containing instruction to: calculate a moving average of the single plot 27. The computer program product of any of examples 22 to 26, wherein the first or second detection criteria comprises an upper or lower boundary threshold.

28. The computer program product of any of examples 22 to 27, containing instruction to: applying a length requirement to filter to eliminate detection segments outside of a desired length range.

29. A computer-implemented method of identifying segments in music having characteristics suitable for inducing autonomic psychological responses in human listeners, the method comprising: receiving, via an input operated by a processor, digital music data; processing, using a processor, the digital music data using two or more objective audio processing metrics to generate a respective two or more outputs; detecting, via a processor, a plurality of detection segments in each of the two or more outputs based on regions where a respective detection criteria is satisfied; combining, using a processor, the plurality of detection segments in each of the two or more outputs into a single chill moments plot based on concurrences in the plurality of detection segments; wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

30. The method of example 29, comprising: identifying, using a processor, one or more regions in the single chill moments plot containing the highest number of concurrences during a minimum length requirement; and outputting, using a processor, an indication of the identified one or more regions.

31. The method of examples 29 or 30, comprising: displaying, via a display device, a visual indication of values of the single chill moments plot with respect to a length of the digital music data.

32. The method of any of examples 29 to 32, comprising: displaying, via a display device, a visual indication of the digital music data with respect to a length of the digital music data overlaid with a visual indication of values of the single chill moments plot with respect to the length of the digital music data.

33. The method of example 32, wherein the visual indication of values of the single chill moments plot comprises a curve of a moving average of the values of the single chill moments plot.

34. The method of any of examples 29 to 33, comprising: identifying a region in the single chill moments plot containing the highest number of concurrences during a predetermined minimum length of time requirement; and outputting an indication of the identified region.

35. The method of example 33, wherein the outputting includes displaying, via a display device, a visual indication of the identified region.

36. The method of example 33, wherein the outputting includes displaying, via a display device, a visual indication of the digital music data with respect to a length of the digital music data overlaid with a visual indication of the identified region in the digital music data.

37. A computer-implemented method of providing information identifying impactful moments in music, the method comprising: receiving, via an input operated by a processor, a request for information relating to the impactful moments in a digital audio recording, the request containing an indication of the digital audio recording; accessing, using a processor, a database storing a plurality of identifications of different digital audio recordings and a corresponding set of information identifying impactful moments in each of the different digital audio recordings, the corresponding set including at least one of: a start and stop time of a chill phrase or values of a chill moments plot; matching, using a processor, the received identification of the digital audio recording to an identification of the plurality of identifications in the database, the matching including finding an exact match or a closest match; and outputting, using a processor, the set of information identifying impactful moments of the matched identification of the plurality of identifications in the database.

38. The method of example 37, wherein the corresponding set of information identifying impactful moments in each of the different digital audio recordings comprises information created using a single plot of detection concurrences for each of the different digital audio recordings generated using the method of example 1 for each of the different digital audio recordings.

39. The method of example 37, wherein the corresponding set of information identifying impactful moments in each of the different digital audio recordings comprises information created using a single chill moments plots for each of the different digital audio recordings generated using the method of example 29 for each of the different digital audio recordings, single plot 40. A computer-implemented method of displaying information identifying impactful moments in music, the method comprising: receiving, via an input operated by a processor, an indication of a digital audio recording; receiving, via a communication interface operated by a processor, information identifying impactful moments in the digital audio recording, the information include at least one of: a start and stop time of a chill phrase, or values of a chill moments plot; displaying, using a processor, the received identification of the digital audio recording to an identification of the plurality of identifications in the database, the matching including finding an exact match or a closest match; outputting, using a display device, a visual indication of the digital audio recording with respect to a length of time of the digital audio recording overlaid with a visual indication of the chill phrase and/or the values of the chill moment plot with respect to the length of time of the digital audio recording.

What is claimed is:

1. A computer-implemented method of identifying segments in music, the method comprising:
    receiving, via an input operated by a processor, digital audio data;
    processing, using a processor, the digital audio data using a first objective audio processing metric to generate a first output, the first output comprising a value of the first objective audio processing metric at each one of a first continuous plurality of sequential time segments of the digital audio data;
    processing, using a processor, the digital audio data using a second objective audio processing metric to generate a second output, the first output comprising a value of the second objective audio processing metric at each one of a second continuous plurality of sequential time segments;
    generating, using a processor, a first plurality of detection segments using a first detection routine based on regions in the first output where a first detection criteria is satisfied, the first detection criteria defining a first threshold relative to the first output, and each of the first plurality of detection segments defining an indication of the respective value of the first objective audio processing metric satisfying the first detection criteria in a respective time segment of the first plurality of time segments;

generating, using a processor, a second plurality of detection segments using a second detection routine based on regions in the second output where a second detection criteria is satisfied, the second detection criteria defining a second threshold relative to the second output, and each of the second plurality of detection segments defining an indication of the respective value of the second objective audio processing metric satisfying the second detection criteria in a respective time segment of the second plurality of time segments; and combining, using a processor, the first plurality of detection segments and the second plurality of detection segments into a single plot representing concurrences of detection segments in the first and second pluralities of detection segments;

wherein the first and second objective audio processing metrics are different.

2. The method of claim 1, comprising:
identifying a region in the single plot containing the highest number of concurrences during a predetermined minimum length of time requirement; and
outputting an indication of the identified region.

3. The method of claim 1, wherein combining comprises calculating a moving average of the single plot.

4. The method of claim 3, comprising:
identifying a region in the single plot where the moving average is above an upper bound; and
outputting an indication of the identified region.

5. The method of claim 1, wherein one or both of the first and second objective audio processing metrics are first-order algorithms and/or are configured to output first-order data.

6. The method of claim 1, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

7. The method of claim 1, further comprising:
applying a low-pass envelope to either output of the first or second objective audio processing metrics.

8. The method of claim 1, wherein the first or second detection criteria comprises an upper or lower boundary threshold.

9. The method of claim 1, wherein detecting comprises applying a length requirement filter to eliminate detection segments outside of a desired length range.

10. The method of claim 1, wherein the combining comprises applying a respective weight to first and second plurality of detection.

11. A computer system, comprising:
an input module configured to receive a digital audio data;
an audio processing module configured to receive the digital audio data and execute a first objective audio processing metric on the digital audio data and a second objective audio processing metric on the digital audio data, the first and second metrics generating respective first and second outputs, each of the first and second outputs comprising a value of a respective objective audio processing metric at each one of a respective continuous plurality of sequential time segments of the digital audio data;

a detection module configured to receive, as inputs, the first and second outputs and, generate, for each of the first and second outputs, a set of one or more detection segments where a respective detection criteria is satisfied, the respective detection criteria defining a respective threshold relative to the respective output, and each of the respective one or more segments defining an indication of the respective value of the respective objective audio processing metric satisfying the respective detection criteria in a respective time segment of the respective continuous plurality of sequential time segments; and a combination module configured to receive, as inputs, the one or more segments detected by the detection module and aggregate each segment into a single dataset containing concurrences of the detection segments.

12. The computer system of claim 11, comprising:
a phrase identification module configured to receive, as input, the single dataset of concurrences from the combination module and identify one or more regions where the highest average value of the single dataset occur during a predetermined minimum length of time.

13. The computer system of claim 12, where the phrase identification module is configured to identify the one or more regions based on where a moving average of the single dataset is above an upper bound.

14. The computer system of claim 12, where the phrase identification module is configured to apply a length requirement filter to eliminate regions outside of a desired length range.

15. The computer system of claim 11, wherein the combination module is configured to calculate a moving average of the single plot.

16. The computer system of claim 11, wherein one or both of the first and second objective audio processing metrics are first-order algorithms and/or are configured to output first-order data.

17. The computer system of claim 11, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

18. The computer system of claim 11, wherein the detection module is configured to apply a low-pass envelope to either output of the first or second objective audio processing metrics.

19. The computer system of claim 11, wherein the detection criteria comprises an upper or lower boundary threshold.

20. The computer system of claim 11, wherein the detection module is configured to apply a length requirement filter to eliminate detection segments outside of a desired length range.

21. The computer system of claim 11, wherein the combination module is configured to applying respective weight to the first and second plurality of detections before aggregating each detected segment based on the respective weight.

22. A computer program product, comprising a tangible, non-transient computer usable medium having computer readable program code thereon, the computer readable program code comprising code configured to instruct a processor to:

receive digital audio data;

process the digital audio data using a first objective audio processing metric to generate a first output, the first output comprising a value of the first objective audio processing metric at each one of a first continuous plurality of sequential time segments of the digital audio data;

process the digital audio data using a second objective audio processing metric to generate a second output, the first output comprising a value of the second objective audio processing metric at each one of a second continuous plurality of sequential time segments;

generate a first plurality of detection segments using a first detection routine based on regions in the first output where a first detection criteria is satisfied, the first detection criteria defining a first threshold relative to the first output, and each of the first plurality of detection segments defining an indication of the respective value of the first objective audio processing metric satisfying the first detection criteria in a respective time segment of the first plurality of time segments;

generate a second plurality of detection segments using a second detection routine based on regions in the second output where a second detection criteria is satisfied, the second detection criteria defining a second threshold relative to the second output, and each of the second plurality of detection segments defining an indication of the respective value of the second objective audio processing metric satisfying the second detection criteria in a respective time segment of the second plurality of time segments; and combine the first plurality of detection segments and the second plurality of detection segments into a single plot based on concurrences of detection segments in the first and second pluralities of detection segments;

wherein the first and second objective audio processing metrics are different.

23. The computer program product of claim 22, wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

24. The computer program product of claim 22, containing instruction to:
identify a region in the single plot containing the highest number of concurrences during a predetermined minimum length of time requirement; and
output an indication of the identified region.

25. The computer program product of claim 22, containing instruction to:
identify one or more regions where the highest average value of the single dataset occur during a predetermined minimum length of time.

26. The computer program product of claim 22, containing instruction to:
calculate a moving average of the single plot.

27. The computer program product of claim 22, wherein the first or second detection criteria comprises an upper or lower boundary threshold.

28. The computer program product of claim 22, containing instruction to:
apply a length requirement to filter to eliminate detection segments outside of a desired length range.

29. A computer-implemented method of identifying segments in music having characteristics suitable for inducing autonomic psychological responses in human listeners, the method comprising:

receiving, via an input operated by a processor, digital audio data;

processing, using a processor, the digital audio data using two or more objective audio processing metrics to generate a respective two or more outputs, each of the two or more outputs comprising a value of a respective one of the two or more objective audio processing metrics at each one of a respective continuous plurality of sequential time segments of the digital audio data;

detecting, via a processor, a plurality of detection segments in each of the two or more outputs based on regions where a respective detection criteria is satisfied, the respective detection criteria defining a respective threshold relative to a respective output of the two or more outputs, and each of the respective plurality of detection segments defining an indication of the value of the respective objective audio processing metric satisfying the respective detection criteria in a respective time segment of the respective continuous plurality of sequential time segments; and combining, using a processor, the plurality of detection segments in each of the two or more outputs into a single chill moments plot based on concurrences in the plurality of detection segments;

wherein the first and second objective audio processing metrics are selected from a group consisting of: loudness, loudness band ratio, critical band loudness, predominant pitch melodia, spectral flux, spectrum centroid, inharmonicity, dissonance, sudden dynamic increase, sustained pitch, harmonic peaks ratio, or key changes.

30. The method of claim 29, comprising:
identifying, using a processor, one or more regions in the single chill moments plot containing the highest number of concurrences during a minimum length requirement; and
outputting, using a processor, an indication of the identified one or more regions.

* * * * *